US006884842B2

(12) United States Patent
Soane et al.

(10) Patent No.: US 6,884,842 B2
(45) Date of Patent: Apr. 26, 2005

(54) MOLECULAR COMPOUNDS HAVING COMPLEMENTARY SURFACES TO TARGETS

(75) Inventors: David S. Soane, Piedmont, CA (US); Stephen E. Barry, Oakland, CA (US); Andrew Goodwin, Oakland, CA (US); David A. Offord, Castro Valley, CA (US); Michael G. Perrott, San Francisco, CA (US)

(73) Assignee: Alnis BioSciences, Inc., Emeryville, CA (US)

( * ) Notice: Subject to any disclaimer, the term of this patent is extended or adjusted under 35 U.S.C. 154(b) by 179 days.

(21) Appl. No.: 10/055,837

(22) Filed: Oct. 26, 2001

(65) Prior Publication Data

US 2003/0153001 A1 Aug. 14, 2003

Related U.S. Application Data

(63) Continuation of application No. 09/172,921, filed on Oct. 14, 1998, now abandoned.
(60) Provisional application No. 60/103,616, filed on Oct. 9, 1998, and provisional application No. 60/061,805, filed on Oct. 14, 1997.

(51) Int. Cl.[7] ........................ C08G 63/48; C08G 63/91; C08G 89/00; C08H 1/00
(52) U.S. Cl. ................. 525/54.1; 525/54.2; 525/54.23; 526/238.1; 526/238.2; 526/238.23; 424/450; 424/489; 424/499
(58) Field of Search ............................. 525/54.1, 54.2, 525/54.23; 526/238.1, 238.2, 238.23; 424/450, 489, 499

(56) References Cited

U.S. PATENT DOCUMENTS

| 4,075,411 A | 2/1978 | Dickstein |
| 4,097,470 A | 6/1978 | Drobnik et al. |
| 4,107,288 A | 8/1978 | Oppenheim et al. |
| 4,127,730 A | 11/1978 | Wulff et al. |
| 4,622,362 A | 11/1986 | Rembaum |
| 4,770,906 A | 9/1988 | Harwell et al. |
| 4,800,162 A | 1/1989 | Matson |
| 5,057,427 A | 10/1991 | Wald et al. |
| 5,077,217 A | 12/1991 | Matson et al. |
| 5,110,833 A | 5/1992 | Mosbach |
| 5,152,978 A | 10/1992 | Baba et al. |
| 5,200,315 A | 4/1993 | Sutton et al. |
| 5,310,648 A | 5/1994 | Arnold et al. |
| 5,349,036 A | 9/1994 | Simpson et al. |
| 5,455,027 A | 10/1995 | Zalipsky et al. |
| 5,459,127 A | 10/1995 | Felgner et al. |
| 5,459,176 A | 10/1995 | Bae et al. |
| 5,461,175 A | 10/1995 | Fischer et al. |
| 5,510,118 A | 4/1996 | Bosch et al. |
| 5,534,270 A | 7/1996 | De Castro |
| 5,587,143 A | 12/1996 | Wong |
| 5,587,273 A | 12/1996 | Yan et al. |
| 5,630,978 A | 5/1997 | Domb |
| 5,663,387 A | 9/1997 | Singh |
| 5,728,296 A | 3/1998 | Hjerten et al. |
| 5,814,223 A | 9/1998 | Hjerten et al. |
| 5,821,311 A | 10/1998 | Mosbach et al. |
| 5,834,025 A | 11/1998 | de Garavilla et al. |
| 5,858,296 A | 1/1999 | Domb |
| 5,872,198 A | 2/1999 | Mosbach et al. |
| 5,914,367 A | 6/1999 | Dordick et al. |
| 5,916,445 A | 6/1999 | Hjerten et al. |
| 5,916,596 A | 6/1999 | Desai et al. |
| 5,959,050 A | 9/1999 | Mosbach et al. |
| 5,994,110 A | 11/1999 | Mosbach et al. |
| 6,051,372 A | 4/2000 | Bayerl et al. |
| 6,127,154 A | 10/2000 | Mosbach et al. |
| 6,177,513 B1 | 1/2001 | Takeuchi et al. |
| 6,217,901 B1 | 4/2001 | Perrott et al. |

FOREIGN PATENT DOCUMENTS

| DE | 19627 162 C1 | 8/1997 |
| DE | 198 23 432 A1 | 3/1999 |
| SE | 9102843 | 3/1993 |
| SE | 9403154 | 3/1996 |
| WO | WO 88/09981 | 12/1988 |
| WO | WO 93/05068 | 3/1993 |
| WO | WO 93/09075 | 5/1993 |
| WO | WO 94/11403 | 5/1994 |
| WO | WO 94/14835 | 7/1994 |
| WO | WO 94/26381 | 11/1994 |
| WO | WO 95/21673 | 8/1995 |
| WO | WO 96/37527 | 11/1996 |
| WO | WO 97/22366 | 6/1997 |

OTHER PUBLICATIONS

Ananthapadmanabhan, K.P., "Surfactant solutions: Adsorption and aggregation properties" *Interactions of Surfactants with Polymers and Proteins*, E. D. Goddard and K. P. Ananthapadmanabhanm eds., CRC Press, Boca Raton, Chapter 2, pp. 5–58 (1993).

Antonietti et al., "Synthesis and properties of model–micronetworks" *Makromol. Chem., Macromol. Symp.*, 30:81–93 (1989).

(Continued)

*Primary Examiner*—Nathan M. Nutter
(74) *Attorney, Agent, or Firm*—Jacqueline S. Larson

(57) ABSTRACT

Synthetic polymer complements (SPCs) are provided, as well as methods for their synthesis and use. The SPCs may have surfaces that include functional groups that are complementary to surface sites of targets such as nanostructures or macromolecular targets, and may be capable of specifically interacting with such targets. The positions of the functional groups in one embodiment are stabilized by a polymer network. The SPCs are formed by contacting the target with a set of monomers which self-assemble on the target, and then are polymerized into a network to form the synthetic polymer complement. At least a portion of the surface of the resulting SPC thus may include an imprint of the target. The complex of the SPC and the target may be the desired product. Alternatively, the target is released, for example, by controllably expanding and contracting the crosslinked network. The SPC is isolated and used in many applications.

36 Claims, 31 Drawing Sheets

OTHER PUBLICATIONS

Antonietti, Markus, "Polymerization in microemulsions—a new approach to ultrafine, highly functionalized polymer dispersions" *Macromol. Chem. Phys., 196:*441–446 (1995).

Arshady et al., "Synthesis of substrate–selective polymers by host–guest polymerization" *Makromol. Chem., 182:*687–692 (1981).

Ayala et al., "Protein extraction and activity in reverse micelles of a nonionic detergent" *Biotechnology and Bioengineering, 39:*806–814 (1992).

Bishop et al., "Self–assembled monolayers: recent developments and applications" *Curr. Op. Colloid and Interface Sciences, 1:*127–136 (Feb. 1996).

Boone, Travis D., "Overview of modeling efforts in support of microencapsulated polymer mandrel formation" *J. Moscow Phys. Soc., 8:*79–86 (1998).

Bunin et al., "The combinatorial synthesis and chemical and biological evaluation of a 1,4–benzodiazepine library" *Proc. Natl. Acad. Sci. U.S.A., 91:*4708–4712 (1994).

Chiannilkulchai et al., "Doxorubicin–loaded nanoparticles: Increased efficiency in murine hepatic metastases" *Sel. Cancer Therpies, 5:*1–11 (1990).

Clark et al., "Proligand: An approach to de novo molecular design. 1. Application to the design of organic molecules" *J. Comput. Aided Mol. Des., 9:*13–32 (1995).

Corpart et al., "Formation and polymerization of microemulsions containing a mixture of cationic and anionic monomers" *Colloid & Polymer Science, 271:*1055–1067 (1993).

Duček, K., ed., "Responsive gels: Volume transitions I" *Advances in Polymer Science,* vol. 109, Springer Verlag (1993) (Table of Contents).

Duček, K., ed., "Responsive gels: Volume transitions II" *Advances in Polymer Science,* vol. 110, Springer Verlag (1993) (Table of Contents).

Eisenberg et al., "Electrolyte solutions" *Physical Chemistry with Applications to the Life Sciences* Benjamin/Cummings, Menlo Park, CA, Chapter 8, pp. 337–340 (1979).

Ekberg et al., "Molecular imprinting: a technique for producing specific separation materials" *Tibetch 7:*92–96 (1989).

Fodor et al., "Light–directed, spatially addressable parallel chemical synthesis" *Science, 251:*767–773 (1991).

Gao et al., "Vicinal diol cyclic sulfates: Like epoxides only more reactive" *J. Am. Chem. Soc., 110:*7538–7539 (1988).

Goto et al., "Design of surfactants suitable for protein extraction by reversed micelles" *Biotech. and Bioeng., 54:*26–32 (1997).

Gray et al., "Highly ordered polymer–inorganic nanocomposites via monomer self–assembly: In situ condensation approach" *Advanced Materials, 9:*731–736 (1997).

Griffin, William C., "Calculation of HLB values of nonionic surfactants" *Journal of the Society of Cosmetic Chemists, 5:*249–256 (1954).

Guyot et al., "Reactive surfactants in emulsion polymerization" *Advances in Polymer Science, 111:*45–65 (1994).

Haupt et al., "Binding assays for drugs and herbicides using molecularly imprinted polymer particles as recognition elements in different assay formats" *213th ACS Natl Meeting Abstracts,* Section I&EC, No. 032, John Wiley and Sons, New York, (1997).

Hedborg et al., "Some studies of molecularly–imprinted polymer membranes in combination with field–effect devices" *Sensors and Actuators A, 37–38:*796–799 (1993).

Hermanson, Greg T., *Bioconjugation Techniques,* Academic Press: San Diego, pp. 57–59, 183–185, 620–622, (1996).

Jansen et al., "Molecular design using the minireceptor concept" *J. Chem. Inf. Comput. Sci., 37:*812–818 (1997).

Joynes et al., "Novel polymerizable mono– and divalent quaternary ammonium cationic surfactants: 1. Synthesis, structural characterization and homopolymerization" *Polymer, 37:*1453–1462 (1996).

Kempe et al., "Binding studies on substrate and enantio selective molecularly imprinted polymers" *Analytical Letters, 24:*1137–1145 (1991).

Kriz et al., "Introducing biomimetic sensors based on molecularly imprinted polymers as recognition elements" *Anal. Chem., 67:*2142–2144 (1995).

Lewis et al., "Automated site–directed drug design using molecular lattices" *J. Mol. Graph., 10:*66–78 (1992).

March, Jerry, "Reactions, mechanisms, and structure" *Advanced Organic Chemistry,* 3rd ed., Wiley–Interscience, New York, pp. 346–347 (1985).

Mayes et al., "Molecularly imprinted polymer beads; Suspension polymerization using a liquid perfluorocarbon as the dispersing phase" *Anal. Chem., 68:*3769–3774 (1996).

Martinek et al., "The principles of enzyme stabilization. II. Increase in the thermostability of enzymes as a result of multipoint noncovalent interaction with a polymeric support" *Biochemica et Biophysica Acta, 485:*13–28 (1977).

Middleman, S., "Mixing in stirred tanks" *Fundamentals of Polymer Processing,* McGraw–Hill, Inc., pp. 340–349 (1977).

Monfardini et al., "Stabilization of substances in circulation" *Bioconjugate Chemistry, 9:*418–450 (1998).

Mosbach, Klaus, "Molecular imprinting" *Trends Biochem. Sci., 19:*9–14 (1994).

Mosbach et al., "The emerging technique of molecular imprinting and its future impact on biotechnology" *Biotechnology, 14:*163–170 (1996).

O'Shannessy et al., "Molecular recognition in synthetic polymers" *Journal of Molecular Recognition, 2:*1–5 (1989).

Paradkar et al., "Aqueous–like activity of α–chymotrypsin dissolved in nearly anhydrous organic solvents" *J. Am. Chem. Soc., 116:*5009–5010 (1994).

Pauling, Linus "A theory of the structure and process of formation of antibodies" *J. Am. Chem., 62:*2463–2657 (1940).

Perry et al., "Reaction kinetics, reactor design, and thermodynamics" *Perry's Chemical Engineers' Handbook; Section 4,* McGraw–Hill, Inc., pp. 4–4 to 4–8, 4–51 to 4–52 (1984).

Rahaman et al., "Structural characterization of α–chymotrypsin–containing AOT reversed micelles" *J. Phys. Chem., 95:*1799–1811 (1991).

Ramström et al., "Recognition sites incorporating both pyridinyl and carboxy functionalities prepared by molecular imprinting" *J. Org. Chem., 58:*7562–7564 (1993).

Roe et al., "Builder v.2: Improving the chemistry of a de novo design strategy" *J. Comput. Aided Mol. Des., 9:*269–282 (1995).

Rosen, S., "Polymer solubility and solutions" *Fundamental Principles of Polymeric Materials,* John Wiley & Sons, Inc., Chapter VII, pp. 82–101 (1993).

Rosen, S., "Polymerization practice" *Fundamental Principles of Polymeric Materials,* John Wiley & Sons, Inc., Chapter XII, pp. 214–229 (1993).

Rotstein et al., "GroupBuild: A fragment–based method for de novo drug design" *J. Med. Chem. 36:*1700–1710 (1993).

Seymour et al., *Polymer Chemistry,* Chapters 7–11, pp. 193–359, Dekker, New York, (1981).

Shibayama et al., "Volume phase transition and related phenomena of polymer gels" *Advances in Polymer Science,* vol. 109, Springer–Verlag Berlin Heidelberg, pp. 1–62 (1993).

Shield et al., "Enzymes in reversed micelles as catalysts for organic–phase synthesis reactions" *Ind. Eng. Chem. Fundam., 25:*603–612 (1986).

Shimada et al., "Footprint catalysis, X. –Surface modification of molecular footprint and its effects on their molecular recognition and catalysis" *Bull. Chem. Soc. Jpn., 67:*227–235 (1994).

Smith et al., "Ordered poly(p–phenylenevinylene) matrix nanocomposites via lyotropic liquid–crystalline monomers" *J. Am. Chem. Soc., 119:*4092–4093 (1997).

Sperling, L. H., "Introduction to polymer science" *Introduction to Physical Polymer Science,* John Wiley and Sons, New York, Chapter 1, pp. 1–21 (1986).

Sperling, L.H., Solution and phase behavior *Introduction to Physical Polymer Science,* John Wiley and Sons, New York, Chapter 4, pp. 97–121 (1986).

Takeuchi et al., "Molecular imprinting: an approach to "tailor–made" synthetic polymers with biomimetic functions" *J. Acta Polymer, 47:*471–480 (1996).

Tan, Y. Yong, "The synthesis of polymers by template polymerization" *Progress in Polymer Science 19:*561–588 (1994).

Tirrell, Matthew, "Fundamentals of polyemr solutions" *Interactiosn of Surfactants with Polymers and Proteins,* E.D. Goddard and K.P. Ananthapadmanabhan, eds., CRC Press; Boca Raton, Chapter 3, pp. 59–122 (1992).

Vlatakis et al., "Drug assay using antibody mimics made by molecular imprinting" *Nature, 361:*645–647 (1993).

Wharton et al., "Structure, function, and antigenicity of the hemagglutinin of influenza virus" *The Influenza Viruses,* Krug, Robert M., ed., Plenum Press, New York, Chapter 3, pp. 153–173 (1989).

Whitesides et al., "Molecular self–assembly and nanochemistry; A chemical strategy for the synthesis of nanostructures" *Science, 254:*1312–1319 (1991).

Williams, D.H., "The molecular basis of biological order" *Aldrichimica Acta,* vol. 24, pp. 71–80 (1991).

Wulff, Günter, "Molecular imprinting in cross–linked materials with the aid of molecular templates—a way towards artificial antibodies" *Angew. Chem. Int. Ed. Engl., 34:*1812–1832 (1995).

Yoshikawa et al., "Enantioselective electrodialysis of amino acids with charged polar side chains through molecularly imprinted polymeric membranes containing DIDE derivatives" *Polymer Jornal, 29:*205–210 (1997).

Zhao et al., "Soft lithographic methods for nano–fabrication" *J. Mat. Chem., 7:*1069–1074 (1997).

Kamiya, N. and Goto, M. (1998). "Preparation of surfactant–coated lipases utilizing the molecular imprinting technique" *Journal of Fermentation and Bioengineering* 85(2):237–239.

Kempe, M. and Mosbach, K. (Mar. 3, 1995). "Molecular imprinting used for chiral separations" *Journal of Chromatography A,* 694(1):3–13.

Murata, M. et al., (1996). "Template–dependent selectivity in metal adsorption on phosphoric diester–carrying resins prepared by surface template polymerization technique" *Bulletin of the chemical society in Japan* 69(3):637–642.

Piletsky, S.A. et al., (1998). "The rational use of hydrophobic effect–based recognition in molecularly imprinted polymers" *Journal of Molecular Recognition* 11(1–6):94–97.

Zhu, X.X. et al., (1997). "Pore size control in cross–linked polymer resins by reverse micellar imprinting" *Macromolecules* 30(10):3031–3035.

Protect
Add spacer
Add reactive functionalitiy

R = H or CH₃. The polymerizable group may
be attached at any point along the tail structure PG = Polymerizable Group

• Medium Polarity    • Low to No Polarity

Compound 1

Compound 2

Compound 3

Substituted Dextrans

OR = OH, $O_2CC_{15}H_{31}$,
$O_2CCH=CH_2$, $OSO_3^-$,
$O_2CNH(CH_2)_6NH_3^+$,
$O_2CNH(CH_2)_6$-aromatics Dextran Repeat Unit
MW = 5 - 40k Substituted Dextran
OR = OH, $O_2CC_{15}H_{31}$, $O_2CCH=CH_2$ Carbohydrate based reactive surfactants Dextran Repeat Unit
MW = 5 - 40k OR = OH, $O_2$C-imidazole $OR_1$ = OH, $O_2CNHC_6H_{12}NH_2$ $OR_2$ = OH, $O_2$C-$SO_3^-$ Addition of polar headgroups to polysaccharides Formula 6

OR = O(CH$_2$)$_{11}$O$_2$CCH=CH$_2$

Exemplary Compounds 11 and 12

Secondary and Tertiary Amine Formation

MOLECULAR COMPOUNDS HAVING COMPLEMENTARY SURFACES TO TARGETS

CROSS REFERENCE TO RELATED APPLICATIONS

This application is a continuation of U.S. patent application Ser. No. 09/172,921, filed Oct. 14, 1998 now abandoned, which claims the benefit of U.S. provisional patent application Ser. No. 60/061,805, filed Oct. 14, 1997, and U.S. provisional patent application Ser. No. 60/103,616, filed Oct. 9, 1998, the disclosures of which are incorporated herein by reference in their entirety.

STATEMENT OF RIGHTS TO INVENTIONS MADE UNDER FEDERALLY SPONSORED RESEARCH

This invention was made with government support under Grant Number N65236-98-1-5404 awarded by the Space and Naval Warfare Systems Command Systems Center Charleston. The government has certain right in the invention.

TECHNICAL FIELD

This invention relates to soluble molecular structures that are capable of specifically recognizing target molecules, and methods for their synthesis.

BACKGROUND ART

Biologically active macromolecules are complex entities which have intricate three dimensional structures. The exact spatial conformation of these macromolecules is directly related to their biological function. For example, proteins are composed of amino acids in well defined sequences. Amino acids may have both polar and nonpolar side groups. The polar side groups may in turn be either charged or uncharged in aqueous buffers near neutral physiological pH.

The three dimensional structure of a particular polypeptide chain depends on the multiple spatially specific interactions of its unique sequence, or primary structure. The chain folds into a three dimensional structure in accordance with the multitude of specific interactions among the constituent amino acid units. For example, there are $10^{26}$ possible primary structures for a 20 amino acid polypeptide. The secondary, tertiary, and quaternary structural possibilities increase the complexity.

The human immune system is impressive in its ability to generate and screen approximately $10^{12}$ antibody molecules in order to identify one that specifically recognizes and binds a foreign pathogen (A. Nisonoff, J. E. Hopper, S. B. Spring, "The Antibody Molecule", Academic Press, New York, 1975). The large number of trials is necessitated by the equally large number of sequences available through the twenty or so essential amino acids. For each invading foreign pathogen, there is perhaps only one (or at best a few) optimal backbone sequence that offers the potential for specific ligand-receptor, "lock-and-key" docking or "induced fit" docking. FIG. 1a illustrates lock-and-key docking wherein the active site of an enzyme is complementary in shape and electronic force field to that of the substrate. FIG. 1b illustrates induced fit docking wherein the active site of an enzyme has a shape complementary to that of the substrate only after the substrate is bound. Upon binding the active site of the enzyme is slightly distorted to accommodate the fit.

Combinatorial chemistry seeks to mimic the natural function of the immune system. It too involves examining large compound libraries to find the unique compound for binding to a target molecule (S. P. A. Fodor, et al., *Science*, 251, 767, 1991). In combinatorial chemistry compound libraries are designed and synthesized. The libraries comprise a large number of macromolecules produced via the combination of a variety of monomer precursors. The libraries are screened for new drugs, for example, antagonists of a specific receptor target. The ability to generate large, random compound libraries is important in combinatorial chemistry because the greater the diversity the more likely the library will include all possible monomer combinations that could react with or bind the target.

A great deal of effort is being spent on the application of these combinatorial libraries, as well as libraries of small organic molecules, for the discovery of new drugs (B. A. Bunin, M. J. Plunkett, J. A. Ellman, *Proc. Natl., Acad. Sci., U.S.A.*, 91, 4708, 1994). Libraries may ranging in size and can include, for example, from 100,000 to 500,000 compounds per library.

Despite its power, combinatorial chemistry suffers from several intrinsic weaknesses. First, it is a statistical approach. For example, a shot-gun or hit-or-miss approach is used for material discovery. Hundreds of thousands of compounds must be synthesized and screened to find a compound that may react with or bind the target. While combinatorial chemistry involves single-chain synthesis, the chain building process is inefficient. Even if the synthetic yield of attaching one repeat unit to a growing chain is 99%, the composite yield of growing a chain consisting of ten repeat units is only 90.4%, of twenty repeat units is only 82.6% and of thirty repeat units is only 75.5%.

The inefficient chain building process restricts single chains to be individually synthesized with limited chain lengths. Therefore, the three dimensional topography of the resulting coils can only be empirically sampled by studying the binding behavior with probe molecules. Binding requiring the coordinated interaction with more than ten repeat units is very difficult to establish because of the chain building inefficiency described above.

Additionally, unencumbered folding is not achieved because the chains are attached at one end to a substrate during synthesis. The lack of precise knowledge of coil conformation dependence on chain sequence precludes accurate prediction of folding pathways and biologically active site topography, where folding occurs in the test macromolecules.

Finally, the three dimensional structure of the folded proteins is held together by primarily nonbonded interactions. Hence, such a structure is delicate and susceptible to thermal and non-aqueous solvent induced denaturing. Peptide linkages also are susceptible to biological degradation in vivo through the intervention of digestive enzymes, for example, protease and chymotrypsin. Therefore, combinatorial chemistry is disadvantageous in terms of the time, money and effort required to produce the libraries and test them.

Whereas combinatorial chemistry and the immune system rely on a "shotgun" approach to find complements to targets, molecular imprinted polymers (MIPs) rely on a semi-directed method of forming recognition sites. See (a) Mosbach, K., *Trends Biochem. Sci.*, 19:9–14 (1994), (b) Wulff, G., *Angew. Chem. Int. Ed. Engl.*, 34:1812–1832 (1995) (c) Mosbach, K. and Ramström, O; *Biotechnology*, 14:163–170 (1996) and (d) Takeuchi, T. and Matsui, *J. Acta Polymer*, 47:471–480 (1996). MIPs are fabricated by polymerizing monomers (e.g., acrylic acid) and cross-linking molecules (e.g., ethylene glycol diacrylate) in the presence of an "imprinting molecule" to produce a large, rigid, and insoluble polymer structure. A nonsolvent (e.g., chloroform) "porogen" is employed during polymerization to produce large pores in the bulk material. The porogen is required to allow target diffusion into the insoluble MIP's inner regions, where the large percentage of the imprints are located. MIP structures must be rigid to achieve target recognition. This rigidity is achieved by employing crosslinking molecules that have a high number of crosslinking moieties per molecular weight. Both bulk and suspension polymerization schemes have been employed. Bulk polymerization produces a rigid plastic product the size of the reaction container, while a polymeric sphere on the order of a micrometer in size (a microsphere) is formed through suspension polymerization.

The resulting MIP is a porous macroscopic solid, which is not soluble and due to its size it settles out of solution. The porous nature of the MIP structure produces diffusional resistance, reducing separation efficiency. Each MIP has many imprint sites ($10^{23}$) with widely varying degrees of binding affinity with only a small fraction of sites accessible to targets. The use of the porogen in the synthesis procedure results in large voids throughout the structure. The voids are intended to allow for diffusion of target molecules into and out of the imprinted sites. However, many sites are still inaccessible.

MIPs have been used in chromatography (O'Shannessy, D. J, et al., *Journal of Molecular Recognition*, 2:1–5 (1989); Fischer, L., et al., PCT WO 93/09075; and Yoshikawa et al., *Polymer Journal*, 29:205–210 (1997)), as artificial antibodies (Arshady, R. and Mosbach, K., *Makromol. Chem.*, 182:687–692 (1981); Ekberg, B., Mosbach, K. *Tibtech*, 7:92–96 (1989); Mosbach, K., U.S. Pat. No. 5,110,833; Vlatakis, G., et al., *Nature*, 361:645–647 (1993); Glad, M., et al., PCT WO 93/05068; Shimada, T., et al., *Bull. Chem. Soc. Jpn.* 67:227–235 (1994); Mosbach, K., PCT WO 94/11403; Kriz, et al., *Anal. Chem.* 67:2142–2144 (1995); Yan, M. Y., et al., U.S. Pat. No. 5,587,273; Haupt, K., et al., 213th ACS National Meeting Abstracts, Section I&EC, 1997, No. 32; and Mosbach, K., et al., PCT WO 97/22366), and as artificial enzymes (Wulff, G., et al., U.S. Pat. No. 4,127,730; Kempe, M. and Mosbach, K. *Analytical Letters*, 24:1137–1145 (1991); and Tanaka, T., et al., PCT WO 94/26381).

MIP's used for chromatography are often used for separating chiral isomers. An important property of biologically active compounds is their stereochemistry. For example, most of the essential amino acids are chiral, having L- and D-isomers. However, only the L-isomers are found in proteins. In general, biological activity implies optically specific interactions. A docking site (active, catalytic, or regulatory site) is commonly defined by multiple interaction points (force fields) that are inherently asymmetric (optically active). Pharmaceuticals, agrochemicals, flavors, and fragrances contain many naturally occurring or synthetic stereoisomers. There has been much attention given to the development of methods for separating isomers, among them MIP's and enzymatic kinetic resolution. There is an important need in the field for effective methods of resolving chiral isomers. There is a need for efficient methods for producing molecules which are capable of interacting with specific targets. There further is a need for the development of molecules capable of binding specifically with target compounds which can be used to separate the target compounds, or which can be used as synthetic antibody or enzyme mimics or any of a variety of applications where specific interaction with a target molecule occurs. There also is a need for improved methods for isolating and purifying optical isomers, and for improved affinity materials that preferentially interact with a desired isomer.

DISCLOSURE OF THE INVENTION

Synthetic polymer complements (SPCs) are provided, and monomers useful in forming the SPCs, as well as methods for their synthesis and use. In one embodiment, the SPCs have surfaces that include functional groups that are complementary to surface sites of targets such as nanostructures or macromolecular targets, and they are capable of specifically interacting with such targets. In one embodiment, the positions of the functional groups are stabilized by a thin, soluble polymer network. The SPCs may be formed by contacting the target with a set of monomers which self-assemble on the target and then are polymerized into a network to form the SPC. The monomers preferably include surfactant monomers. In one embodiment, at least a portion of the surface of the resulting SPC is thus complementary to at least a portion of the target. The complex of the SPC and the target may be the desired product. Alternatively, the target is released and the SPC isolated for use in different applications.

Provided are monomers capable of forming SPCs and SPCs formed from the monomers as well as composition comprising the monomers and/or SPCs and methods for their synthesis and use.

In one embodiment, there is provided a set of monomers capable of self assembling and forming a synthetic polymer complement "SPC" capable of binding a target, wherein the SPC has a diameter, for example, less than about 1000 nm, and wherein at least some of the monomers comprise: at least one head group capable of undergoing a binding interaction with the target; and at least one crosslinking group capable of covalently reacting to crosslink monomers of the monomer set, thereby to form the SPC, wherein head groups in the SPC are capable of a binding interaction with the target.

In one embodiment, at least some of the monomers (a portion of the monomer population) comprise a head group, a crosslinking group and a tail region. In another embodiment, the set of monomers further comprises some monomers comprising a crosslinking group, such as acrylamide. The set of monomers also may comprise a cosurfactant. In one embodiment, some of the monomers comprise styrene, divinylbenzene and vinylbenzoic acid, and the monomer set further comprises a cosurfactant.

In one embodiment, in the set of monomers, in at least some of the monomers, the head group is covalently attached to the tail region. In at least some of the monomers, the crosslinking group may be covalently attached to the tail region. At least some of the monomers may be amphiphilic.

In another embodiment, in the set of monomers, at least a portion of the monomers comprise a carbohydrate moiety, such as a dextran moiety. The tail group may be covalently attached to the carbohydrate moiety. The set may include, for example, about 10 to 10,000 monomers. The monomer set may include, for example, at least about 2 to 50 different types of monomers, e.g., 5–20. In one embodiment, the set of monomers is capable of forming an SPC which is capable of binding about 1 to 20 targets, for example 1 to 20 molecules of the target.

The tail region may comprise, e.g., a polymeric moiety such as a poly(ethylene glycol), poly(ethylene oxide), poly(vinyl alcohol), poly(vinylpyrrolidone), poly(ethyloxazoline), poly(ethylene oxide)-co-poly(propyleneoxide) block copolymer, polysaccharide or a poly(amino acid) moiety. The tail region also may comprise a branched or straight chain saturated or unsaturated hydrocarbon moiety. Exemplary head groups include alcohols, carboxylic acids, amides, amines, phosphates, sulfonates, aromatic groups, sugars, disaccharides and polysaccharides.

Exemplary crosslinking groups include acrylate, methacrylate, acrylamide, vinyl ether, epoxide, methacrylamide, vinylbenzene, α-methylvinylbenzene, divinylbenzene, maleic acid derivative, diene, substituted diene, thiol, alcohol, amine, carboxylic acid, carboxylic anhydride, carboxylic acid halide, aldehyde, ketone, isocyanate, succinimide, carboxylic acid hydrazide, glycidyl ether, silane, siloxane, chlorosilane, alkoxysilane, alkyne, azide, 2'-pyridyldithiol, phenylglyoxal, iodo, maleimide, aryl halides, imidoester, dibromopropionate, and iodacetyl.

The target may be any of a range of materials, including biological molecules, such as an enzyme, such as chymotrypsin.

Also provided are synthetic polymer complements ("SPCs") having a diameter less than about 1000 nm and capable of binding a target, wherein the SPC is formed by: providing a set of monomers, at least some of the monomers comprising at least one head group capable of undergoing a binding interaction with the target, and at least one crosslinking group capable of covalently reacting to crosslink monomers of the monomer set; and contacting the set of monomers with a target to permit the monomers to self assemble on the target. Preferably, monomers of the monomer set then are crosslinked to form the SPC, wherein head groups in the SPC are capable of a binding interaction with the target. In one embodiment, at least some of the monomers include a head group, a crosslinking group and a tail region.

The synthetic polymer complement optionally further comprises the target which may be associated with the SPC via binding interactions between the head groups of the SPC and substituents on the target. The SPC and the target may be covalently linked. The SPC is preferably capable of specifically binding the target.

Also provided is synthetic polymer complement formed from a set of monomers, wherein some of the monomers comprise styrene, divinylbenzene, and vinylbenzoic acid, and wherein the monomer set further comprises a cosurfactant.

In one embodiment, there is provided a composition comprising an SPC, and optionally the target, in a pharmaceutically acceptable carrier, wherein the target is an active agent, as well as methods of administering the composition in different therapeutic applications.

Also provided is a method of making a synthetic polymer complement ("SPC") capable of binding a target, the method comprising: providing a set of monomers, wherein at least a portion of the monomers comprises at least one head group capable of undergoing a binding interaction with the target, and at least one crosslinking group, capable of covalently reacting with at least one of the crosslinking group of another of said monomers and a crosslinking agent; and contacting the monomers with a target to permit the monomers to self assemble on the target via binding interactions between the head group and the target, thereby to form the synthetic polymer complement. The method may further comprise reacting the crosslinking groups of the monomers, thereby to covalently crosslink the monomers after assembly, for example, in the presence of a crosslinking agent.

In a further embodiment, a method is provided of making a synthetic polymer complement ("SPC") having a diameter less than about 1000 nm, wherein the SPC is capable of binding a target, the method comprising:

providing a set of monomers, wherein at least some of the monomers comprise at least one head group capable of undergoing a binding interaction with the target, and at least one crosslinking group capable of covalently reacting to crosslink the monomers, thereby to form the synthetic polymer complement;

contacting the set of monomers with a target to permit the monomers to self assemble on the target; and preferably reacting the crosslinking groups of the monomers, thereby to covalently crosslink monomers of the monomer set, to form SPCs having an average diameter less than about 1000 nm, wherein head groups in the SPC are capable of a binding interaction with the target.

In one embodiment, an aqueous solution comprising the target, such as an enzyme, may be contacted with an organic solvent comprising a cosurfactant, thereby to form a reverse micelle having the target, such as an enzyme, solubilized therein; and the set of monomers may be contacted with the target, such as an enzyme in the reverse micelle, to permit the monomers to self assemble on the target.

In another embodiment, the set of monomers comprises some monomers that comprise at least one crosslinking group capable of covalently reacting to crosslink the monomers, thereby to form the synthetic polymer complement, and at least some other monomers that comprise at least one head group capable of undergoing a binding interaction with the target, and the set of monomers further comprises a cosurfactant; the set of monomers is contacted with the target to permit the monomers to self assemble on the target in an oil in water emulsion; and the crosslinking groups of the monomers are reacted, thereby to covalently crosslink monomers to form SPCs having a diameter of about 5 nm to 400 nm, wherein head groups in the SPC are capable of a binding interaction with the target, and wherein the SPC comprises about 1 to 1000 binding sites for the target. For example, the monomers comprising at least one crosslinking group may comprise styrene, the monomers comprising at least one head group may comprise vinyl benzoic acid and divinylbenzene, and the surfactant may be hexadecyltrimethylammonium bromide.

The method may further comprise releasing the target from the SPC. In another embodiment, the method may further comprise covalently linking the target to the SPC.

In one embodiment, the target is an active agent, such as pharmaceutical or diagnostic agent, and the SPC is capable of binding the active agent.

The method may be used to produce SPCs that are capable of binding to molecules, such as enzymes by binding to specific groups, such as polar or charged groups, thereby to stabilize them in conditions such as organic solvents and elevated temperatures. Monomers may be selected in the monomer set, such that after assembly and formation of the SPC the head groups of the SPC are oriented such that binding of the SPC to the target is promoted, for example, by specific binding between the head groups of the SPC and functional groups on the target.

In another embodiment monomer compounds having the following structures are provided, as well as SPCs formed therefrom and compositions comprising the monomer compounds or SPCs formed therefrom, as well as methods of use thereof:

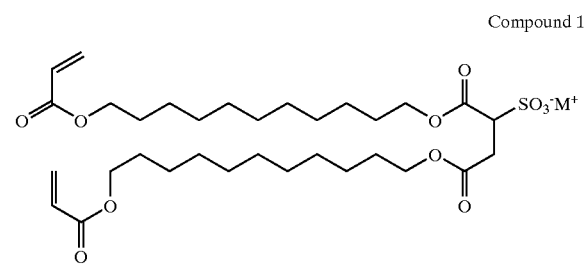

Compound 1 wherein $M^+$ is a cation.

Compound 2

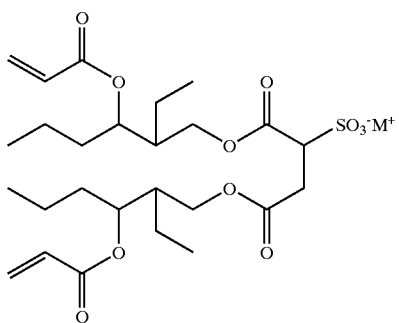

wherein M⁺ is a cation.

Compound 3

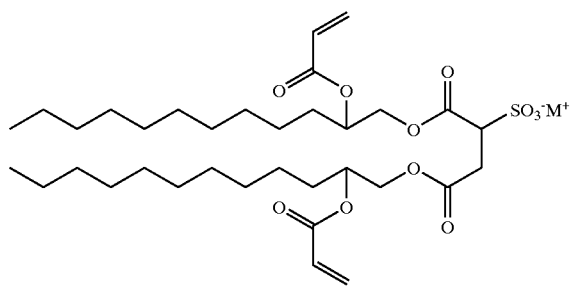

wherein M⁺ is a cation.

Compound 11

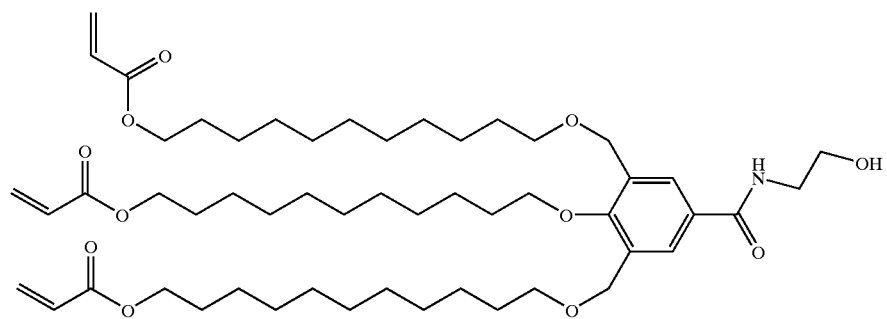

Compound 12

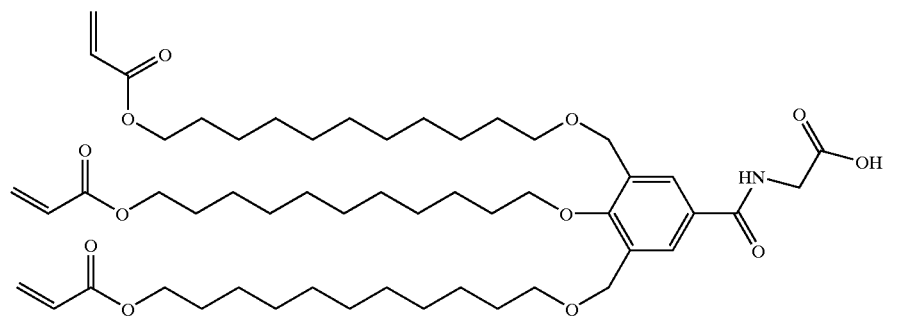

or salts thereof.

MODES FOR CARRYING OUT THE INVENTION

Figure 1A:
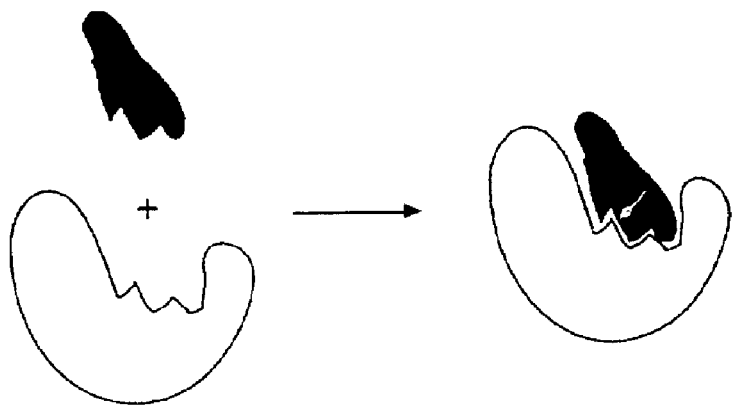
FIG. 1a is a schematic diagram of the "lock-and-key" model of interaction of substrates and enzymes.
Figure 1B:
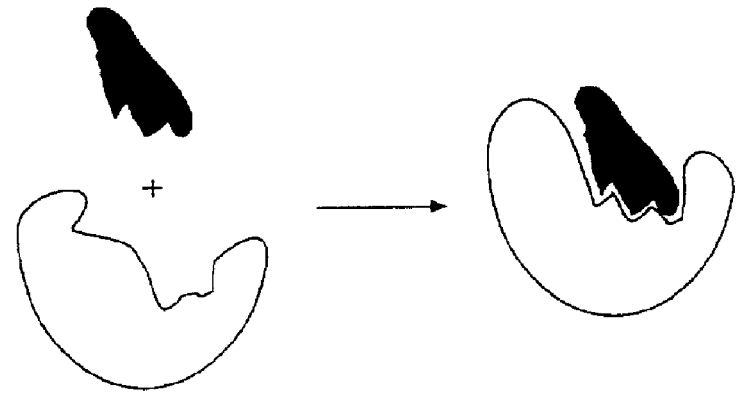
FIG. 1b is a schematic diagram of the "induced fit" model.

Synthetic polymer complements (SPCs), that in one embodiment are capable of specifically interacting with a target, are provided, and methods of making the SPCs. The surface of the SPC in one embodiment includes functional groups that are complementary to sites on a target. To form the SPC, the target is combined with a set of monomers which associate with the target by binding interactions between head groups on the monomer and complementary sites on the target. Assembly is also encouraged by favorable interactions between the monomer tail regions. The monomers self-assemble spontaneously on the target at different complementary sites on the target. Subsequently, reactive groups on the monomers are optionally crosslinked, thus forming the synthetic polymer complement (SPC). The resulting SPC contains a plurality of functional groups on its surface which specifically recognize and bind to the target. Monomers may be selected and used at specific concentrations to permit the desired number of head groups to be incorporated into the SPC to adjust the binding affinity of the SPC for the target. The SPC may be formed as a thin layer of the crosslinked monomers around the target. SPC's may also be formed through the polymerization of micelle and reverse micelle structures, optionally either or both of the inside contents or external shell of the micelle or reverse micelle. This thin layer can serve to stabilize and protect the target, for example, in the embodiment wherein the target is an enzyme. SPCs may be formed as a polymerized network with high thermal and solvent stability. SPCs capable of interacting with any of a wide range of different targets may be designed and synthesized.

Targets

Synthetic polymer complements may be formed with a binding affinity, for example with a specific binding affinity, for any of a variety of targets. A target may range in size from a small molecule, e.g., with a size less than 1 nm, to a microstructure such as a whole cell on the order of micrometers in size. The target may be a molecule, or a portion of a molecule, such as the Fc region or the epitope portion of an antibody. The target may be a complex biological structure such as a virus or a portion of a virus, a bacterium or a portion of a bacterium, a eukaryotic cell surface or a portion of a eukaryotic cells surface. The target also may be an inorganic nanostructure or a microstructure.

The target may be a natural or synthetic molecule or structure. Examples include organic compounds, toxins, pollutants, synthetic drugs, steroids and derivatives, proteins, glycoproteins, polysaccharides, lipids, lipopolysaccharides, polyanions, including nucleic acids, porphyrins and substituted porphyrins. Biological molecules which function as cellular receptors, antibodies, antigens, cytokines, and enzymes may be targets.

The target may be any of a range of different synthetic or naturally occurring polymers, including proteins such as enzymes and antibodies and glycoproteins. The terms "protein", "polypeptide", and "peptide" are used interchangeably herein to refer to polymers of amino acids of any length. The polymer target may be polar or nonpolar, charged or uncharged. The polymer target may be linear, branched, folded, or aggregated. It may comprise modified amino acids, and it may be interrupted by non-amino acids. It also may be modified naturally or by intervention; for example, disulfide bond formation, glycosylation, myristylation, acetylation, alkylation, phosphorylation or dephosphorylation. Also included within the definition are polypeptides containing one or more analogs of an amino acid (including, for example, unnatural amino acids) as well as other modifications known in the art.

The target may be any of a variety of active agents, including pharmaceutical agents, biological modifiers, or diagnostic agents. Pharmaceutical agents include, but are not limited to, antipyretic and antiinflammatory drugs, analgesics, antiarthritic drugs, antispasmodics, antidepressants, antipsychotics, antineoplastics, antiangiogenics, angiogenics, neurotransmitters, antimicrobials, tranquilizers, antianxiety drugs, narcotic antagonists, antiparkinsonism agents, cholinergic agonists, chemotherapeutic drugs, immunosuppressive agents, antiviral agents, antibiotic agents, parasiticides, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs, opioids and vitamins. Detailed parameters and discussions of such active agents can be found, for instance, in the Physician's Desk Reference (1995) 49th ed., Medical Economics Data Production Co. New Jersey.

The chemical structures of active agents, include, but are not limited to, lipids, organics, proteins, synthetic peptides, natural peptides, peptide mimetics, peptide hormones, steroid hormones, D amino acid polymers, L amino acid polymers, oligosaccharides, polysaccharides, nucleotides, oligonucleotides, nucleic acids, protein-nucleic acid hybrids, antigens and small molecules, as well as cells, tissues, cell aggregates, cell fragments. Combinations of active agents may be used. Saccharides, including polysaccharides, such as heparin, can also be administered.

Proteins may be obtained, for example, by isolation from natural sources or recombinantly. Exemplary proteins include, but are not limited to ceredase, calcitonin, erythropoietin, enzymes, biopharmaceuticals, growth hormones, growth factors, insulin, monoclonal antibodies, interferons, interleukins, collagen and cytokines. Enzymes include proteases, DNAses and RNAses.

Suitable steroid hormones include, but are not limited to, corticosteroids, estrogen, progesterone, testosterone and physiologically active analogs thereof. Suitable nucleic acids include, but are not limited to, DNA, RNA and physiologically active analogs thereof.

Specific examples of active agents are as follows. Non-steroidal anti-inflammatory agents include Aspirin, Ibuprofen, Alclofenac, Indomethacin, Mefenamic Acid, Flufenamic Acid, Sulindac, Piroxicam, Diclofenac, Diclofenac sodium, Tiaramide, Tolmetin, Phenylbutazone, and Naproxen; steroidal anti-inflammatory agents include Predonisolone, Triamcinolone, Dexamethasone, Beclometasone, and Hydrocortison; ataraxics include Chlorpromazine hydrochloride, Carbamazepine, Clonazepam, Phenitoin, Haloperidol, Chlordiazepoxide, Mexazolam, Amitriptyline hydrochloride, Imipramine hydrochloride, Flunitrazepam, and Triazolam; hypotensive diuretics include Furosemide, Ethacrynic acid, Bumetanide, Hydrochlorothiazide, Trichlormethiazide, Metolazone, and Chlortalidone; antihypertensive agents include Prazosin hydrochloride, Reserpin, Labetalol, Clonidine hydrochloride, Bunazocine hydrochloride, Captopril, Hydralazine hydrochloride, and Budralazine; cardiovascularagents include Theophyline, Etilefrine hydrochloride, Dobutamine hydrochloride, Quinidine sulfate, Lidocaine, Mexiletine hydrochloride, Digitoxin, Digoxine, Deslanoside, Vinpocetine, and Cinepazide maleate; coronary vasodilators include Diltiazem hydrochloride, Nifedipine, Verapamil hydrochloride, Nicardipine hydrochloride, Isosorbide dinitrate, and Nitroglycerine; sympathomimetic agents include Isoprenaline hydrochloride; peripheral muscle relaxants include Eperisone hydrochloride, and Dantrolene, Buclofen; ischemic heart disease agents include Dilazep dihydrochloride, Dipyridamole, and Nicorandil; beta-stimulants include Etilefrine hydrochloride, and Dobutamine hydrochloride; beta-blockers include Alprenolol hydrochloride, Propranolol hydrochloride, Oxprenolol hydrochloride, and Pindolol; antispamedics include Atoropin, and Scopolamine; antibiotics include Cefaclor, Cefalexin, Froxacine, Pipemidic acid, Sulfamethoxazolin sodium, Cefmenoxime hemihydrochloride, Cefoxitin sodium, Ceftizoxime sodium, Latamoxef sodium,Ampicillin, Sulbenicillin disodium, Benzylpenicillin potassium, Phenoxymethylpenicillin potassium, Chlortetracycline hydrochloride, Tetracycline hydrochloride, Minocycline hydrochloride, Doxycycline hydrochloride, Rifampicin, Erythromycin, and Clindamycin; antifungal agents include Griseofulvin, Nystatin, Amphotericin B, and Miconazole; chemotherapeutics include Nalidixic acid, Enoxarin, and Ozole; antivirotic agents include Vidarabine; antineoplastic agents include Methotrexate, Vindesine sulfate, Vincristine sulfate, and Daunorubicin hydrochloride; anti-ulcerous drugs include Cetraxate hydrochloride, Cimetidine, Famotidine, Pirenzepine hydrochloride, Ranitidine hydrochloride, and Sulpiride; antiallergic agents include Ketotifin, Tranilast, Azelastin, Chlorpheniramine maleate, Clemastine fumarate, and Mequitazine; expectorants include Ambroxolhydrochloride; vitamins include Calcitriol, Tocopherol, Tocopherol acetate, Tocopherol nicotinate, Riboflavine, Folic acid, Menadione, and Phytonadione; hepatonics include Malotilate, Glycyrrhizin; diabetic agents include Acetohexamide, Chlorpropamide, and Tolbutamide; hormones include Danazol, Levothyroxine, Liothyronine, and Propylthiouracil; asuricosuric agents include Probenecid; immunosuppressants include Azathioprine, and Cyclosporin; and antiemetics include Domperidone.

Provided in one embodiment are compositions comprising SPCs, and optionally a target, in a pharmaceutically acceptable carrier. Pharmaceutical carriers suitable for a particular route of administration may be used. Exemplary routes of administration include orally, parenterally, topically, by inhalation, by implantation, intravenously, mucosal delivery, dermal delivery, and ocular delivery. The SPC and/or target may be formulated into appropriate forms for different routes of administration as described in the art, for example, in "Remington: The Science and Practice of Pharmacy", Mack Publishing Company, Pennsylvania, 1995, the disclosure of which is incorporated herein by reference.

Monomers

In one embodiment, the monomer includes at least one head group, which is a functional group, capable of a preferably non-covalent, and preferably specific, binding interaction with a site on the target, and a crosslinking group, which is a reactive group, capable of undergoing a covalent reaction with another of the monomers or with crosslinking agents. The functional group capable of undergoing a binding interaction is referred to herein as the "head" group, while the reactive group, capable of undergoing a covalent reaction with another of the monomers or with crosslinking agent, is referred to herein as the "crosslinking group." The crosslinking group preferably permits crosslinking and/or polymerization of the monomers under certain conditions. Optionally each monomer may include more than one head or crosslinking group. The monomer also may include one or more tail regions. The monomer also may comprise at least one tail group and at least one crosslinkable group. The head group and the crosslinking group are optionally linked by the portion of the monomer referred to herein as the "linker" or "tail" on the monomer. Optionally the "head" may serve as the "tail" as well, or crosslinker functionalities and non-reactive solubilizing "tail(s)" may all be attached to the "head".

Figure 2A:
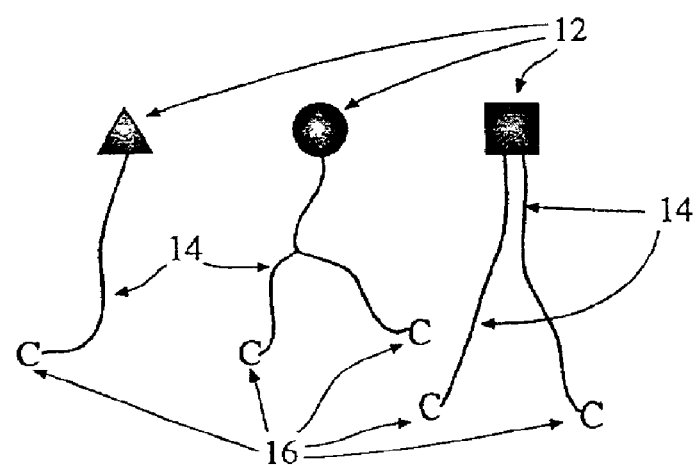
FIG. 2a is a schematic illustration of a set of monomers, wherein each monomer 28 includes a "head" 12, a linker or "tail" 14, and a crosslinking group 16.
Figure 2B:
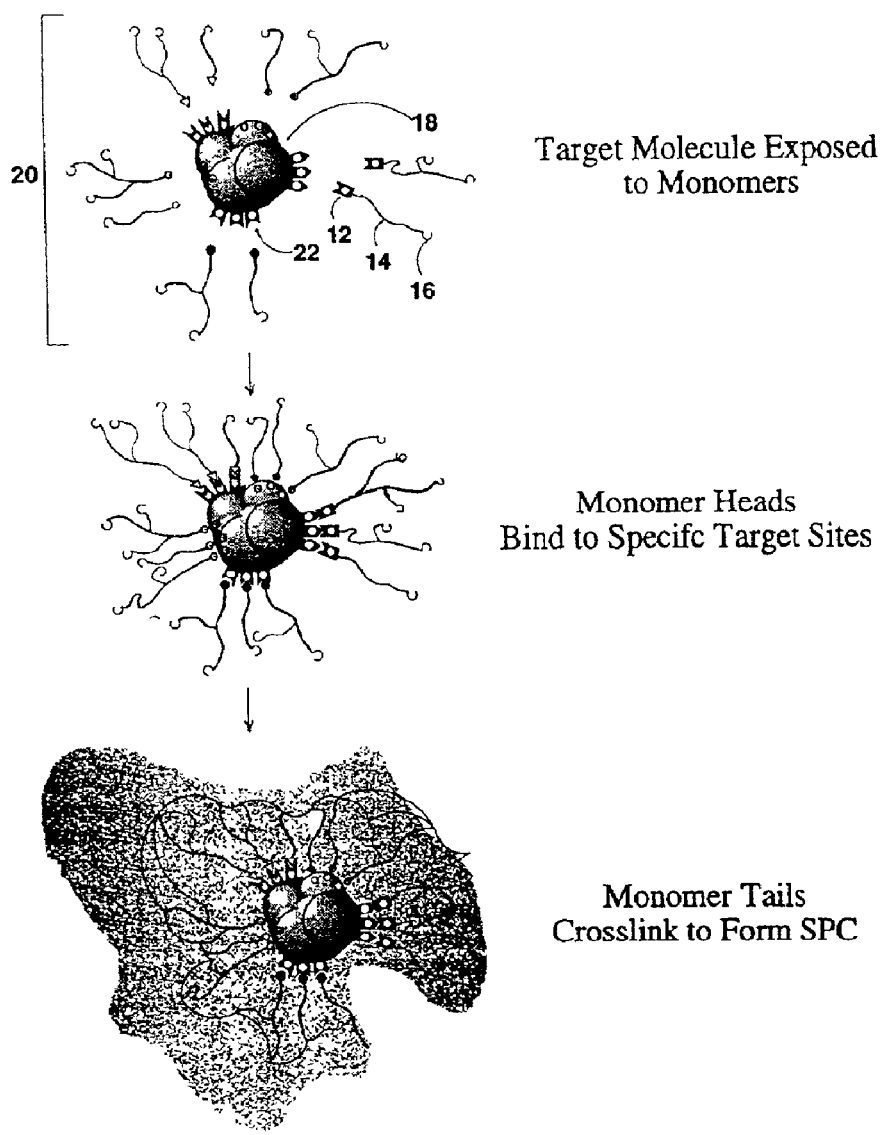
FIG. 2b is a schematic illustration of a set of crosslinkable monomers exposed to target 18 (top), assembled around and bound to target 18 (middle) and then crosslinked around the monomer to form a synthetic polymer complement (bottom).
Figure 2C:
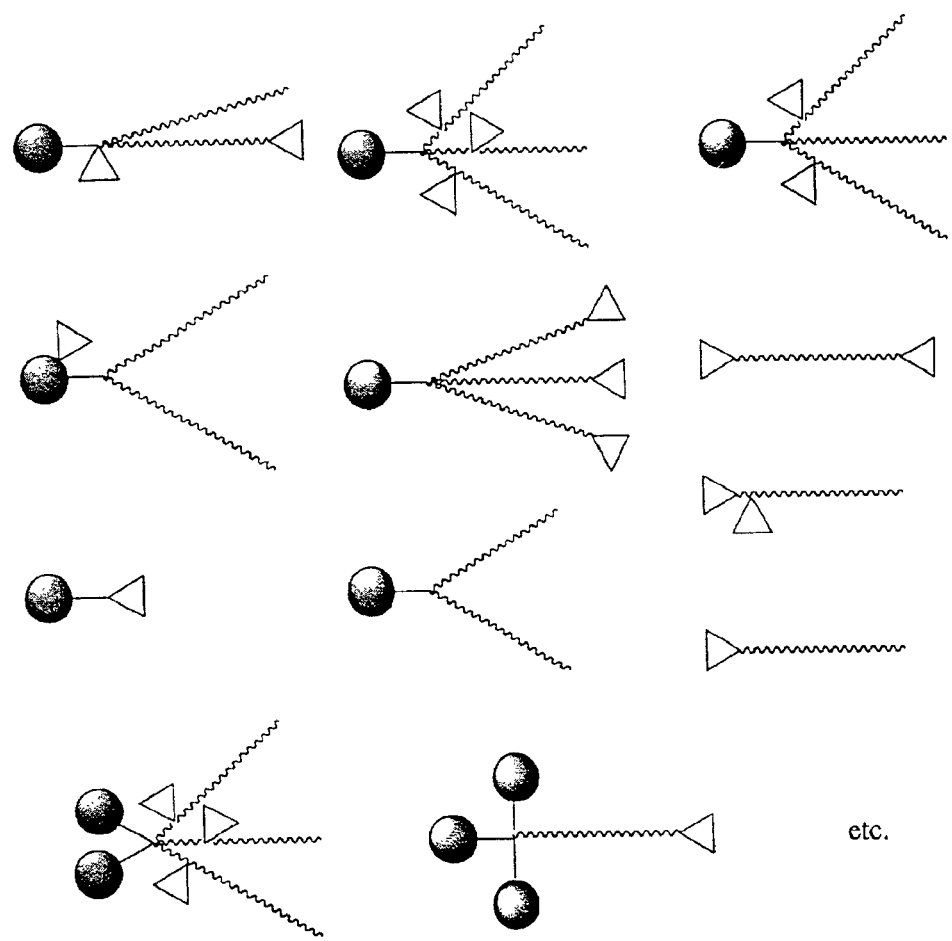
FIG. 2c is a schematic illustration of exemplary configurations of monomers including head groups, tails and crosslinking groups.

One embodiment is illustrated schematically in FIG. 2a. which depicts a set of monomers, each monomer 28 including the "head" 12, the linker or "tail" 14, and the crosslinking group 16. FIG. 2b is a schematic illustration of a set of crosslinkable monomers exposed to target 18 (top of FIG. 2b), assembled around and bound to target 18 (middle) and then crosslinked around the monomer to form an SPC (bottom). There are many potential arrangements of heads tails and crosslinking groups. Examples are shown in FIG. 2c. Monomers may include one or more of the head, tail and/or crosslinking groups. In one embodiment, monomers include one or two heads; one, two or three tails; and one, two, or three crosslinking groups. The monomer also may include one or more core regions, wherein the core region is a moiety to which one or more of the head, tail or crosslinking group are attached.

Tables 1–4 list exemplary head groups (Table 1), core regions (Table 2), tails (Table 3), and crosslinking groups (Table 4). In Tables 1–4, the groups are representative structures. Other possible structures are possible within the scope of the invention, for example, sugars other than glucose may be used. In these tables, R and $R_{1-5}$ represent possible points of attachment for other parts of the monomers; where multiple attachment points are possible, all possible combinations are included. In Table 3, n is 2–100, e.g. 4–20.

TABLE 1

Head Groups

Sulfonate
Carboxylate
Phosphate
Phosphonate
Carboxylic acid
Ammonium Salt
Amidine Salt
Amide
Alcohol
Phenol
Amine
Aromatic amine Sugar           Any of Disaccharide
Polysaccharide Aromatic ring Aliphatic group    R—CH₃

TABLE 2

Core Regions

Succinic ester

TABLE 2-continued

Core Regions

Succinic amide

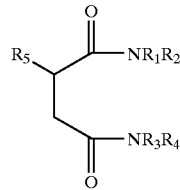

(poly)-Hydroxy substituted benzoic acid

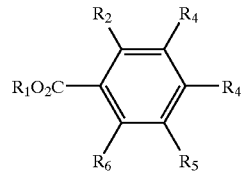

$R_2$–$R_5$ = independently H or OR, where R represent any tail (poly)-Alkyl substitued benzoic acid

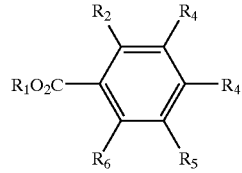

$R_2$–$R_5$ = independently H or any tail

Sugar
Disaccharide
Polysaccharide
Phosphate
Phosphonate
Any headgroup
Any tail
Any crosslinking group

TABLE 3

Tails

Aromatic groups
Aliphatic chains        $R_1$—$(CH_2)_n$—$R_2$

Branched aliphatic chains

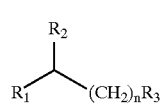

Unsaturated aliphatic chains

Polyethylene glycol chains

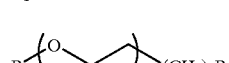

Polypropylene glycol chains

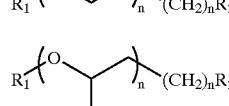

Polytetramethylene glycol chains

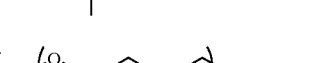

Other groups

TABLE 4

Crosslinking Groups

Acrylates
Acrylamides
Styrenics
Methacrylates
Methacrylamides
Fumaric esters and half esters
Maleic esters and half esters
Butadienics
Isoprenics
Alcohols
Amines
Carboxylic acids
Aldehydes
Thiols
Isocyanates In one embodiment, a monomer compound of Formula 1, below, is provided.

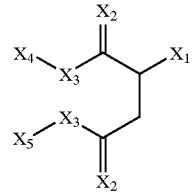

Formula 1

In Formula 1, in one embodiment:
$X_1$ is —$SO_3^-$, —$OSO_3^-$, $N(R)_3^+$, or —$P(OR)O_2^-$;
$X_2$ is O or S;
$X_3$ is —O—, —NH—, —NR— or —S—;
$X_4$ and $X_5$ are independently alkyl, for example saturated or unsaturated, straight chain, branched or cyclic, substituted or unsubstituted hydrocarbon, e.g., $CH_3$ $(CH_2)_n$—, where n is 3 to 100, for example 7 to 20; and optionally at least one of $X_4$ and $X_5$ are substituted with a moiety comprising a crosslinkable group, wherein the crosslinkable group is, for example, —CH=CH—, —CR=CR—, —$O_2$CCH=$CH_2$, —$O_2$CC($CH_3$)=$CH_2$, —NRC(O)CH=$CH_2$, —NRC(O)C($CH_3$)=$CH_2$, —C(=$CH_2$)—CH=$CH_2$, or —$C_6H_4$—CR=$CH_2$, wherein R is, for example, H, aromatic or alkyl, for example methyl, ethyl, propyl or phenyl.

In another embodiment, there is provided a carbohydrate monomer that comprises a carbohydrate region, comprising plural hydroxyl groups, wherein at least one hydroxyl group is modified to include at least one crosslinkable group. In another embodiment, at least one of the hydroxyl groups is modified to include at least one tail group. In a further embodiment, at least one of the hydroxyl groups is modified to include at least one crosslinkable group and at least one tail group. The carbohydrate monomer also may comprise at least one head group.

The carbohydrate region of the carbohydrate monomer may include a carbohydrate or carbohydrate derivative. For example, the carbohydrate region may be derived from a simple sugar, such as glucose, ribose, arabinose, xylose, lyxose, allose, altrose, mannose, gulose, idose, galactose, fructose or talose; a disaccharide, such as maltose, sucrose or lactose; a trisaccharide; or a polysaccharide, such as cellulose, glycogen and dextran; or modified polysaccharides, such as methylcellulose and hydroxymethyl cellulose. Other carbohydrates include sorbitan, sorbitol, and glucosamine. The carbohydrate may include amine groups in addition to hydroxyl groups, and the amine or hydroxyl groups can be modified to include a crosslinking group, a tail group, a head group, or combinations thereof.

In one embodiment, the carbohydrate monomer can be a compound of any of Formulas 2, 3 and 4:

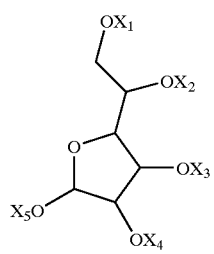

Formula 2

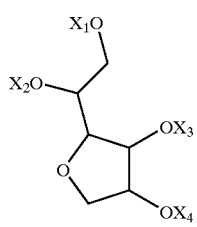

Formula 3

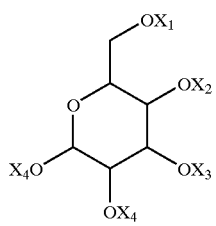

Formula 4

In one embodiment, in the carbohydrate monomers of Formulas 2, 3 and 4, $X_{1-5}$ independently are at least one of H, a moiety comprising a head group, a moiety comprising a tail group a moiety comprising a crosslinking group.

In one embodiment at least of $X_{1-5}$ is a moiety comprising further carbohydrate groups including carbohydrate polymers, such as dextran or cellulose.

In another embodiment, in Formulas 2, 3 and 4:

$X_{1-5}$ are independently H or alkyl for example saturated or unsaturated, straight chain, branched or cyclic, substituted or unsubstituted hydrocarbon, e.g., $CH_3(CH_2)_n$—, where n is 7 to 20; and optionally at least one of $X_{1-5}$ comprises a moiety comprising a crosslinkable group, wherein the crosslinkable group is, for example, —CH=CH—, —CR=CR—, —O$_2$CCH=CH$_2$, —O$_2$CC(CH$_3$)=CH$_2$, —NRC(O)CH=CH$_2$, —NRC(O)C(CH$_3$)=CH$_2$, —C(=CH$_2$)—CH=CH$_2$, or —C$_6$H$_4$—CR=CH$_2$, wherein R is H, aromatic or alkyl, for example methyl, ethyl, propyl or phenyl.

In another embodiment, a monomer compound of Formula 5 is provided:

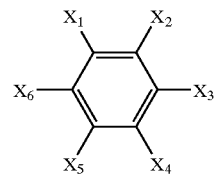

Formula 5

In one embodiment, in Formula 5, $X_{1-6}$ independently are at least one of H, a moiety comprising a head group, a moiety comprising a tail group and a moiety comprising a crosslinking group.

In one embodiment of Formula 5:
at least one of $X_{1-6}$ is H;
at least one of $X_{1-6}$ comprises a moiety comprising a head group;
at least one of $X_{1-6}$ comprises a moiety comprising a tail group; and
at least one of $X_{1-6}$ comprises a moiety comprising a crosslinking group.

In another embodiment, in Formula 5:
at least one of $X_{1-6}$ is H;
at least one of $X_{1-6}$ is a moiety comprising a tail group, such as alkyl, for example a saturated or unsaturated, straight chain, branched or cyclic, substituted or unsubstituted hydrocarbon, e.g., $CH_3(CH_2)_n$—, where n is 7 to 20; and
at least one of $X_{1-6}$ comprises a moiety comprising a head group, for example, alcohol, carboxylic acid, amide, amine, phosphate, or sulfonate; and
the compound of Formula 5 comprises a crosslinkable group, for example, —CH=CH—, —CR=CR—, —O$_2$CCH=CH$_2$, —O$_2$CC(CH$_3$)=CH$_2$, —NRC(O)CH=CH$_2$, —NRC(O)C(CH$_3$)=CH$_2$, —C(=CH$_2$)—CH=CH$_2$, or —C$_6$H$_4$—CR=CH$_2$, wherein R is H, alkyl, or phenyl, for example, methyl, ethyl, propyl, or phenyl, wherein the crosslinkable group is, for example, substituted on the tail group.

Figure 19A:
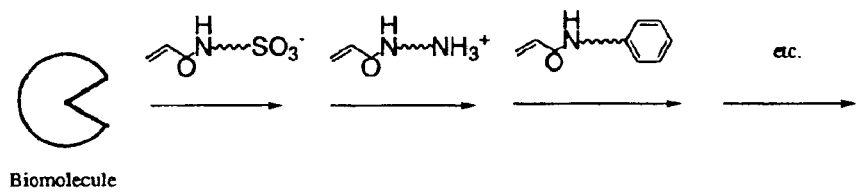
FIG. 19a is a schematic illustration of the titration of a biomolecule with monomers with various head group functionality.
Figure 19B:
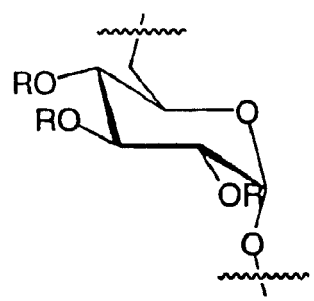
FIG. 19b is a schematic illustration of a monomer including a first tail region including dextran repeat units which are covalently linked to crosslinking groups, head groups, and optionally second tail regions, such as hydrocarbon tail regions.
Figure 19C:
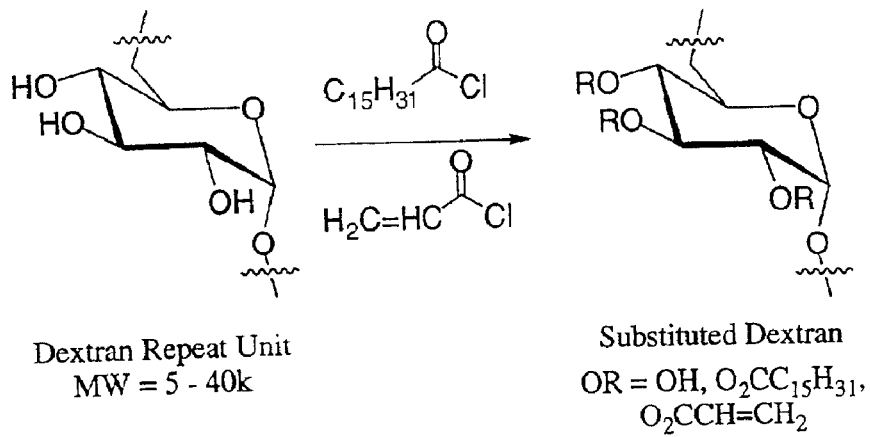
FIG. 19c illustrates exemplary routes of synthesis of monomers which include dextran repeat units.
Figure 19C:
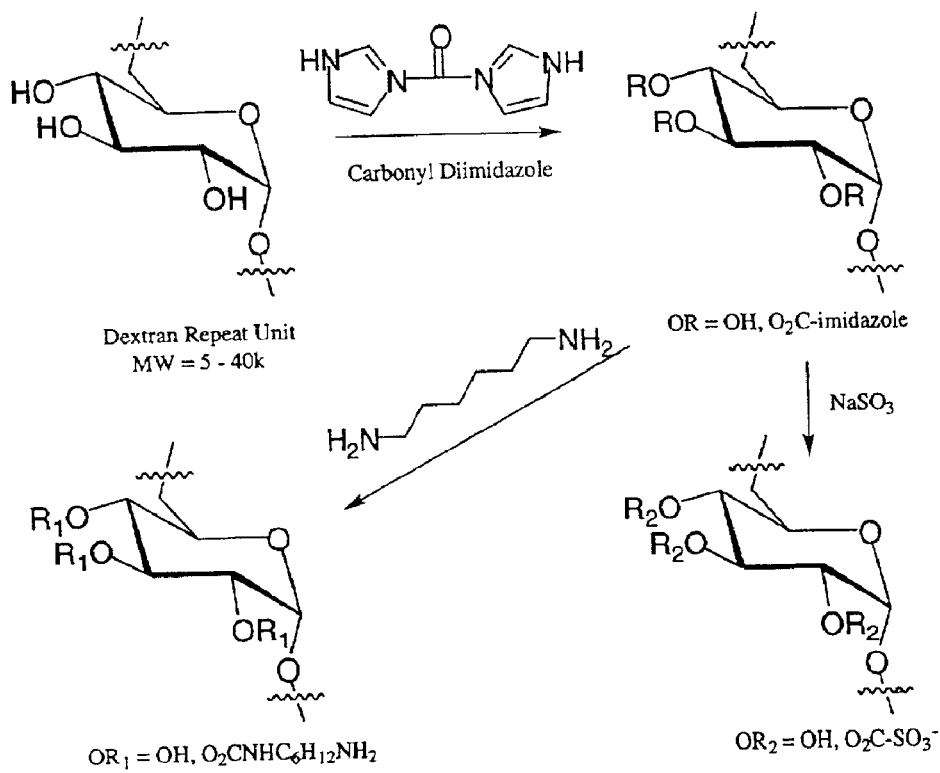
Figure 19D:
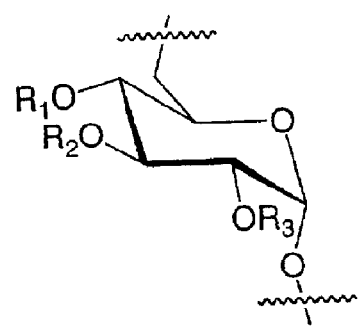
FIG. 19d is an illustration of substituted dextran monomers of Formula 6.

In one embodiment, as shown in FIG. 19d, a dextran monomer of Formula 6 for forming an SPC is provided, wherein, for example, $R_1$, $R_2$ and $R_3$ are independently H, or a moiety comprising at least one of a head group, a tail group, and a crosslinkable group, or combinations thereof, on any one or more of the saccharide units of the polysaccharide.

Functional Head Groups

The functional groups on the monomer capable of a binding interaction with a site on the target, referred to herein as "head" groups, may be any of a range of functional groups available in the art. The head groups are designed to complement a target surface moiety, optimizing the binding strength of interaction. The selection of the head groups will depend upon the charge and polarity of the surface of the target and the presence on the target of specific moieties such as hydrogen donors and acceptors, hydrophobic moieties, and charged groups.

The head groups can include polar or nonpolar moieties. Polar heads for interaction with a particular target may be negatively charged, positively charged, or uncharged. Nonpolar heads include bulky, sterically small, rigid, flexible, aliphatic and/or aromatic moieties. Uncharged polar heads include hydrogen bond forming or non-hydrogen bond forming functional groups. Hydrogen bond forming moieties include hydrogen bond donors or acceptors.

Figure 3:
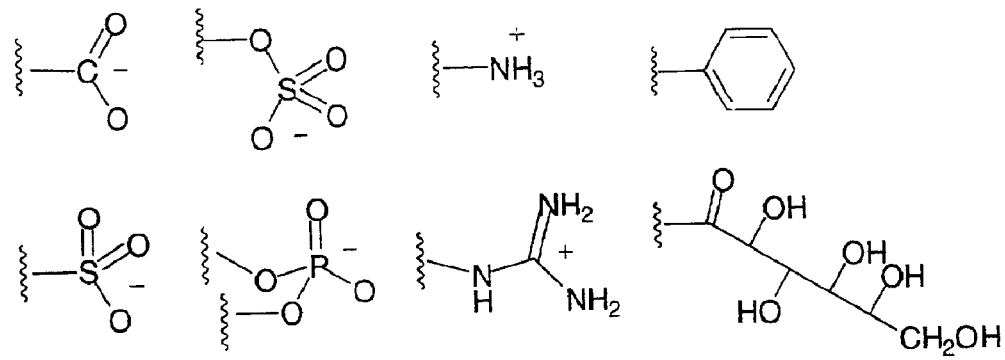
FIG. 3 is a schematic illustration of exemplary head groups provided on the monomers.

Other possible head groups include hydrophobic and hydrophilic moieties. The moieties may be aromatic or aliphatic, e.g., substituted and unsubstituted phenyl rings, such as benzyl, phenyl, nitrophenyl, ammonium phenyl salts, amines, carboxyphenyl, butylphenyl, isopropylphenyl, tolyl, ethylphenyl, phenol, substituted benzyl, or others. Suitable head groups also may be moieties such as alcohols, carboxylic acids, amides, amines, phosphates, sulfonates, alkanes, aromatic groups or other groups selected from the art. The head groups can, for example, include carbohydrates, aliphatic alcohols, aliphatic acids, sulfonic and substituted sulfonic acid salts, aliphatic amines, esters and amides, straight and branched alkanes. Exemplary head groups are shown in FIG. 3. Exemplary functional head groups include carboxylates, succinates, ammonium and other polar surfactant head groups, heteroaromatic bases, and sugars.

Useful head groups include naturally occurring systems and synthetic systems. For example, the head group on the monomer may be a naturally occurring amino acid, amino acid side chain, or a synthetic amino acid derivative. The head group can also comprise a dimer, trimer, or oligomer of the same or different amino acid or derivative thereof. Other exemplary head groups include purines or pyrimidines, such as adenine, cytosine, guanine, and thymine. Other exemplary head groups include sugars, carbohydrates and small or large glycoproteins.

A preferred embodiment is wherein the head group is the side chain of an amino acid, or synthetic derivatives thereof. Amino acids, analogues, or protected amino acid head groups are particularly useful for certain applications, for example when the target is a pathogen, such as a virus, because the SPC's may closely mimic antibody interactions with an antigen. Antibodies are proteins that recognize and bind to antigens on pathogen surfaces through antibody amino acid interaction with complementary antigen amino acids. FIG. 5 is a schematic illustration of the synthesis of monomers including amino acid derived head groups. The surfactant tail is conveniently attached via an amide linkage, and the carboxylate is either esterified or left charged.

There are 20 amino acids found in proteins. When assembled into a protein, the 20 amino acids provide a precise, unique three dimensional structure. An optimal monomer set to form an SPC thus may include all 20 amino acids (or mimics of the amino acid side chains) as head groups (see FIG. 5). However, advantageously, in contrast to proteins, the amino acid moieties do not affect the three dimensional structure of the SPC. The three dimensional structure is specified to a large extent by the tail structure and crosslinking. Thus fewer than the exemplified 20 monomers may be required, while still producing equally effective and precise surface mapping.

The Tail Region of the Monomers

The monomer in one embodiment is provided with a tail region. The tail region may comprise, for example, a moiety with a selected polarity, or other property, such as hydrophobicity, to promote self assembly of the monomers. In one embodiment, the head group and the crosslinking group can be linked directly or, optionally, via the "linker", also referred to herein as the "tail" region of the monomer. The tails of the monomers can be fabricated and designed, for example, to have surfactant functionality, and thus have efficacy in aqueous environments, biphasic systems, micellular systems and organic phases. By varying the hydrophilicity/hydrophobicity of the tail, the monomer can be designed for a specific solvent system. This permits more efficient self-assembly of the monomers, for example, in biphasic systems including an aqueous and organic phase.

In the monomer, or monomer set, the density of the crosslinking groups and the tails is varied and adjusted to create a SPC of the desired porosity and flexibility. The tail may vary from fully hydrophobic (e.g., alkyl chains) to intermediate polarity to hydrophilic (e.g., polyethylene glycol chains). FIG. 6 illustrates monomers with exemplary linkers or "tails" with varying polarity. Tails that have intermediate polarity (such as polytetramethylene oxide) or that are bipolar in nature (oligomeric block co-polymers of polyethylene and polyethylene glycol) are also potential tail architectures. If the surface of the target is largely polar, the head group and tail portion of the monomers near the surface of the target may also be polar to provide the best complementarity.

Hydrophobicity on the external surface of the SPC may be enhanced to, for example, promote deactivation of the target when the SPCs are administered in vivo, by chemical modification of the SPC, such as the attachment of any of a variety of $\alpha,\omega$-bifunctional oligomers which are commercially available. Wide varieties of chain length, polarity and branching are commercially available.

In one preferred embodiment, the tail can be a surfactant on the monomer. In this embodiment, the tail can be of any length so long as there is a surfactant effect. For example, the tail may be a hydrocarbon, including at least one carbon, or optionally tens or hundreds of carbon atoms, and may be branched or straight chain. For example, alkyl chains, such as straight alkyl chains preferably include at least 6 carbon atoms. The tail in one embodiment is a $C_4$–$C_{100}$ organic fragment, e.g., $C_{8-20}$, linear, cyclic or branched, and saturated or unsaturated, optionally with a crosslinking group attached at one or more regions of the tail. The tail may be linear or branched in architecture, and can be bifunctional (connecting one head and one polymerizable moiety) or polyfunctional (connecting one or more heads with many tail units), allowing networks of different rigidity and topology to be created when the tails are co-polymerized. The crosslinking groups may be attached at any point along the tail structure. For example, pentaerythritol or trimethalol propane linkers can permit the formation of tightly crosslinked, branched architectures. The tail may include multiple units of different linked subunits. Incorporation of short chains such as poly(ethylene glycol) units between the polymerizable moiety and the linker core will give more loose, flexible architectures. The overall combination of the linker units will largely determine the flexibility and rigidity and porosity of the network.

Linkers, or tails, which can be used include polymers and copolymers including poly(ethylene glycol), poly(ethylene oxide), poly(vinyl alcohol), poly(vinylpyrrolidone), poly(ethyloxazoline), poly(ethylene oxide)-co-poly(propyleneoxide) block copolymers, polysaccharides and poly(amino acids) such as gelatin, collagen, albumin and ovalbumin. Useful materials include polyethers, polyanhydrides, polyesters and polyphosphoesters. Mixtures and copolymers thereof also may be used.

Primarily via the tail structure and length, the rigidity or flexibility of an SPC-network can be designed to optimize the desired binding to the target, which is neither too loose nor too rigid and crosslinked. In the embodiment wherein the SPC is used to target a human pathogen such as a virus or bacteria, an SPC may be designed which does not substantially release the pathogen after complexing thereto, whereas for release and capture applications, looser SPCs can be used. Depending on the nature of the target as well as the method of application or utilization desired, the rigidity and porosity of each SPC can be tailored by incorporating monomers with tails of different lengths and architectures.

Figure 7:
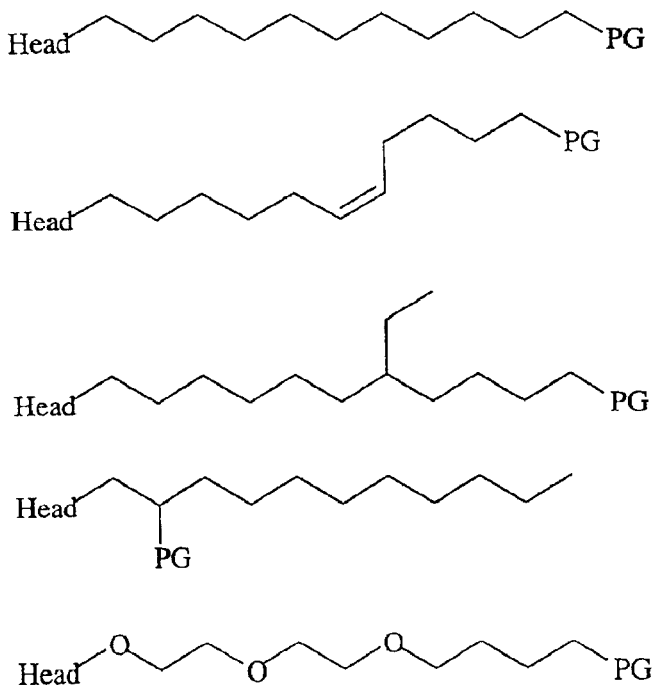
FIG. 7 is a schematic illustration of the structure of monomers with varying tail regions.

The monomers can vary in length and degrees of branching. The tail can be, for example, a polymer chain of repeating units such as ethylene oxide, with a length ranging, for example, of one to hundreds of repeat units. The polymer chain can be straight chain or branched, including one, or tens, or hundreds of branches. The branching can be, for example, random, star-shaped, or comb-shaped. In one embodiment, the tail comprises ethylene oxide or propylene oxide repeat units. Disruption of the tail structure can also be done by incorporating cis double bonds. To form a linker with branched chains, for example, ethoxylated pentaerythritol or trimethalol propane can be used. Monomers with exemplary linkers, or tails, are shown in FIG. 7. The linker also may be a nucleic acid molecule or polymer thereof.

Preferred tails are solvent dependent. Given a solvent for a specific application, a tail group can be appropriately chosen as to allow maximum self-assembly around a target in that given solvent. For example, if an enzyme needs stabilization to heat in aqueous solution, monomers with tails soluble in water can be synthesized. However, the monomer preferably is not completely soluble in a given solvent during the self assembly of the monomers, to encourage the assembly of the monomers around the target (i.e., the tail-solvent interactions preferably are weaker than the tail-tail interactions).

Crosslinking Groups

The "crosslinking group", also referred to herein as the "reactive group", on the monomer, as defined herein, includes any group capable of undergoing a covalent reaction with another of the monomers, and/or additional crosslinking compounds added during the monomer crosslinking step, in certain conditions. In the methods disclosed herein, after self-assembly of the monomers on the target, the monomers crosslink via the reaction of the crosslinking groups, to form the synthetic polymer complement. Preferably, the crosslinking groups react with each other to form a polymerized network of the monomers constituting the synthetic polymer complement. The terms "crosslinking" and "polymerizing" thus are used interchangably to refer to covalent bond formation of the monomers to form the SPC.

The number of crosslinking groups on the monomer can range, for example, from about one to several hundred, preferably from about one to one hundred, most preferably about one to ten. Monomers can be fashioned with one, two, or more selected number of crosslinkable groups, to allow formation of synthetic polymer complements in the form of networks of different tightness and topology upon crosslinking of the monomers. Computer simulation and molecular modeling may be used to guide the desired construction of the network and the type and amount of crosslinking groups needed to produce the network.

Exemplary crosslinking groups include free radically polymerizable moieties such as acrylates, methacrylates, acrylamides, vinyl ethers, and epoxides. The crosslinking of the monomers via the reaction of the crosslinking groups can be generated, for example, by heat or radiation, such as UV light. Catalysts and/or photo- or thermal initiators can optionally be used to promote crosslinking. Free radical polymerizations are one of many possible polymerization methodologies. Other crosslinking reactions as known in the art (Principles of Polymerization, 3$^{rd}$ Ed., Odian G. G.; Wiley, New York, 1991) such as ring opening, condensation, group transfer, anionic and cationic polymerization may optionally used.

Figure 8:
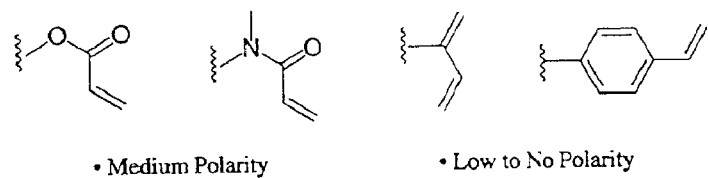
FIG. 8 is a schematic illustration of different crosslinking groups which may be provided on the monomers.

Exemplary crosslinking groups, also referred to herein as "polymerizable moieties" or "polymerizable groups" are shown in FIG. 8 and listed in Table 4.

For example, crosslinking groups include acrylate, methacrylamide, methacrylate, acrylamide, alkene, alkyne, vinylbenzene, α-methylvinylbenzene, divinylbenzene, epoxide, vinyl ether, maleic acid derivative, fumaric acid derivative, alkene, diene, substituted diene, thiol, alcohol, amine, carboxylic acid, carboxylic anhydride, carboxylic acid halide, aldehyde, ketone, isocyanate, succinimide, carboxylic acid hydrazide, glycidyl ether, silane, siloxane, chlorosilane, alkoxysilane, alkyne, azide, 2'-pyridyldithiol, phenylglyoxal, iodo, maleimide, aryl halides, imidoester, dibromopropionate, and iodacetyl.

In addition to crosslinking, the SPC can be formed by the condensation of polymeric surfactants around a target by slowly changing the solubility of the polymer by slowly changing the polarity, pH, or temperature of the solvent.

Synthesis of Monomers

The monomers may be synthesized using methods available in the art of organic chemistry (see for example, J. March, *Advanced Organic Chemistry*, Fourth Ed., John Wiley and Sons, New York, Part 2, pp. 255–1120, 1992). For example, the head groups and the crosslinking groups can be coupled to the linker using organic reactions, such as ester, amide, or ether linkage formation. Monomers in some embodiments also may be obtained commercially.

The components of the monomer, including the linker or head group, may be synthesized as an amino acid or a poly(amino acid). Reagents and starting materials in some embodiments can be obtained commercially. For example, amino acids and purines and pyrimidines can be purchased from chemical distributors such as Aldrich (Milwaukee, Wis.), Sigma Chemical Company (St. Louis, Mo.), Kodak (Rochester, N.Y.), Fisher (Pittsburgh, Pa.), Shearwater Polymers (Huntsville, Ala.), Pierce Chemical Company (Rockford, Ill.) and Carbomer Inc. (Westborough, Mass.).

Figure 9:
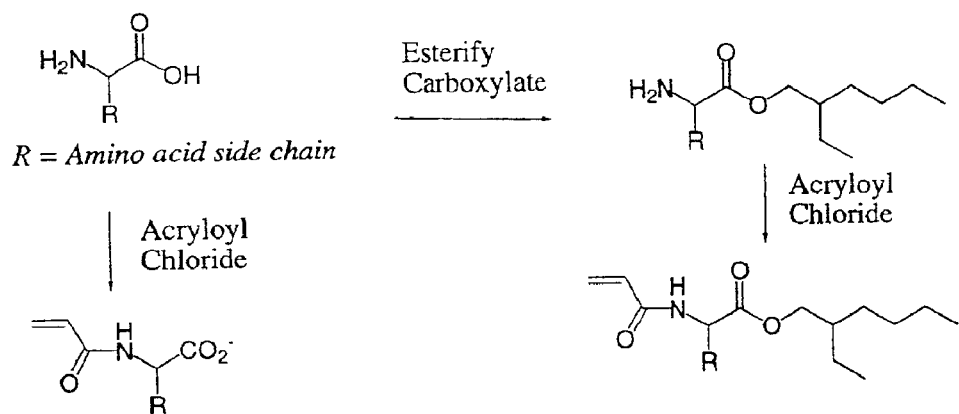
FIG. 9 is a schematic illustration of the synthesis of monomers with different amino acid head groups.

FIG. 9 shows an example of a synthetic scheme for synthesis of a monomer including amino acid head groups. Routes of synthesis of monomers with sulfonate head groups, acrylate crosslinking groups and hydrocarbon tails are shown in FIGS. 11a–11d. FIGS. 12, 13, 14 and 15 illustrate exemplary monomers, wherein PG is a polymerizable group, and wherein n is at least 1. For example, n may be on the order of about 6 to 100, or alternatively, in the embodiment wherein a longer hydrocarbon chain is utilized, n may be 100 to 1000, or more. The monomers can be synthesized using methods available in the art. See, for example the compounds and methods disclosed in Guyot, A. et al., *Advances in Polymer Science*, 111: 45–65 (1994); Joynes, D. and Sherrington, D. C., *Polymer*, 37 1453–1462 (1996), Gray, D. H., et al., *Advanced Materials*, 9:731–736 (1997); and Smith et al.; *J. Am. Chem. Soc*, 119:4092–4093 (1997).

In another embodiment, the linker, or portion thereof, may be a saccharide, or polymer thereof, such as a pentose group. The saccharide unit(s) may include derivatized functional groups for covalent attachment of polymerizable groups, head groups, or further linker regions.

The head group, such as an amino acid, can be coupled with the linker by standard chemical reactions. For example, amino acid heads may be coupled with glycol or oxide linkers through ester or amide linkages. The free acid or amine group is then passivated (prevented from further reaction) by standard ester or amide formation.

Ethoxylated linkers linked to polymerizable functional groups are available from ultra violet (UV) curable chemical supply companies, such as Sartomer (Exton, Pa.), Radcure (Smyrna, Ga.), and Henkel (Ambler, Pa.). Vinyl-ethers with polymerizable functional groups are available from Allied Signal (Morristown, N.J.). Other commercially available monomers, or precursors of monomers are available from Sartomer (Exton, Pa.), Radcure (Smyrna, Ga.), and Henkel (Ambler, Pa.). For example, solubilizing monomers or precursors thereof with pendant long-chain side groups are available. Examples of these are listed in FIG. 16, which shows polar, nonionic molecules commercially available from Polysciences (Niles, Ill.).

Figure 16:
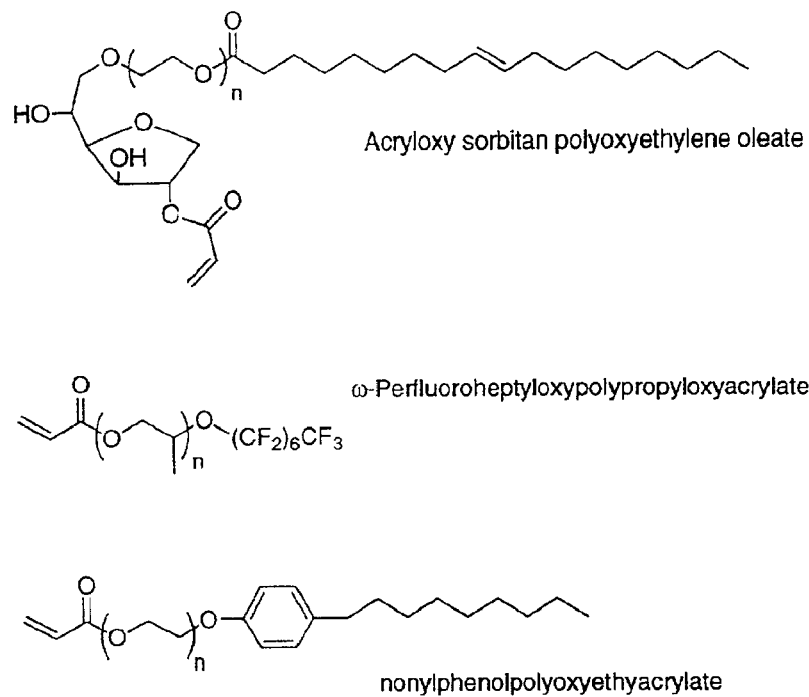
FIG. 16 is a schematic illustration of polar, nonionic crosslinkable monomers.
Figure 17:
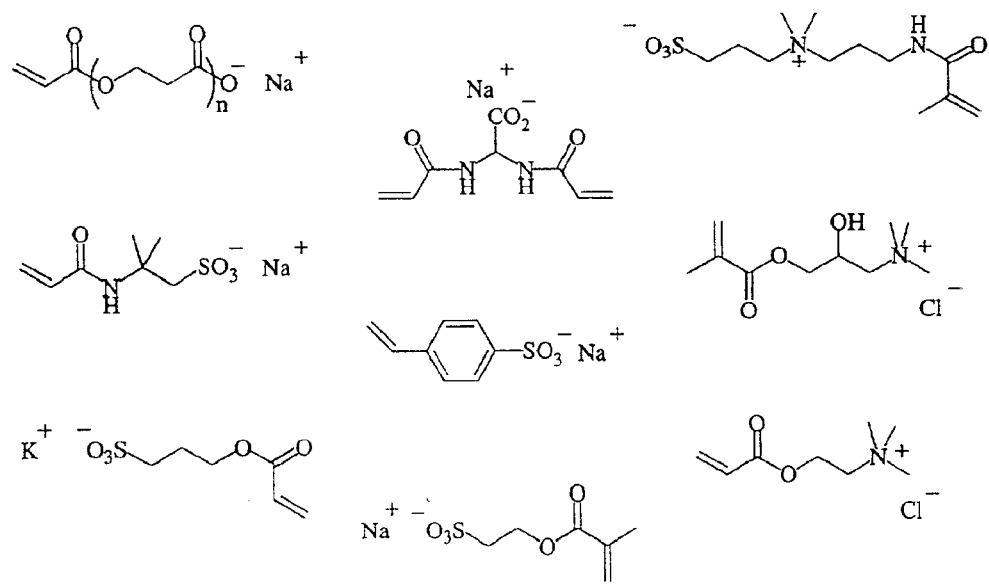
FIG. 17 is a schematic illustration of polar, charged crosslinkable monomers.

Monomers and monomer precursors are available commercially. Several examples of polar, charged monomers, or precursors thereof, including, carboxylate heads, sulfonate heads, ammonium heads and non-ionic heads are commercially available from Radcure (Smyrna, Ga.) and Polysciences (Niles, Ill.), as shown in FIGS. 16 and 17. These, or other, monomers may optionally be used as co-monomers to produce more architecturally complex molecules.

Monomer Sets

Also provided are monomer sets comprising monomers designed for use in forming a synthetic polymer complement for a particular target. The monomer set can be designed to include the desired head groups which are complementary to, and capable of binding to, sites on the selected target. The monomers in the set may be identical. Alternatively, a variety of different monomers with different head groups and the same crosslinking group may be provided in the set. In another embodiment, the crosslinking groups in a set may be the same or different. Optionally monomer sets may include non-reactive components such as cosurfactants.

In one preferred embodiment, the monomer set includes a plurality of different monomers, having different head groups and the same crosslinking group. The set may include 2, or optionally 3, or more different head groups. More complex sets may be designed which have about 4–6, or 7–10 different monomers, or optionally about 10–20, or 20 or more different monomers, each monomer having different head groups. The selection and ratio of monomers in a set may be designed selectively for a particular target.

Figure 4:
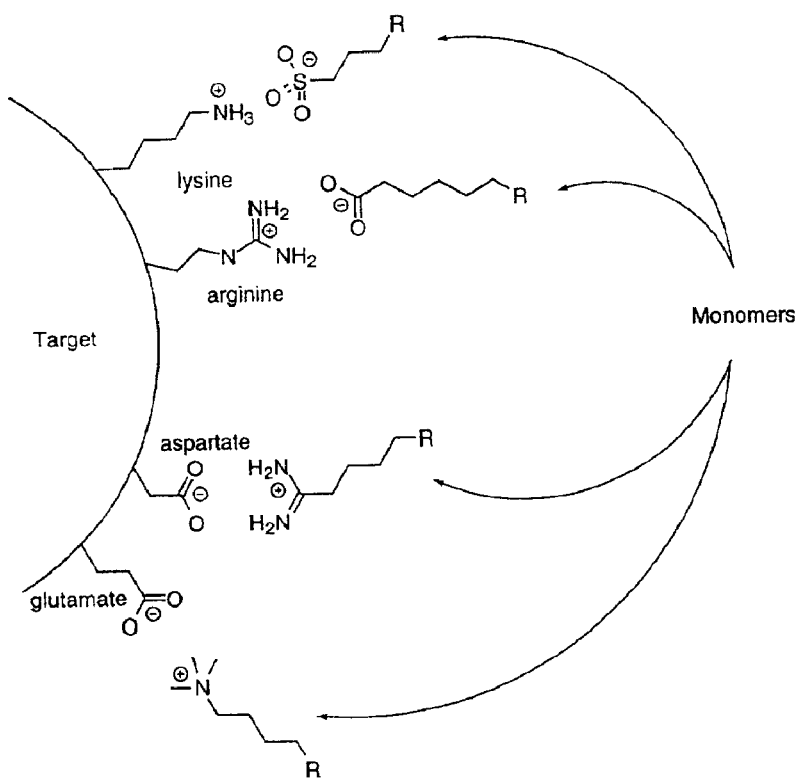
FIG. 4 is a schematic illustration of complementary monomers assembling on the surface of a protein target by complementary recognition of the charged surface residues of the target.
Figure 5:
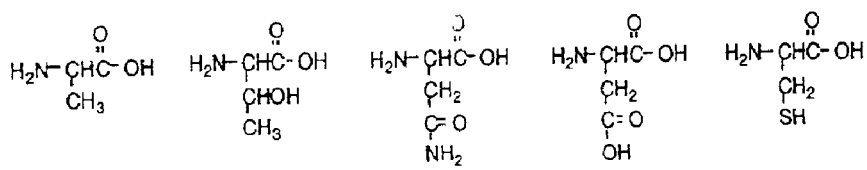
FIG. 5 is a schematic illustration of the synthesis of monomers with amino acid derived head groups.
Figure 5:
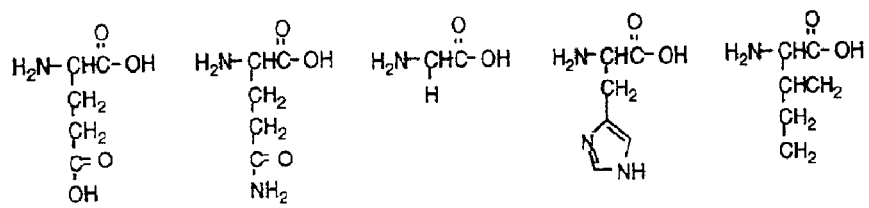
Figure 5:
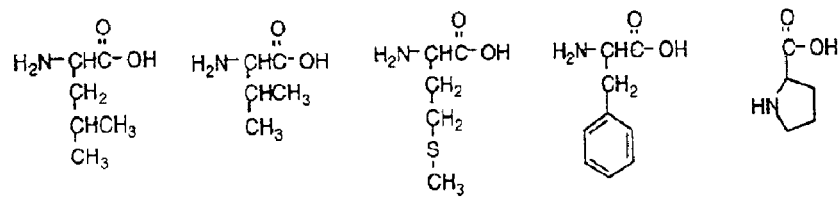
Figure 5:
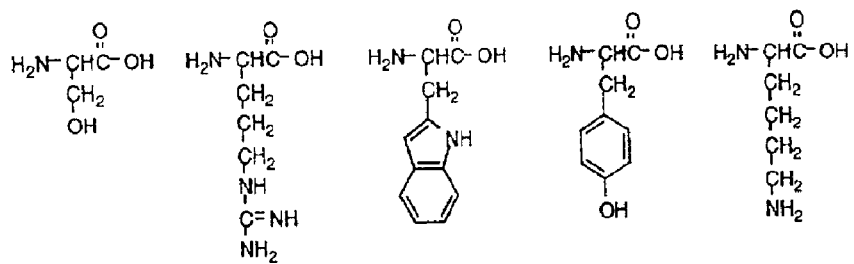
Figure 5:
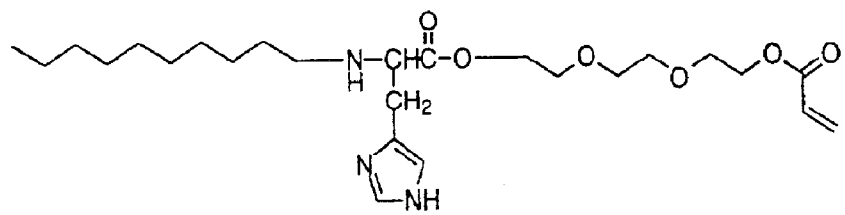
Figure 6:
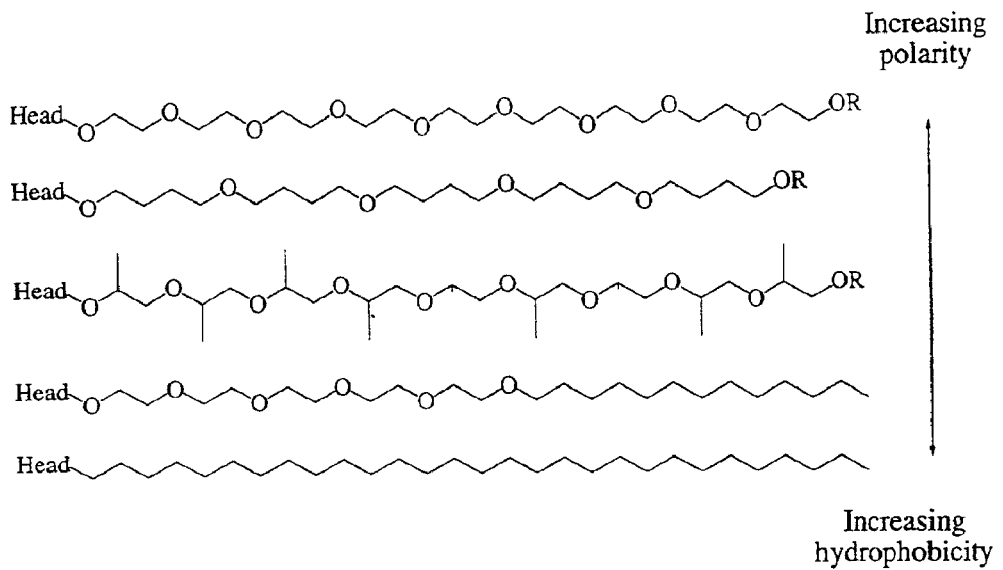
FIG. 6 is a schematic illustration of the structure of monomers with exemplary tails of varying polarity.

The selection of the head groups is aided by knowledge of the structure of the target, including consideration of whether the structure includes sites which are capable of hydrogen bonding (both donors and acceptors), or which are hydrophobic, charged, polar, or other property. The types, number and relative amounts of the monomers in a set thus can depend on the nature of the target. For example, if the target has a high density of negative charges, the monomer set may include a large number of positively charged heads, and vice versa. Hydrophobic targets require increased concentrations of nonpolar hydrophobic heads in the monomer set. Targets with a high degree of aromaticity require increased concentrations of heads containing aromatic end groups. Additionally, hydrogen bond donors on the target would require complementary hydrogen bond acceptors as the head group. An important consideration in the selection of the monomers in a particular tool set collection is diversity of the head groups to completely map the regions of interest on the target surface. As an example, most protein surfaces are heavily populated with charged residues such as lysine ($R-NH_3^+$) or arginine ($R-C(NH_2)_2^+$). Thus, the monomers are in one embodiment provided with heads which some of or all of the heads are anionic counterparts such as carboxylates ($R-CO_2^-$) and sulfates ($R-SO_3^-$). Anionically charged surface residues such as glutamate ($R-CH_2-CH_2-CO_2^-$) and aspartate ($R-CH_2-CO_2^-$) are complexed by complementary cationic head groups such as ammonium ($R-NR_3^+$) or amidines ($R-C(NR_2)_2^+$). FIG. 4 is a schematic illustration of complementary monomers assembling on the surface of a target by complementary recognition of the charged surface residues.

The selection of an optimal monomer set for a target, with the appropriate head groups and crosslinking groups, and the appropriate conditions for complexing with the target including concentration and solvent, is accomplished empirically. More preferably, thermodynamic phase equilibrium data are used as a guide. For example, when two small molecules are infinitely miscible, they are compatible and the molecules tend to attract each other. If one is on the surface of the target, the other can be chosen as the monomer head group.

Packing efficiency is also considered. Computer simulation based on available data on molecular interaction potentials and enthalpy of solution between functional groups to be used for heads in the monomers and target surface sites is an effective tool. The quantitative ratio of the ingredients used as heads in the monomer set is estimated by the surface area ratio of the particular target.

A consideration in the selection of the head components of a monomer set is the diversity of the heads necessary to completely map the regions of interest on the target surface. For example, heads of varying size, electronegativity, hydrogen bonding tendency, hydrophobicity, etc. can be chosen. The quantitative representation of heads in a monomer set can also be optimized for a particular complementary interaction.

In one embodiment, the sets are provided in an appropriate solvent for binding interaction with the monomer. Suitable solvents include polar protic (e.g., water, methanol), polar aprotic (e.g., dimethylacetamide, N,N'-dimethylformamide, dimethylsulfoxide, polyethylene glycol), nonpolar protic (e.g., octanol) and nonpolar aprotic (e.g., isooctane, hexane, toluene). Solubilities of organic compounds in various solvents are listed in the *Handbook of Chemistry and Physics*, 68th Edition, 1987–1988, Section C, pp. 42–553. The desired final use of the SPC will determine which solvent to use (e.g., for the protection of enzymes used in crude oil conversion, The SPC-enzyme complex must be soluble in oil-miscible nonpolar aprotic solvents such as iso-octane). Monomers can be designed with a specific tail composition to provide solubility in a given solvent. The monomers preferably have low to medium solubility in the solvent used for the self assembly process, in order to lower the competition of solvent for the monomers thereby encouraging the removal of the monomer from its free solution state to its self-assembled state around the target.

Cosurfactants, and mixtures thereof may be combined with the monomers in the monomer sets and used to form the SPCs. As used herein, the term "cosurfactant" refers to a surfactant that generally does not crosslink or react during formation of the SPC, but optionally promotes assembly of the monomers and optionally is incorporated noncovalently into the SPC during crosslinking of the monomers to form the SPC. In some instances, the cosurfactants referred to herein may also act as crosslinkable monomers, if they include a crosslinkable functional group, or a group that will crosslink or polymerize under selected conditions in the presence of the appropriate reagents. The cosurfactant in one embodiment is a molecule including a head group and a tail group but does not include a crosslinking group. Exemplary cosurfactants include Aerosol-OT (AOT, bis(2-ethylhexyl)

sulfosuccinate sodium salt). Other surfactants include phospholipids. Small molecules, such as $C_{2-10}$ alcohols, such as t-butanol and ethanol, also may added to promote self assembly. The monomer set may further include monomers that include a crosslinking group, but not a head group, such as acrylamide. The monomers and comonomers, such as monomers comprising crosslinking groups, such as crosslinking agents, are also referred to herein as the "building blocks" used to form the SPCs.

Exemplary cosurfactants which may be used include cationic (e.g., comprising ammonium cations), anionic (e.g., molecules comprising sulfonates such as alkylarylsulfonates), nonionic (e.g., polyethylene oxides), and ampholytic (e.g, dodecyl β-alanine) surfactants.

Other exemplary cosurfactants include fatty acid soaps, alkyl phosphates and dialkylphosphates, alkyl sulfates, alkyl sulfonates, primary amine salts, secondary amine salts, tertiary amine salts, quaternary amine salts, n-alkyl xanthates, n-alkyl ethoxylated sulfates, dialkyl sulfosuccinate salts, n-alkyl dimethyl betaines, n-alkyl phenyl polyoxyethylene ethers, n-alkyl polyoxyethylene ethers, sorbitan esters, polyethyleneoxy sorbitan esters, sorbitol esters and polyethyleneoxy sorbitol esters.

Cosurfactants that may be used include commercially available surfactants such as sorbitan esters including sorbitan monooleate (Span® 80), sorbitan monolaurate (Span® 20), sorbitan monopalmitate (Span® 40), sorbitan monostearate (Span® 60), sorbitan trioleate (Span® 85), and sorbitan tristearate (Span® 65), which are available, for example, from Sigma (St Louis, Mo.). Sorbitan sesquioleate (Span® 83) is available from Aldrich Chemical Co., Inc. (Milwaukee, Wis.).

Other exemplary commercially available surfactants include polyethyleneoxy(40)sorbitol hexaoleate ester (Atlas G-1086, ICI Specialties, Wilmington Del.), hexadecyltrimethylammonium bromide (CTAB, Aldrich), dioleylphosphoric acid (DOLPA), described in Goto et al., *Biotech. and Bioeng.*, 54:26–31 (1997), polyethyleneoxy(n)nonylphenol (Igepal, Rhone-Poulenc Inc. Surfactants and Specialties, Cranbrook, N.J.), and linear alkylbenzene sulfonates (LAS, Ashland Chemical Co., Columbus, Ohio).

In another embodiment, cosurfactants which may be used include polyoxyethylenesorbitan (Tween®) compounds. Exemplary cosurfactants include polyoxyethylenesorbitan monolaurate (Tween® 20 and Tween® 21), polyoxyethylenesorbitan monooleate (Tween® 80 and Tween® 80R), polyoxyethylenesorbitan monopalmitate (Tween(® 40), polyoxyethylenesorbitan monostearate (Tween® 60 and Tween® 61), polyoxyethylenesorbitan trioleate (Tween® 85), and polyoxyethylenesorbitan tristearate (Tween® 65), which are available, for example, from Sigma (St Louis, Mo.).

Other cosurfactants include lipids, such as phospholipids, glycolipids and cholesterol and cholesterol derivatives. Exemplary lipids include fatty acids, or molecules comprising fatty acids, wherein the fatty acids include, for example, palmitate, oleate, laurate, myristate, stearate, arachidate, behenate, lignocerate, palmitoleate, linoleate, linolenate, and arachidonate, and salts thereof such as sodium salts. The fatty acids may be modified, for example, by modification of the acid functionality to the sulfonate by a chain extension reactions known in the art.

Cationic lipids may be used as cosurfactants, such as cetyl trimethylammonium bromide/chloride (CTAB/CTAC), dioctadecyl dimethyl ammonium bromide/chloride (DODAB/DODAC), 1,2-diacyl-3-trimethylammonium propane (DOTAP), 1,2-diacyl-3-dimethyl ammonium propane (DODAP), [2,3-bis(oleoyl)propyl]trimethyl ammonium chloride (DOTMA), and 3β[N-(n', N'-dimethylaminoethane)-carbamoyl]cholesterol, dioleoyl) (DC-Chol).

Phospholipids which may be used also include phosphoglycerides, such as phosphatidyl cholines. Lipids developed in the art of gene delivery also may be used, as described, for example, in Lasic, "Liposomes in Gene Delivery", CRC Press, New York, 1997; and U.S. Pat. No. 5,459,127, the disclosures of which are incorporated herein by reference. Examples include N-[1-(2,3-dioleoxy)propyl]-N,N,N-trimethyl ammonium chloride (DOTMA), and dimyristooxypropyl dimethyl hydroxyethyl ammonium bromide (DMRIE). Other lipids include sphingosine.

The cosurfactants also may be modified into a crosslinkable monomer as disclosed herein by the covalent attachment of a moiety comprising a crosslinking group, such as an acrylate group or other crosslinking groups disclosed herein. Additionally or alternatively moieties comprising head groups as disclosed herein may be attached to the cosurfactants.

Self-Assembly of Monomers

Self-assembly of the monomers on the surface of a target is implemented in a solvent that does not significantly solvate or distort the target or the monomer set, or otherwise hinder the complementation process. Self-assembly occurs under conditions which permit a complex of the monomer set and the target to form spontaneously. Generally, if the solvent is near theta conditions, then the monomer set is in a preferred thermodynamic state where the heads are naturally attracted to the surface of the target (Tirrell, M. in *Interactions of Surfactants with Polymers and Proteins*; E. D. Goddard and K. P. Ananthapmanabhan—Ed.; CRC Press; Boca Raton; 1992; pp. 73–81).

In some instances, a synthetic polymer complement consisting of a partial network around a target molecule is produced. In subsequent use of the compound, target molecules are attracted to the complementary sites and come in through this "open" path to be captured. When the monomer set is chosen, some of the components in the monomer set are intentionally deleted for this purpose.

To combine a monomer set with a given target, a solvent or co-solvent system is chosen that promotes coverage of the target surface with the heads in the monomer set, while the linker and the crosslinkable group extend out towards, and preferably, are solvated in the media. Solution thermodynamics play a key role in solvent medium optimization (Tirrell, M. in *Interactions of Surfactants with Polymers and Proteins*; E. D. Goddard and K. P. Ananthapmanabhan—Ed.; CRC Press; Boca Raton; 1992; chapter 3; pp. 59–122). Some of the optimal characteristics of the solvent include: permitting the target to be maintained in its conformation, and ensuring that the target is not appreciably solvated or distorted by the medium; and ensuring that the heads are less compatible with the chosen medium than are the associated linker-crosslinking group portion of the molecule, so that the heads adhere to the target surface.

The components of the monomer set are allowed to self-assemble on the surface of the intended target. While not wishing to be bound by theory, it is believed that the self-assembly of the monomers onto the target occurs via free energy minimization. Various heads are attracted to different sites of the target surface thereby promoting aggregation of the heads of the monomer set on the target surface to achieve orderly assembly (organization). The target may also be viewed as the template around which the heads of the components of the monomer set congregate, leaving the linker/crosslinking group portion of the monomer extending from the coated target.

The phenomenon of free energy minimization is characteristic in physical and biological systems, for example, in micelle formation. Micelles in aqueous solution are formed because the polar head groups of surfactants such as lysophospholipids prefer an aqueous environment (are hydrophilic), whereas the nonpolar (hydrophobic) tails prefer to be excluded from aqueous environments. Therefore, the lysophospholipid heads self assemble to form a sphere with the tails facing inside, protected from the aqueous environment. It is this amphiphilic property that causes most phospholipids to arrange spontaneously into ordered structures when suspended in an aqueous environment. Micelles are the favored forms of the various lysophospholipids in aqueous solution because their formation results "favorable lipid-lipid interactions in the micelle form rather than the unfavorable lipid-water interaction, thus lowering the free energy of the solution.

FIG. 2*b* illustrates that free energy minimization leads to buried or partially buried targets 18 in the target-monomers complex 20. The spontaneous "coating" of the target 18 by the monomers in the monomer set is referred to herein as "hetero self-assembly." The term "hetero" is used because of the possible use of multiple heads 12 in the monomer set. Free energy minimization ensures that different sites 22 of the target 18 surface attract different but complementary elements 12 to adhere to the target 18. Hence, the force field and contour of the intended regions of the target 18 are mapped by the hetero self-assembled elements in the monomer set. In essence, a molecular mold of the target 18 is produced. This enables molecular or nano-level complementary mapping.

More detailed complementary force field maps and contour copies are achieved by successive refinement of the quantitative composition of the monomer set. HPLC, light scattering, UV and fluorescence spectroscopy, ESR, and electron microscopy, for example, may be used for studying the kinetic constant and equilibrium constant. Through successive modeling and experimental refinements, formulations suitable for complementary assembly around different targets may be designed and prepared.

The monomers are chosen or synthetically tailored to permit self-assembly followed by the polymerization process. Self-assembly of the reactive monomers is promoted by surface aggregation of heads on the target, while the tails, or linkers, are solvated in the surrounding solvent media. Self-assembly is described by surface and solution thermodynamic principles. Self assembly applies to both head-head associations as well as tail-tail interactions such as hydrophobic aggregations for example. Either or both may prove important in the overall free energy minimization that accompanies self assembly.

The magnitude of the interactions of the head groups with the target surfaces and the self-assembly of the monomers on the target will depend upon the nature of the target surface. Targets such as proteins and larger structures, such as viruses and bacteria, have many interacting components. Thermodynamic-based approximations of the energies of interaction can be made (D. H. Williams, *Aldrichimica Acta*, Vol. 24, 1991, pp. 71–80; G. M. Whitesides et al., *Science*, Vol. 254, 1991, pp. 1312–1319).

For example, the free energy of association (ΔG) can be broken into two components: the enthalpy (ΔH) and entropy of association (−TΔS). In comparison to typical covalent bonds (−40 to −100 kcal/mol), enthalpic (ΔH) noncovalent interactions are relatively weak. However, large numbers of noncovalent interactions can lead to very stable complexes (e.g., antibody-antigen associations range from −5 to −15 kcal/mol and the strongest noncovalent interaction in nature, biotin-avidin, is around −20 kcal/mol) compared to thermal energy at room temperature (RT=0.6 kcal/mol). Model systems indicate that the association of methylene units in water is favorable by −1 to −1.5 kcal/mol/$CH_2$. This interaction is small, but favorable, and large hydrophobic surfaces tend to associate in water. In aqueous solutions, hydrogen bonds between dissolved substrates are slightly energetically favorable by −0.1 to −5 kcal/mol. Ionic bonds tend to have larger free energies of formation of approximately −1 to −10 kcal/mol, and their formation is energetically favored. Thus the strength of monomer-target interaction will be based on ionic and hydrogen bonds, as well as hydrophobic association. These interactions are stronger in nonaqueous solvents due to less competition between the solvent and the headgroups on the monomer and the functional groups on the target.

Entropy (−TΔS) also plays an important role in equilibrium, noncovalent association processes. As an approximation, the loss in translational entropy on bringing together two particles originally at millimolar concentration contributes approximately +5.5 kcal/mol, and the loss in conformational entropy in freezing a freely rotating bond with three equally populated conformations in one conformation contributes approximately +0.7 kcal/mol. Monomers designed for self-assembly are in one embodiment preferably rigid to achieve good intermolecular contact between the interacting surface and to maximize the area of contacting molecular surface. In certain solvents (e.g. water) many solvent molecules are bound to dissolved substrates. In water, these solvent molecules are referred to as "solvents of hydration". When two substrates self assemble, fewer numbers of solvent molecules bind to the self-assembled pair. Thus several solvent molecules are released from a tight salvation of the substrate to the free solvent pool, and entropy gains of 1–10 kcals/mol or more (at room temperature) can be realized from this release, thus aiding the spontaneous thermodynamics of self assembly of monomers on the target (for a discussion, see D.Eisenberg and D. Crothers, *Physical Chemistry with Applications for Life Sciences*, Benjamin/Cummins, Menlo Park Calif. 1979, pp 337–340).

Although each interaction may be energetically weak, the sum of the large number of interactions possible on the surface of a target may be great. Many-point multidentate binding is the driving force for the highly efficient binding interaction of the target-SPC complexes. The binding affinity of the product SPC can determined by measuring the number of targets bound and unbound by the SPCs. The equilibrium is shown below:

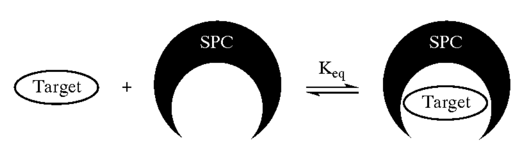

$$K_{eq} = \frac{[\text{Complex}]}{[\text{Target}]\ [SPC]} = e^{(-\Delta G/RT)}$$

The concentration of target left in solution will decrease as $K_{eq}$ increases. $K_{eq}$ will increase exponentially as the free energy of interaction increases, which is additive among all the many small interactions that make up the target-SPC complex. For example, assuming there are 20 interactions between the SPC and the target, and each interaction only contributes –1 kcal/mol on average. The total free energy of interaction is then –20 kcal/mol and the equilibrium constant is $4\times10^{14}$ in favor of association. In one embodiment, the SPCs may be used to sequester a pathogen in blood. At a SPC concentration in the blood of only $10^{-3}$ M, targets would be sequestered down to a concentration of $10^{-11}$ M.

In the self-assembly process, the targets may be in free solution and or bound to a solid surface, such as an ELISA plate. Self-assembling monomers are used which have tails with an affinity for one another, to encourage surface stabilization of the assembled structure, but which still allows monomer mobility, so that the head groups can optimally line up and the complementary structure can be optimized. For targets soluble or present in water, the self-assembly process is conducted in an aqueous buffer solution.

During the self-assembly process, the concentrations of the monomers can be preselected for a particular application. The concentration can be kept low so that the polymerized SPCs are small, discrete entities that recognize one or a few targets such as pathogen antigens. Once the monomers are assembled around the target, they are polymerized to form the SPC. Mixing and polymerization may be performed on a small scale in scintillation vials, or in larger flasks or reactors as needed.

Once synthesized, the reactive monomers, which preferably are surfactant-like in nature, must be induced to assemble around the template molecule or structure. It is desired that the surfactant monomer heads interact with complementary species on the template molecule. Also, it is preferred that the surfactant tails interact with other tails and with the solvent rather than the template surface. For example, two assembly approaches can be employed. The first uses only a single solvent. The second uses two immiscible solvents that form a two phase system. Thermodynamic principles will guide the solvent selection and self-assembly method.

The single phase assembly method is a process in which the surfactant monomers and templates are added to a solvent, and mixed. The solvent media may use either one solvent or cosolvents. The mixing procedure is designed by careful consideration of solvent-template and solvent-surfactant interactions. If the solvent is too good, or strong, for the surfactant and the template, it will be thermodynamically unfavorable for the surfactant to interact with the template molecule, since both will prefer the solvent environment. Advantageously, the amphiphilic nature of the surfactant monomer results in the effect that in a good solvent for the tail, the head group will prefer a different environment, most preferably the complementary environment located on the template surface. To further promote self assembly, a weak solvent for the monomer is preferably used. Solvent strength may be quantitated in terms of various thermodynamic models. In terms of polymer solution thermodynamics, a theta solvent for the surfactant tails and for the template is preferably used (for a discussion on theta solvents and polymer solution thermodynamics, see for example Tirrell, M. in *Interactions of Surfactants with Polymers and Proteins*, Edited by E. D. Goddard and K. P. Ananthapmanabhan, CRC Press, Boca Raton, 1992, p. 73–81). In terms of regular solution theory, a solvent with a solubility parameter that is different from the template and surfactant tail solubility parameter is preferably used (see for example Chapter 9 in *Molecular Thermodynamics of Fluid-Phase Equilibria*, $2^{nd}$ ed., by J. M. Prausnitz, R. N. Lichtenthaler, and E. G. de Azevedo, Prentice-Hall, Englewood Cliffs, 1986). A theta solvent, or a solvent with a poorly matched solubility parameter, will promote stronger tail-tail interactions, which will encourage assembly around the template. Additionally, when ionic surfactants monomers are used in aqueous solutions, the ionic strength of the solution is preferably kept as low as possible (if the template is a protein, too low of ionic strength may cause protein denaturization) to encourage surfactant monomer-template ion-pairing. If surfactant monomers with different structures are used, they preferably are added sequentially to the solution.

When two phases are used, the surfactant monomer and the template are first solvated in different, immiscible solvents (e.g., water and oil). A two phase system is advantageously used to aid in surfactant-template complexation. The assembly of the surfactants around the template is accomplished by contacting the two phases and extracting the template into the surfactant-containing phase. The template alone is preferably relatively immiscible in the solvent which contains the surfactant.

An example of a two-phase extraction method has been used by Paradkar and Dordick to form ion pairs between the surfactant molecule Aerosol-OT (AOT, bis(2-ethylhexylsulfosuccinate sodium salt) Aldrich Chemical Co., Milwaukee, Wis.) and the enzyme α-chymotrypsin (Paradkar, V. M. and Dordick, J. S., *J. Am. Chem. Soc.*, Vol. 116, 1994, p. 5009–5010) for a different purpose. Paradkar et al. mixed equal volumes of an aqueous and organic phase to accomplish the transfer of greater than 90% of the enzyme (the template) into the organic phase by ion pairing with greater than 50% of the AOT surfactant. In the present invention, the mixing of a small volume of concentrated template solution with a large volume of surfactant solution may be used.

Using an appropriate method of template transfer, complementary matching of surfactant monomer head groups around the template is achieved. If more that one kind of reactive surfactant is used, after the template has been complexed with the extracting surfactant monomers, additional surfactant monomer types may optionally be added sequentially, using titration or other addition methods.

In another embodiment of the invention, a microemulsion two phase system may advantageously be used to aid in surfactant-template complexation. The assembly of the surfactants around the template is aided in a microemulsion where the template is incorporated in or at the surface of a micelle or a reverse micelle in which the building blocks are concentrated.

Labile bonds (e.g., disulfides, metals, etc.) can optionally be used to anchor crosslinkable surfactants directly to residues on targets. Covalent bonds between the surfactants and targets will result in stronger interactions than noncovalent bonds.

This effect is examined using the Gibbs Free Energy Equation, $\Delta G=\Delta H-T\Delta S$. $\Delta G$ (the overall strength of assembly) is the change in free energy between the assembled and unassembled states which is composed of both enthalpy and a entropy terms. $\Delta H$ is the difference in enthalpy (bond strength) between the bonded and non-bonded states. Since the surfactant-to-target bond is covalent or coordination in character, the entropy term ($-T\Delta S$) of assembling surfactants is dominated by the favorable and large binding strength of the newly formed covalent or coordination bond(s) ($\Delta H$) to give a very favorable overall free energy ($\Delta G$) of assembly. $-T\Delta S$ is the temperature dependent entropic term which takes into account the unfavorable process of removing molecules from their solution phase and into an ordered array around a target. Therefore, by using labile covalent bonds between the target and the surfactant, the overall free energy of assembly (ΔG) is made more favorable through the strength of this bond. Cleaving this bond results in a functionality that has spatial and charge complementarity between the crosslinked shell and the native target.

Crosslinking

After hetero self-assembly of the monomers, the crosslinking groups are preferably reacted in order to crosslink the monomers. In one embodiment, the monomers thus are polymerized into a network to create a thin shell around the target. The reaction is conducted preferably in the presence of the suitable solvent or in the absence of the solvent after its extraction. At least a portion of the resulting network of crosslinked monomers complement the surface topology and force field of the target.

Figure 18:
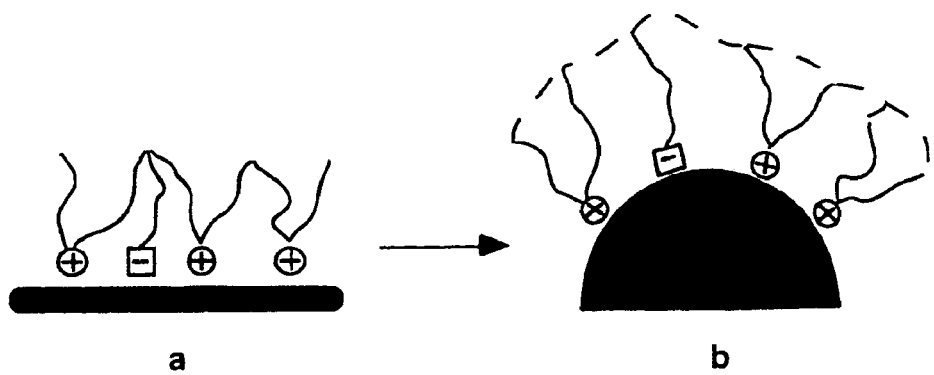
FIG. 18a is a schematic illustration of directly crosslinked monomers.
FIG. 18b is a schematic illustration of monomers connected via multifunctional crosslinking agents, wherein the crosslinking agents are shown as dashed lines.

In one embodiment, the SPC is created by polymerization of the crosslinking groups along the backbone after self assembly around the target. Polymerization of functional groups such as acrylates can be triggered by either heat or radiation. Additional crosslinkers (monomers without specific "heads") may also be added to the solution to help create bridges between crosslinking groups (also referred to as crosslinking moieties) on different monomers and to alter the crosslink density. FIG. 18 illustrates the direct linking of monomers with heads that associate with the target (FIG. 18a), and monomers with heads that associate with the target connected via monofunctional and multifunctional monomers (crosslinking agents) (FIG. 18b). In FIG. 18b, the crosslinking chains are shown as dashed lines. Different degrees of substitution allow networks of different topology and rigidity to be created. In one embodiment, the SPC must be flexible enough so that the target molecule can reversibly enter into a SPC binding site, yet preferably rigid enough that the three dimensional cavity remains intact when it is not bound to a target molecule. The range of rigidity in one embodiment is that exhibited by an antibody.

Polymerization can be accomplished by reaction methods described in the texts of L. H. Sperling, *Introduction to Physical Polymer Science*, Chapter 1, pp. 1–21, John Wiley and Sons, New York, 1986, and R. B. Seymour and C. E. Carraher, *Polymer Chemistry*, Chapters 7–11, pp. 193–356, Dekker, New York, 1981. The Free-radical mechanism is one example. Both heat and UV can be applied to accelerate polymerization.

Exemplary crosslinking groups include acrylates, methacrylates, acrylamides, vinyl ethers, and epoxides. Other exemplary crosslinking groups include methacrylamide, vinylbenzene, α-methylvinylbenzene, divinylbenzene, epoxide, vinyl ether, maleic acid derivative, fumaric acid derivative, alkene, diene, alkyne, substituted diene, thiol, alcohol, amine, carboxylic acid, carboxylic anhydride, carboxylic acid halide, aldehyde, ketone, isocyanate, succinimide, carboxylic acid hydrazide, glycidyl ether, silane, siloxane, chlorosilane, alkoxysilane, azide, 2'-pyridyldithiol, phenylglyoxal, iodo, maleimide, aryl halides, imidoester, dibromopropionate, and iodacetyl. The crosslinking of the monomers via the reaction of the crosslinking groups can be generated, for example, by heat or radiation, such as UV light. Catalysts or photo- or thermal initiators can be used to promote crosslinking. Such initiators and catalysts are commercially available. Acrylate chemistry methods known in the arts may be used, as described, for example, in U.S. Pat. No. 5,459,176; A. Sassi, *Polymer Applications for Biotechnology*, (D. Soane ed. Prentice Hall 1992); and *Encyclopedia of Polymer Science and Engineering* (M. Bikales, Overberger, Menges eds., Wiley 1988), the disclosures of which are incorporated herein by reference. UV light, using initiators such as the Irgacure™ and Darocur™ initiators (Ciba Specialty Chemicals, Tarrytown, N.Y.) may be used to accelerate the cure the acrylic or acrylamide crosslinking groups.

Monomers Conjugated to Targets

Monomers or SPCs may be covalently linked to targets, such as enzymes. Monomers may be covalently linked to biomolecules, such as enzymes to change the reactivity and stability of biomolecules. For example, a monomer comprising a hydrophobically or otherwise modified dextran may be covalently linked to a target, such as an enzyme, followed by crosslinking.

Figure 43:
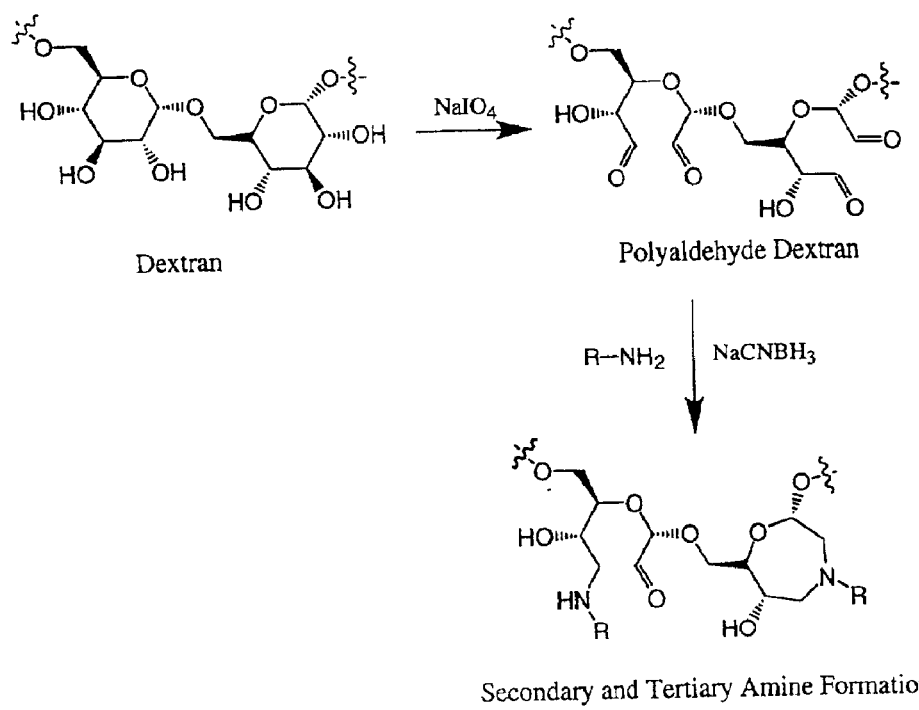
FIG. 43 is a scheme showing the oxidation of dextran followed by conjugation to amines.

The diols of dextran may be oxidized with sodium periodate to produce aldehydes. This procedure results in two aldehydes per glucose unit. The polyaldehyde dextran is very reactive to molecules containing amines to form Schiff bases followed by reductive amination to create stable secondary or tertiary amine linkages (FIG. 43). The amine may be from the lysines of a biomolecule or small amine containing molecules. This chemistry is discussed in Bioconjugation Techniques, G. T. Hermanson, Academic Press, San Diego, 1996, pp 620–622. For example, dextran may be covalently attached to α-chymotrypsin (CMT) through its lysines and to a hydrophobic amine to allow extraction into isooctane solution. After conjugate formation and isooctane extraction, the unreacted aldehydes may be crosslinked for greater stability with alkyldiamines.

Optional Release of the Target

In one embodiment, after the assembled monomers are crosslinked to form the SPC, the target template is subsequently released and the SPC is isolated. Thus, the target optionally is released from the synthetic polymer complement, for example, by controllably expanding and contracting the crosslinked network. To release a target, the interactions that were exploited in assembling the superstructure may be dampened or reversed, or the target's morphology may be altered. This can be implemented by, for example, altering the pH, ionic strength, solvent or temperature of the target-SPC complex. Electrostatic interactions can be dampened by increasing the ionic strength. Altering the pH, using urea, or raising the temperature all can be used to alter the charge and charge distribution of a target such as a biomolecule, or denature a template protein. With these changes, the noncovalent interactions between the template and the SPC are disrupted, causing the target to be released. Alternatively, proteases may be added to the solution which will digest or break down a peptide target. Conditions are selected such that the SPC remains essentially undamaged. For example, the SPC may have enhanced stability due to its covalently crosslinked and hydrolytically-stable chemical structure.

Detachment of the target can be facilitated by slightly swelling or deswelling the synthetic polymer complement, induced by minor adjustment of the co-solvent medium or system temperature. Crosslinked networks undergo volumetric transitions, triggered by minute changes in the environment, e.g., temperature, pH, ionic strength, co-solvent composition, pressure, and electric field, etc., as discussed, for example, in L. H. Sperling, *Introduction to Physical Polymer Science*, Chapter 4, pp. 97–121, John Wiley and Sons, New York, 1986. To make this swelling/deswelling effect more pronounced, thermoresponsive monomers (e.g., N-isopropylacrylamide) may be added to the monomer set. The responsive monomers are then copolymerized into the network. (See, for example, Responsive Gels, volumes 109 and 110 of *Advances in Polymer Science*, K. Dusek ed., Springer Verlag 1993, and A. Sassi, et al., in *Polymer Applications for Biotechnology*, D. Soane ed., Prentice Hall, 1992.

Optionally, the SPC-target complex is the desired product. The complex either restrains or enhances the biological catalytic or other active functions of the target or allows activity in hostile environments (e.g., heat, solvent, etc.). Thus, the SPCs can be used to stabilize molecules such as enzymes.

After polymerization, the SPC-target complex or separated SPC may be characterized using methods available in the art. UV/Vis spectrometry in conjunction with gravimetric methods may be used to quantitate the amount of SPC per unit weight of the SPC-target complex. For example, either the SPC or the target will be designed to have an absorbing species not present on the other component. From the absorbance, the concentration of the absorbing species can be calculated. The total mass of SPC and target together can be determined gravimetrically. FTIR, HPLC or other methods may be used to determine the extent of reaction or presence of unreacted monomers in the SPC product. Purification techniques such as precipitation, washing, chromatography, and dialysis can be employed to remove unwanted side products or unreacted monomer. Gel permeation chromatography and low angle laser light scattering can allow the size assay of the polymerized mixture.

Properties of the Synthetic Polymer Complement

SPCs capable of highly specific recognition of a target may be prepared. Reciprocal mapping of a target not only produces a topological complement (including chirality) but also a force-field (polar, nonpolar, charged) complement between the target and the SPC. The SPCs may comprise a tailored polymeric network around the target with interior or exterior surfaces including regions which recognize the targets. A range of synthetic polymer complements may be produced, which include functional groups complementary to the target. This method produces nanoengineered, fully crosslinked macromolecular networks provided with specifically designed domain surfaces suitable for lock-and-key or induced fit docking with the target.

SPCs may be formed which precisely map the three-dimensional surface contours, charge and polarity of the target. The SPC is formed by crosslinking the monomers in place on the target, thus resulting in complementary shell partially or fully around the target.

In a preferred embodiment, the SPCs are formed from monomers with surfactant groups. Exemplary surfactant groups include hydrocarbon tail regions, for example including about 6 to 20 carbon atoms. The presence of the surfactant group in the monomers permits the self-assembly of the monomers around a target. The surfactant also allows a stable, more precisely complementary construct to be formed prior to polymerization. Subsequently, the monomers are polymerized via crosslinking groups present on the monomers. Crosslinking groups, such as trimethylolpropyl-triacrylate, and non-surface active building blocks such as acrylamide and polyethyleneglycoldiacrylate may be provided in the monomers to alter crosslink density, structural rigidity and solubility if desired.

The use of surfactant monomers permits the monomers to be used to form SPCs, for example, in the form of a thin film or monolayer or of the size of a protein molecule. An SPC is in one embodiment a high fidelity complement of the target. In one embodiment, small SPCs are provided that are less than about 1000 nanometers in average diameter. The small SPCs may be soluble in different solvents. The small SPCs are, for example, nanometers (about 1–400 nm) in average diameter, and the polymer network of the SPC has, for example, a thickness ranging from the length of the monomer molecules to about 10 nanometers. The SPCs are advantageously, but not necessarily, formed from a cocktail of different monomers with a high diversity of varying head groups which can assemble around the target, which permits the SPCs to be formed with a high affinity for the target.

Figure 24:
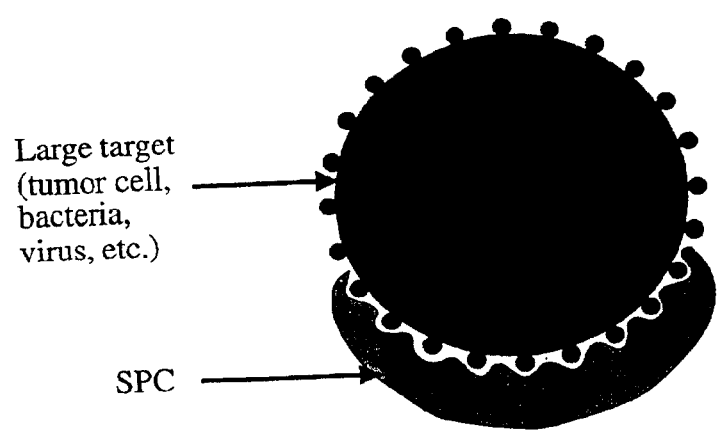
FIG. 24 is a schematic illustration of an SPC complexed with a large biostructure.
Figure 25:
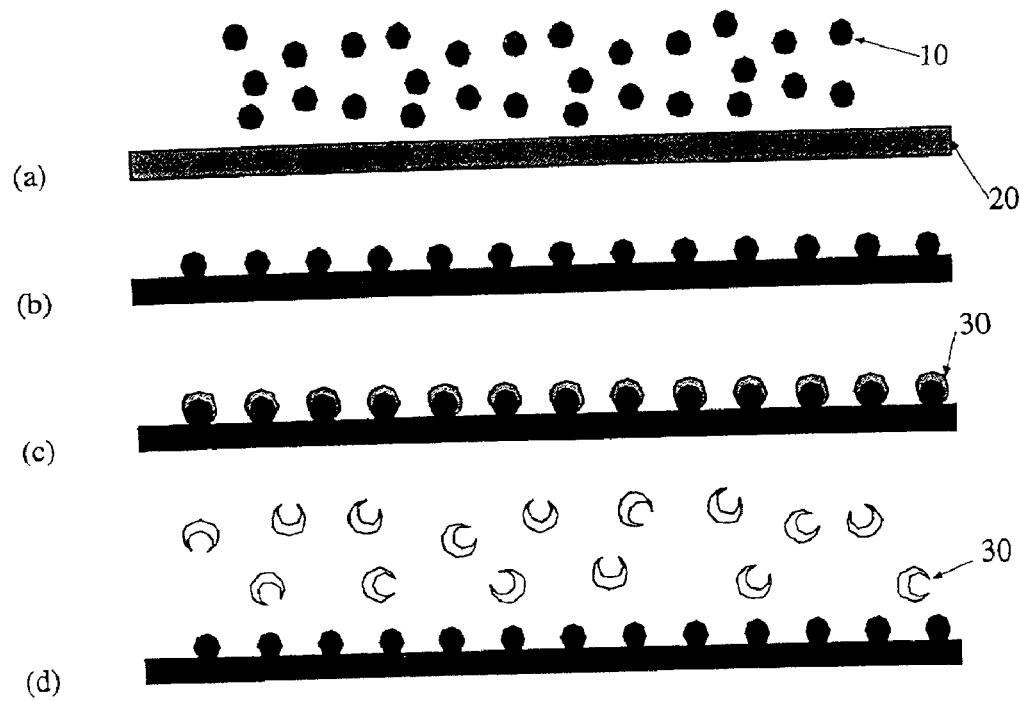
FIG. 25 is a schematic illustration of SPC formation on a surface.
Figure 26:
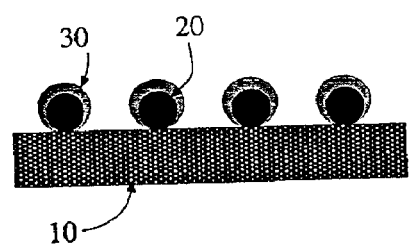
FIGS. 26 and 27 are schematic illustrations of the formation of SPCs on targets immobilized on a surface.
Figure 27:
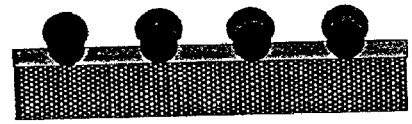

In one embodiment, the small SPCs are formed on a nanomolecular scale, for example with an average diameter of about 1 to 400 nm, which permits them to be used in a broad range of applications. Due to their small size, the small SPC's motion is controlled mainly by thermal fluctuations rather than gravity. Therefore, this SPC remains soluble. The advantages of remaining in solution are faster kinetic rates of interaction or reaction. For these reasons, these small SPCs can be used in vivo as drugs or in the form of an SPC-enzyme complex which stabilizes the enzyme while remaining free in solution. Because they are unconnected and free in solution, no diffusion barrier exists for these SPC structures, since the diffusion of a molecule to a surface reactive site is much slower than to a site free in solution. In another embodiment, larger SPCs ranging in size, for example, from about 0.1 micrometers to several micrometers, e.g. 1–10 micrometers, may be fabricated for recognition of viruses, bacteria and whole cells, or substantial portions thereof, as illustrated in FIG. 24.

The SPCs permit imprinting of a variety of different sized targets. In one embodiment, the nanoscopic dimensions of the SPCs and the few number of target binding sites provide many advantages over prior an MIPs technology. The SPCs permit efficient use of nearly all target complement sites formed, whereas the majority of sites in the MIPs are inaccessible to the target due to their bulk polymerization synthesis.

Advantageously, the SPCs have a tailored flexibility. Because of their small size, SPC deformation does not influence, and is not influenced by structure fluctuations far removed from the binding site. In contrast, in large, molecularly imprinted polymeric beads (MIPs), deformation of the beads can have a deleterious effect on distal binding sites on the beads. The stress of the material deformations concentrate at the defects; MIP sites are defects in the regularity of the crosslinked structure therefore the deformation will alter the MIP site and reduce its binding efficiency. The SPCs are advantageous because they permit a better fit to the target than a large inflexible monolithically crosslinked polymer bead with multiple binding sites. The SPC is capable of thermal fluctuations which bring the SPC into target contact in a favorable binding conformation. In some embodiments, the binding process may be envisioned as the SPC first partially interacting with a target molecule at a few complementary sites, and then gradually adhering on to more complementary target sites as thermal fluctuations bring the SPC into target contact in a favorable binding configuration similar to the action of an antibody.

SPC's may be formed that interact with a target in the pattern of induced fit. In induced fit models, entities such as an enzyme change shape upon binding the substrate. The active site has a shape complementary to that of the substrate only after the substrate is bound. In this embodiment of the SPC, the heads are connected to the linkers that are part of a loose network. The elasticity of the network allows the heads to move more freely than in a tighter network to accomplish induced fit.

SPCs are preferably formed from reactive surfactant monomers, for example, having surfactant tails, and having a solubility tailored for a given solvent or solvent system. This allows the surfactant monomers to bind cooperatively to the target. The surfactant monomers self-assemble around a target template. In one embodiment, the reactive monomers are preferably at a low enough concentration that a significant percentage are assembled on the template molecules. In one embodiment, the template molecules are preferably diluted to the point that when polymerization of the surfactant monomers is initiated, the created SPC shell is formed around one or a few template molecules. Additional crosslinking molecules may be used to alter crosslink density and thus structural rigidity, if desired. In one embodiment, the SPCs are nanomolecular structures which serve as soluble, unconnected individual recognition sites. In another embodiment, multiple target binding sites are located substantionally on the surface of the SPC. Because the target binding sites are on the surface the use of porogens to create channels or pores in the otherwise solid crosslinked network is not necessary.

In another embodiment, large SPCs ranging in size (average diameter) of about 0.1 to several micrometers may be used. The large SPCs advantageously can be designed to recognize and bind one to a few target molecules. The use of large SPCs permits large portions of cells and cell surfaces, such as bacterial surfaces, to be recognized.

Applications and Methods for Forming SPC's

The synthetic polymer complements can be used in many applications, including medical, pharmaceutical, agricultural and industrial applications. Agricultural applications include pesticides and insecticides. Industrial applications include waste removal and enzyme mimics. Industrial stabilized enzymes can be developed. Pharmaceutical applications include drug delivery, as well as therapeutic and diagnostic uses. The methods disclosed herein permit the formation of SPCs which are complex macromolecular networks and nano-structures. A wide variety of target specific materials may be synthesized. It is possible to create nano-networks with surfaces (either interior or exterior) that map the contour and surface energetics of a variety of targets.

The synthetic polymer complements can be used, for example, as therapeutic drugs, synthetic antibodies, either member of ligand-receptor complexes, enzymes and mimics, affinity chromatography matrices, stereo-isomer purification media, chelating extractants, and in other biologically active systems. Due to the need to purify optical isomers, affinity materials are desired that preferentially interact (dock) with only one of the enantiomeric pair. Purification of chirally-rich pharmaceutical compounds is a useful application of the synthetic polymer complements.

Several non-limiting applications are disclosed below. For example, the SPC-target complex may be used with or without separation from the target. The SPC may be used for drug discovery applications, wherein it optionally may be separated from the target. The SPC also may be used in other applications.

Applications: SPC-Target Complexes

High-Performance Enzymes

Naturally occurring enzymes are intrinsically fragile and generally remain active only over a narrow temperature and pH range in aqueous media. In order to extend the functional performance of naturally occurring enzymes, the SPC in one embodiment is formed as a thin shell. The thickness may range depending on the length of the monomer used, for example, from about 0.5 to 1 nanometer, or, e.g., 50 nanometers for very large monomers or extensive crosslinked shells. The SPC is formed as a complement capable of binding the target enzyme. The encapsulated enzymes reside in a thermodynamically stable "cage" including the hetero-assembled heads connected to the linkers that are an integral part of the crosslinked network. The stability against unfolding and denaturing of the internal protein is therefore greatly enhanced.

In one embodiment, the shell is designed to allow compatibility in non-aqueous environments. The polymerized synthetic polymer complements are used without extraction of the target. Thus, the complex of the target with the synthetic polymer complements is the desired product. The target remains trapped within the network of the synthetic polymer complement. The shell of the synthetic polymer complement provides protection and environment stability for the target. Such modified enzymes may be used in media traditionally considered too hostile and unsuitable for the naturally occurring substances. The activity of a variety of industrial and other enzymes can be enhanced. The SPC-enzyme complexes provide improved enzyme stability to conditions such as heat and organic solvents. Thus, the SPC-enzyme complexes may provide enhanced crude oil conversion, and a variety of thermally stable enzymes. The performance of, for example, detergent enzymes can thus be augmented. Clothing soiled by oily stains or grease can thus be effectively cleaned by high wash temperatures.

High Activity SPC-Enzyme Conjugates in Organic Solvents.

Some industrially useful enzyme substrates are not soluble in aqueous solution. However, the enzymes used to carry out the catalysis of substrates are only water soluble. Various methods of extracting enzymes into organic solvents rely on the use of organic soluble surfactants. Loss of enzymatic activity is the main problem with extracting aqueous enzymes into organic solvents. This is caused by the denaturing effects of both the surfactant and organic solvent on the enzyme.

It is desired to incorporate active enzymes in organic solvents and further desired to use those enzymes for catalysis at elevated temperatures where industrial processes can be more efficient. In one embodiment, an SPC polymer shell may be formed around enzymes that are solubilized in reverse micelles created from the injection of aqueous buffer/enzyme solutions into surfactants in organic solvent solutions. It is known in the art that some enzymes can be incorporated into reverse micelles and remain active (Shield, J. W., et. al., *Ind. Eng. Chem. Fundam.*, 25:603–612 (1986)). Potentially, the enzyme obtains a degree of stabilization from the interaction of the polar and non-polar moieties on the surface of the enzyme with the surface of the reverse micelle (R. S. Rahaman and T. A. Hatton, *J. Phys. Chem.*, 95:1799–1811 (1986)). Due to the transient and dynamic nature of reverse micelles (K. P. Ananthapadmanabhan, "Surfactant Solutions: Adsorbtion and Aggregation Properties" in *Interactions of Surfactants with Polymers and Proteins*, E. D. Goddard and K. P. Ananthapadmanabhan Eds., CRC Press, Boca Raton, pp 5–58 (1993)) this stabilization is fleeting and does not impart thermal stability to the enzyme-in-micelle structure. Without wishing to be bound by any theory, it is believed that by accurately recognizing the polar and non-polar surface moieties of the enzyme with a monomer set comprising recognition monomers and crosslinkable building blocks, enzymatic stability in harsh conditions is enabled by the subsequent crosslinking of the monomer building blocks and SPC formation. This hypothesis is supported by Klibanov's work as discussed in (Klibonov, et. al., *Biochemica et Biophysica Acta*, 485, 1977, 13–28). The enzyme is stabilized against denaturization by the support structure of the crosslinked SPC which recognizes and maps the enzyme surface. Since the SPC is crosslinked, it is not subject to the transient and dynamic fluctuations characteristic of reverse micelles. Thus a more durable stability of the enzyme is enabled by the SPC over the reverse micelle prior art. This stability is evaluated as the enzymatic activity in the presence of polar organic molecules, known to denature enzymes or as the activity either at increased temperature or after incubation at increased temperature. The thermal stability or polar organic solvent tolerance of the enzyme can be compared with different additives and assembly/polymerization procedures to evaluate SPC shell formation efficacy. Where recognition of the key surface elements on the enzyme is greatest, the imparted stability will be greatest.

Figure 21:
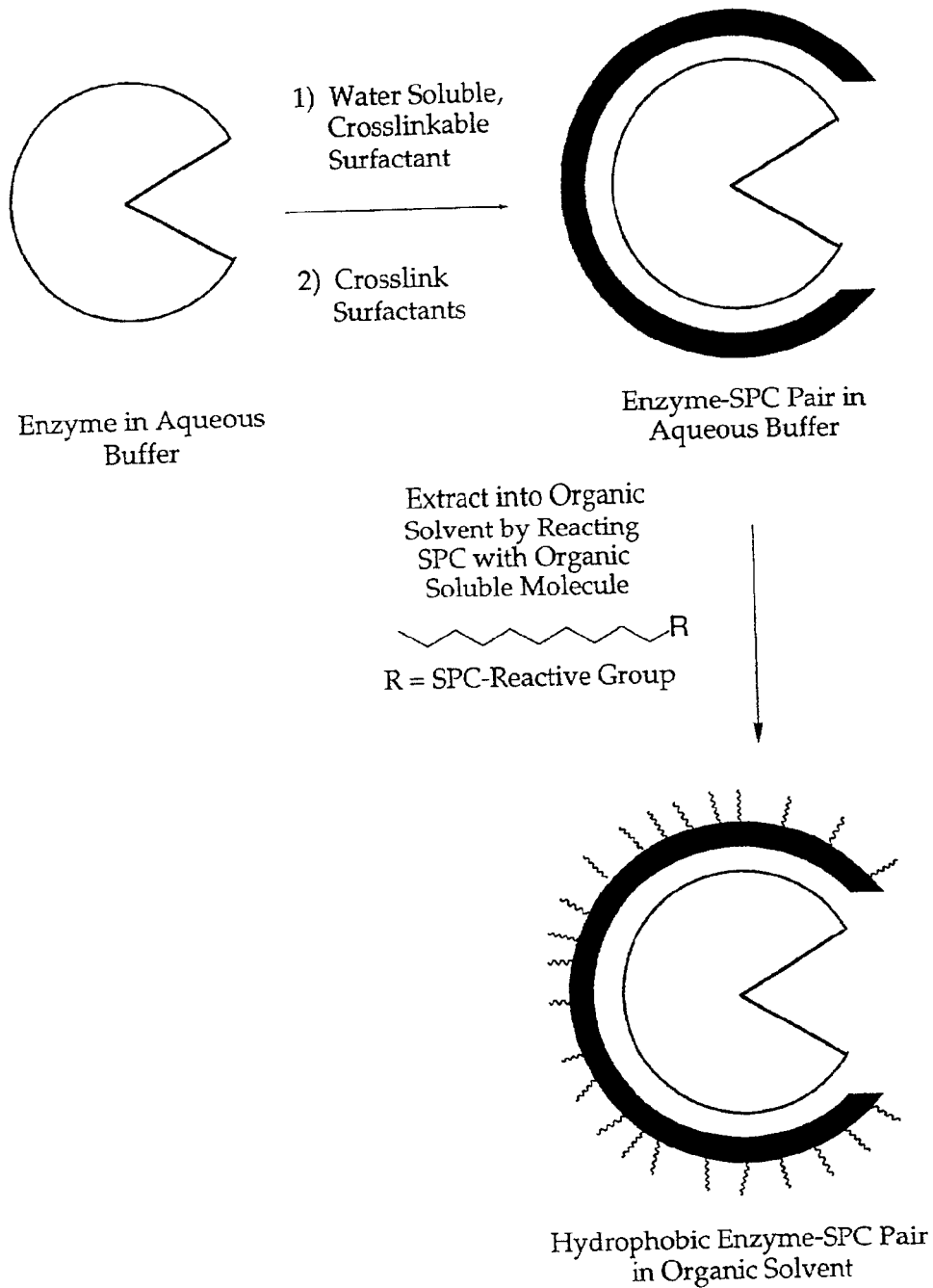
FIG. 21 illustrates schematically the complexation of an SPC around an enzyme target in aqueous solution, followed by chemical modification of the SPC with hydrophobic moieties to allow extraction into organic solvents.

FIG. 21 illustrates assembling another possible embodiment of the invention, that is the formation of an SPC around the enzyme target in aqueous solution and chemically modifying the SPC with hydrophobic moieties to allow extraction of the active enzyme into an organic solvent. The assembled SPC-enzyme pair is also more stable than the enzyme alone with the SPC acting as a stabilizing scaffold. The SPC protects the enzyme from denaturing during the extraction step.

A monomer set will be constructed comprising building blocks containing optionally either or both general recognition elements (headgroups) and specific recognition elements (headgroups) for the enzymatic target as preferred. Added to the monomer set will be multifunctional crosslinking building blocks to control the crosslink density at the desired preferably high level. In one embodiment the monomer set will include one or more reactive surfactants capable of supporting the enzyme in a reverse micelle invironment. In another optional embodiment the monomer set will include reactive building blocks that will work in conjunction with a non-reactive cosurfactant for the support of the enzyme in the reverse micellular environment. After assembly, the reactive components will be crosslinked together into a polymeric SPC supporting the enzyme in the organic solvent environment. The supported enzyme and SPC may be then used in the desired application.

SPC Formation Around α-Chymotrypsin

In one non-limiting example of this embodiment, the enzyme α-chymotrypsin (CMT) is solublized in reverse micelles. CMT posseses lysine residues on its surface, so specific recognition of CMT can be done by anionic heads such as carboxylate or sulfonate headed building blocks. Nonspecific recognition of CMT may be performed by amide hydrogen bonding heads as well as polar sugar headed building blocks. CMT is classified as a serine protease and CMT in organic solvents is known to catalyze transesterification of small peptide substrates. CMT activity may be monitored by measuring the rate of transesterification of N-acetyl phenylalanine ethyl ester (APEE) with n-propanol to N-acetyl phenylalanine propyl ester (APPE) by gas chromatography. Activity assays are performed at room temperature. CMT stability may be monitored by incubating SPC/CMT samples at elevated temperatures for specified periods of time before assaying them at room temperature. CMT stability may also be monitored by incubating SPC/CMT samples in organic solvents or solvent mixtures such as high n-propanol concentrations of 1 M or higher.

AOT-Based Systems

In one embodiment, an aqueous solution of CMT and hydrophilic monomers is added to an isooctane solution of AOT and reactive oil-soluble monomers. After a short stirring period, a clear reverse micellular system is obtained. There is some recognition of the CMT by the AOT surfactant in the base direct injection procedure, since there is charge complementarity between the anionic surfactant and the cationic surface lysine residues. This can be regarded as a baseline level of recognition and due to the uncrosslinked nature it is transient and fleeting. As the surface complementarity is increased between the shell/interior of the micelle (SPC) and the CMT located within by the addition of the monomer set containing crosslinkable components, the thermal stability or denaturing solvent tolerance of the encapsulated CMT can increase upon crosslinking of the building blocks. The monomer set in one embodiment comprises Span®-80 acrylate (in the oil phase at 1–100 mM, preferrably at 5–50 mM, most preferrably at 15–25 mM), acrylamide (in the aqueous phase at 1–50 wt %, preferrably at 5–50 wt %, most preferrably at 20–50 wt %) and methylene bis acrylamide (in the aqeueous phase at 1–10 wt %, preferably at 2–10 wt %, most preferably at 4–7 wt %) in conjunction with the non-reactive co-surfactant AOT.

Non-Ionic Surfactants

CMT-containing reverse micelles can be prepared using nonionic surfactant mixtures. See for example, Candau et. al., *Colloid & Polymer Science*, 271, 1993, 1055. These surfactants are useful in solubilizing high aqueous concentrations of ionic monomers in reverse micelles. For example, a surfactant blend having an HLB (hydrophobic/lipophobic balance, *Journal of the Society of Cosmetic Chemistry*, 5, 1954, 249) of 8–10 was reported as optimal for Candau et al.'s systems. (Higher performance is characterized as a lower amount of surfactant by weight needed to solubilize a given amount of a given monomer/water mixture.) Typically if the HLB was greater than optimal, performance was still good, but if the HLB was lower than optimal, performance was very poor. A 1:1 molar mixture of Span 83 and Tween 80 has an HLB of about 10.0, which is within the range of optimal HLB's and may be optionally used as a starting point for experiments.

In general, an oil phase is prepared containing mixtures of Span-83, Tween 80, reactive Span-80 acrylate and reactive polyethyleneoxy(20)sorbitan oleate acrylate (Monomer-Polymer & Dajac Laboratories, Feasterville Pa.). To this is added an aqueous phase containing enzyme, buffer and reactive building blocks such as sodium acrylate, acrylamide, acrylamidomethylpropanesulfonate salts, methacryoylethyltrimethylammonium chloride and crosslinkers such as methylene bisacrylamide, hexanediol diacrylate and polyethyleneglycoldiacrylate. Optionally the enzyme in buffer alone is added in a second stage after the aqueous monomer components. The components of the monomer set are then crosslinked into the SPC and the SPC-enzyme complex may be used in the desired application.

For Isopar M (Exxon Co. USA, Houston Tex.) (a $C_{14}$–$C_{15}$ aliphatic oil) as the continuous phase, about 10–100 mM of each surfactant (approximately 2.5–25 wt. % surfactant blend in oil) is needed, for example, for miscibility. When less surfactant is used, complex phase separation can be observed. The two stage direct injection method allows the co-solublization of polar monomers in the aqueous phase, thus creating an SPC shell around a target enzyme (CMT). Incorporated in the aqueous phase are acrylamide at 5–50 wt %, preferably 10–50 wt %, most preferably 30–40 wt %, sodium acrylate at 5–50 wt %, preferably 10–50 wt %, most preferably 20–40 wt %, and methylene bis acrylamide crosslinker at 0.1–15 wt %, preferably 1–10 wt %, most preferably 2–4 wt %, which may be combined into a direct injection of carbohydrate surfactants in oil phase (containing a small amount of oil-soluble UV photoinitiator). Subsequently buffered enzyme is added, with stirring. UV irradiated polymerization produces a transparent slightly viscous system. Activity is monitored by diluting the SPC/enzyme complex with APEE and n-propanol in appropriate surfactant in oil solutions and monitoring the conversion of APEE to APPE via gas chromatography.

Chymotrypsin and Modified Dextran Monomers

The assembly of monomer surfactants around a target can be entropically unfavorable since it requires the removal of many molecules from solution and immobilizes each surfactant based on only one head group to a single site on the target. By employing polymeric monomers with many copies of a head groups, the entropy of assembling many monomers around a target is replaced with the more favorable interaction of assembling one or a few multiheaded polymeric monomers around the target. Also, the strength of the interaction of the multi-headed polymer by binding multiple sites on a target is much more stable than monomeric interactions.

Polymerizable groups may be incorporated into the multi-headed polymeric monomer to form a dense shell (SPC) around the target. Any polymer with the ability to be selectively functionalized can be used as a multi-headed polymeric surfactant monomer. Dextran polymers with one or more compatible head groups can be used. Titration of the target with dextran with different head groups may be advantageous as stated above. Substituted dextrans and routes of synthesis of crosslinkable modified dextran are shown in FIGS. 19*b* and 19*c*. FIG. 19*b* is a schematic illustration of a monomer including a first tail region including dextran repeat units, for example, between one and 100 or 1000 repeat units, which may be covalently linked to crosslinking groups, head groups, or second tail regions such as hydrocarbon tail regions. FIG. 19*c* illustrates exemplary routes of synthesis of monomers including dextran repeat units.

FIG. 19*d* shows a dextran monomer of Formula 6, wherein $R_1$, $R_2$ and $R_3$ are independently H, or a moiety comprising at least one of a head group, a tail group, and a crosslinkable group, or combinations thereof, on any one or more of the saccharide units of the polysaccharide.

In one embodiment of the dextran monomer of Formula 6, on any one or more of the saccharide units of the polysaccharide, at least one of $R_1$, $R_2$ and $R_3$ is a moiety comprising a tail group, and, on any one or more of the saccharide units of the polysaccharide, at least one of $R_1$, $R_2$ and $R_3$ is a moiety comprising a crosslinkable group. Optionally, on any one or more of the saccharide units of the polysaccharide, at least one of $R_1$, $R_2$ and $R_3$ is a moiety comprising a head group. Optionally the head group of the dextran monomer may be one of the hydroxyls on the dextran moiety. The crosslinkable group may be, for example, substituted on the tail group. The head group may be, for example, alcohol, carboxylic acid, amide, amine, phosphonate or sulfonate. The tail group, may be for example, alkyl, for example a saturated or unsaturated, straight chain, branched or cyclic, substituted or unsubstituted hydrocarbon, e.g., $CH_3(CH_2)_n$—, where n is 7 to 20. The crosslinkable group may be, for example, —CH═CH—, —CR═CR—, $—O_2CCH═CH_2$, $—O_2CC(CH_3)═CH_2$, $—NRC(O)CH═CH_2$, $—NRC(O)C(CH_3)═CH_2$, $—C(═CH_2)—CH═CH_2$, or $—C_6H_4—CR═CH_2$, wherein R is alkyl, for example methyl, ethyl or propyl.

Dextran modified with hydrophobic tails increases the stability of a target enzyme such as CMT to a polar organic solvent, such as n-propanol, when the enzyme is extracted into the oil phase in the presence of a surfactant such as A-OT, when the hydrophobically modified dextran is added to the aqueous phase with the CMT prior to the direct injection. FIG. 38 is a reaction scheme showing the modification of dextran with acyl acid chlorides. FIG. 39 illustrates schematically the final superassembly. After the hydrophobically modified dextran has been assembled around the enzyme in the reverse micellular solution, it may be crosslinked to form an SPC, e.g., by radical or non-radical pathways. Thus, dextran can be modified with hydrophobic tails to provide a stabilizing effect in polar organic solvent and under heat stress. Examples include modified dextrans with hydrophobic tails covalently grafted (1:4) to 40 k dextran include 2-ethylhexyl (2-EH), oleyl (Ol), and octacosanyl (OC). The activity rises with added modified dextran and appears to level off for all hydrophobic chains around 300 glucose units per CMT molecule (~3 g modified dextran per 1 g CMT). This suggests that the identity of the hydrophobic chain on the dextran is not important in n-propanol stability. Rather, it is the dextran itself that provides polar organic solvent stability. The chains only help the dextran to be incorporated along with the CMT into the isooctane phase (dextran with no hydrophobic groups precipitates in isooctane)

Free-radical crosslinking is accomplished by attaching reactive groups such as acrylates or butadienes to the dextran via the well-known acyl acid chloride method (March, *Advanced Organic Chemistry*, 3rd ed., Wiley-Interscience, New York, pp. 346–347, 1985). The acrylate group is a fairly polar group and highly reactive. The butadiene group has the advantage of being fairly hydrophobic and is less reactive than the acrylate. These groups may be attached directly to the dextran or attached through a hydrophobic spacer. FIG. 40 illustrates exemplary radically crosslinkable tails that may be used. Synthesis of the acid chlorides of the radically crosslinkable groups is presented in FIG. 41.

Non Free-Radical Crosslinking Methodologies

Non free-radical crosslinking methodologies also may be used. For example, modified dextran (aminated and/or thiolated) can be synthesized that can be crosslinked with mild, commercially available crosslinkers. Aminated dextrans may be synthesized via the activator carbonyl diimidizole, as described in Bioconjugation Techniques, G. T. Hermanson, Academic Press: San Diego 1996, pp 183–185, and a diamine linker, as illustrated in FIG. 42. Thiolated dextran may be synthesized from the primary amine-substituted dextran via 2-iminothiolane as described in Bioconjugation Techniques, G. T. Hermanson, Academic Press: San Diego 1996, pp 57–59, as illustrated in FIG. 42. Aminated dextran may be crosslinked with disuccinimidyl gluterate, and thiolated dextrane may be crosslinked with bismaleimidohexane (both available from the Pierce Chemical Co.).

Conjugated CMT and Modified Dextran

Dextran may be oxidized to polyaldehyde dextran and lyophilized. The product is then conjugated to amines as depicted in FIG. 43. Three exemplary conjugates that may be synthesized include 1) CMT-dextran, 2) CMT-dextran-oleylamine, and 3) CMT-dextran-diaminohexane. Size exclusion chromatography of the product shows that the size of the CMT increased (table II), indicating success in the conjugation.

TABLE II

Molecular weight of CMT conjugates as determined by size exclusion chromatography.

| Conjugate | MW (SEC-HPLC) |
|---|---|
| CMT | 20 k |
| CMT-Dextran | 100 k |
| CMT-Dextran-Oleylamine | 68 k |
| CMT-Dextran-Diaminohexane | 83 k |

Use of Labile Covalent Bonds to Assist SPC Formation.

Figure 20A:
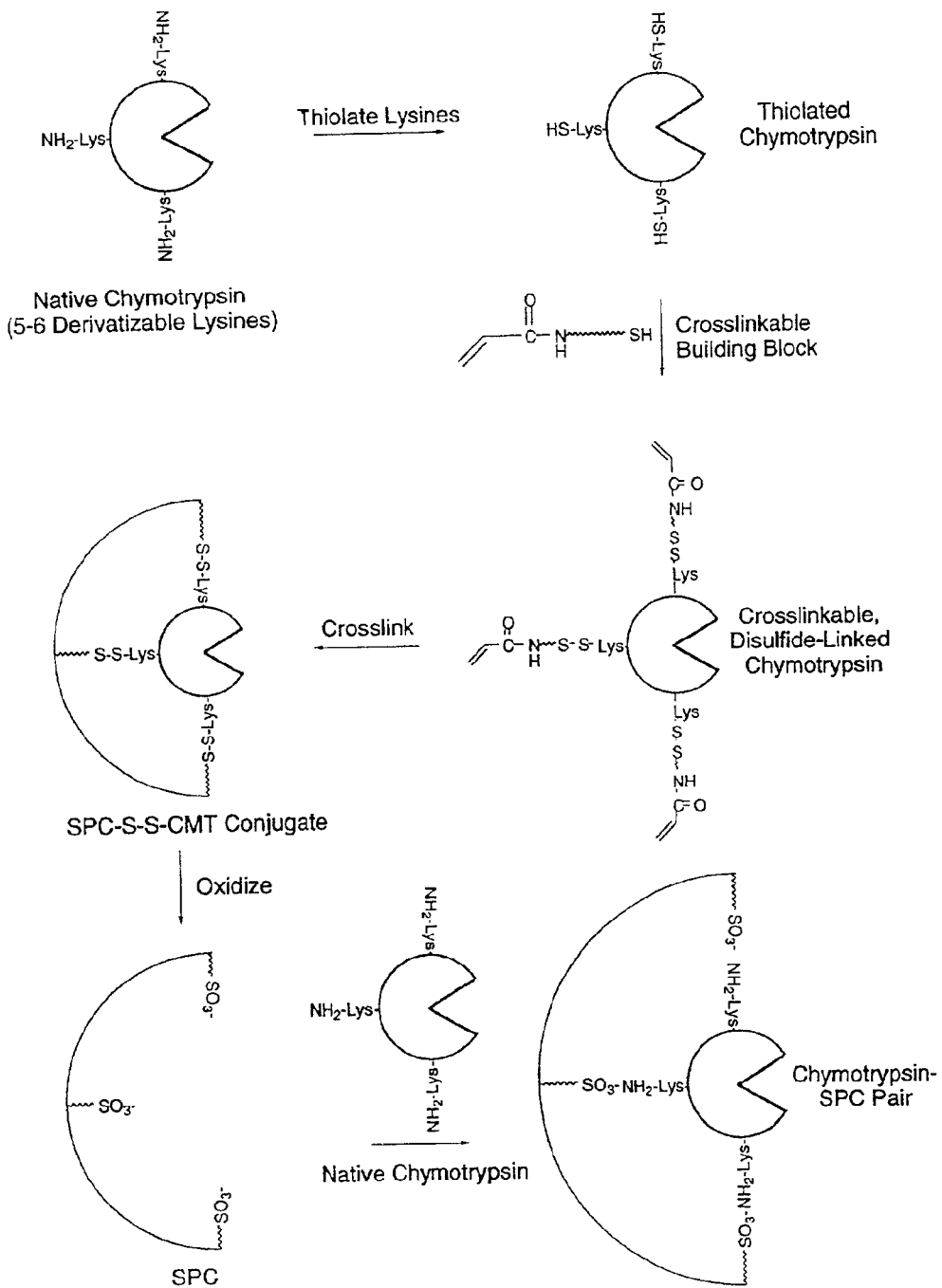
FIG. 20a is a schematic illustration of the assembly of monomers including thiol head groups on thiolated chymotrypsin to form labile disulfide bonds, followed by crosslinking of the monomers to form the SPC, and oxidation of the disulfides to sulfonates.
Figure 20B:
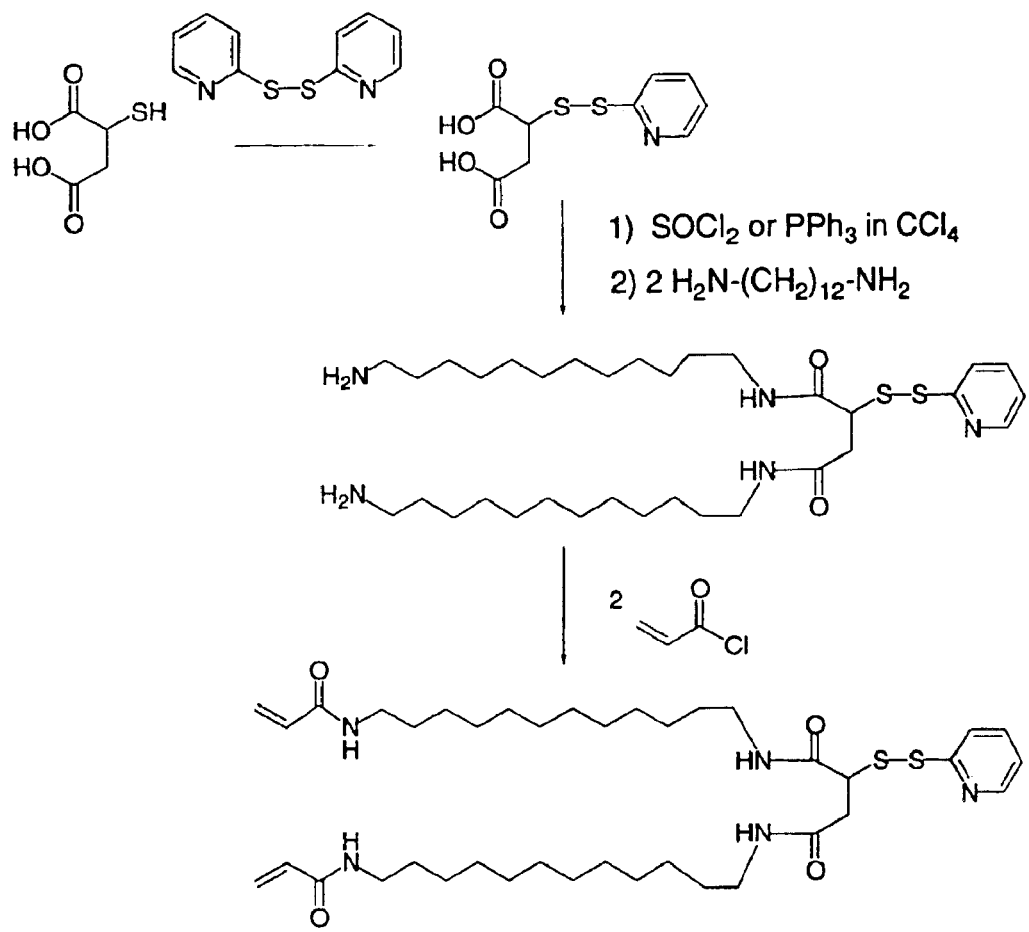
FIG. 20b shows schematically an exemplary synthetic scheme for producing a thiolated crosslinkable surfactant monomer.
Figure 20C:
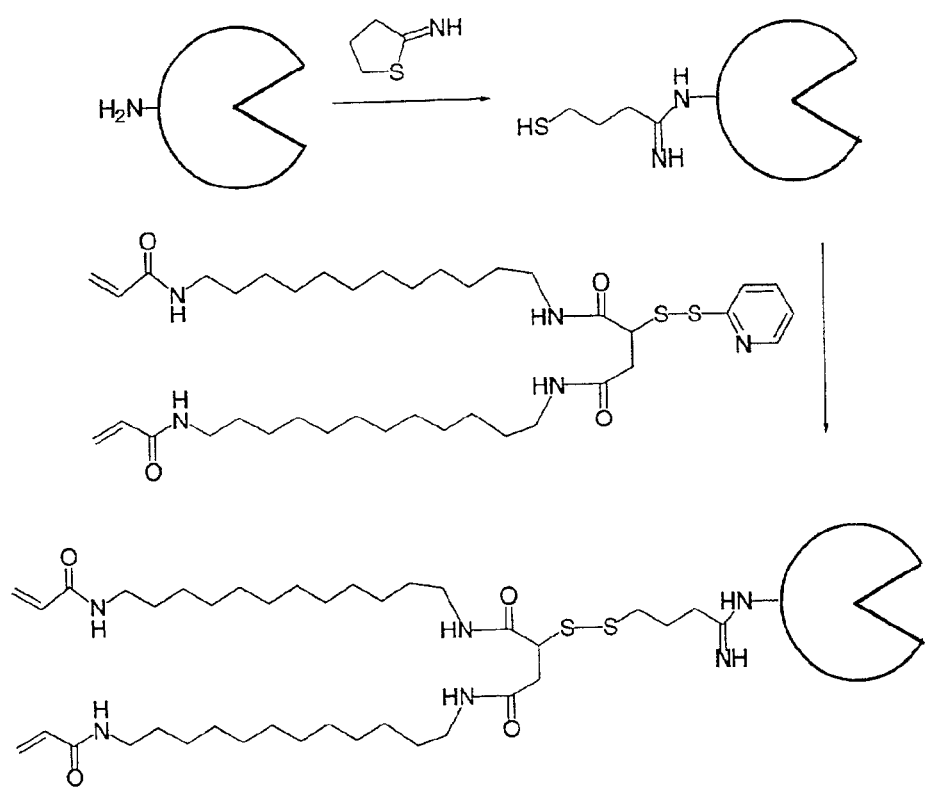
FIG. 20c shows schematically the synthesis of a conjugate of a thiolated crosslinkable surfactant monomer and chymotrypsin.

FIG. 20a illustrates this method of forming labile (oxidizable) disulfide bonds by attaching a thiolated and crosslinkable surfactant to the lysine residues on an enzyme for example, chymotrypsin (CMT). FIG. 20a thus is an illustration of a general scheme for the use of weak bonds (for example disulfides) to assist monomer self-assembly. This is followed by crosslinking the surfactant shell, oxidation of the disulfides to sulfonates. The anionic sulfonates are then suitably arranged to electrostatically interact with the cationic amines of the lysine residues on the native enzyme. FIG. 20b shows schematically an exemplary synthetic scheme for producing a thiolated crosslinkable surfactant monomer. FIG. 20c shows schematically the synthesis of a conjugate of a thiolated crosslinkable surfactant monomer and enzyme.

Protected Enzymes Used for Kinetic Resolution of Chiral Compounds

In another embodiment, an enzyme that is active in an organic media or an organic-water emulsion is used to purify chiral esters or alcohols. The enzyme preferentially catalyzes the conversion of one of the enantiomers, leaving the other unaltered. Also, because organic media and organic-water emulsions normally denature enzymes, the enzyme is protected from denaturing.

Racemic mixtures of ester and acid compounds are separated. While ester and acid compounds are described by way of example, the method may be generally applied to racemic mixtures with a variety of functionalities, if the enzyme catalyzes the modification of one of the enantiomers.

In one embodiment, when an organic phase only is used, both enantiomers are initially organically soluble esters. The enzyme preferentially saponifies one of the enantiomers. When a two phase emulsion is used, the eriantiomers may be initially esters that are soluble in the organic phase, or acids soluble in the aqueous phase. The enzyme catalyzes the saponification of the ester, or the esterification of the acid.

Figure 22:
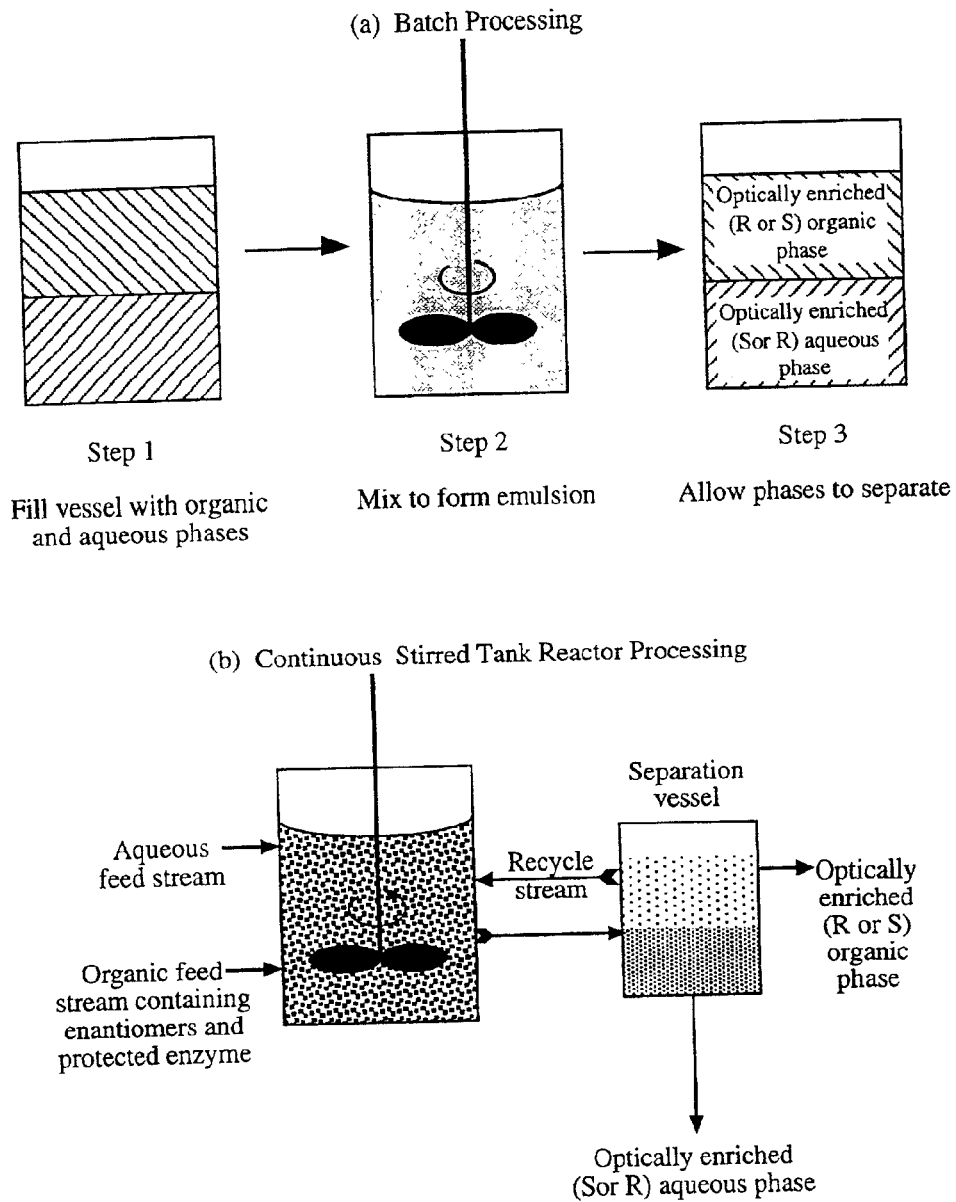
FIG. 22 is a schematic illustration of batch processing and continuous stirred tank reactor processing, for conducting stereochemical purification using an enzyme active in a water and organic phase microemulsion.

The saponification of an acid is implemented in a two phase process, which is illustrated in FIG. 22 for both batch and continuous operation. The enantiomeric esters in the organic phase are mixed with an aqueous phase, with the enzyme inhabiting the organic phase. The enzyme preferentially saponifies only one of the enantiomers. After saponification, the acid product is solubilized in the aqueous phase. The other enantiomer remains an ester solubilized in the organic phase. For purification ease, it is advantageous for the desired enantiomer product to be solubilized in one (aqueous) phase, while the enzyme remains soluble in the other (organic) phase.

The organic and aqueous phases are gravimetrically separated. The aqueous phase is enriched with the reaction product (R or S) enantiomer acid, and thus the organic phase is enriched with the unconverted (S or R) enantiomer ester. Various schemes can be employed to recycle the enzyme and further purify the enantiomers.

Enzymes are produced that are capable of retaining their activity in the emulsion environment, and are organically soluble, if it is advantageous to have the enzyme soluble in the organic phase. The SPCs provide a protective scaffolding. The scaffolding, in addition to supporting the enzyme structure in its native state, can provide solubility in organic solvents.

Figure 23:
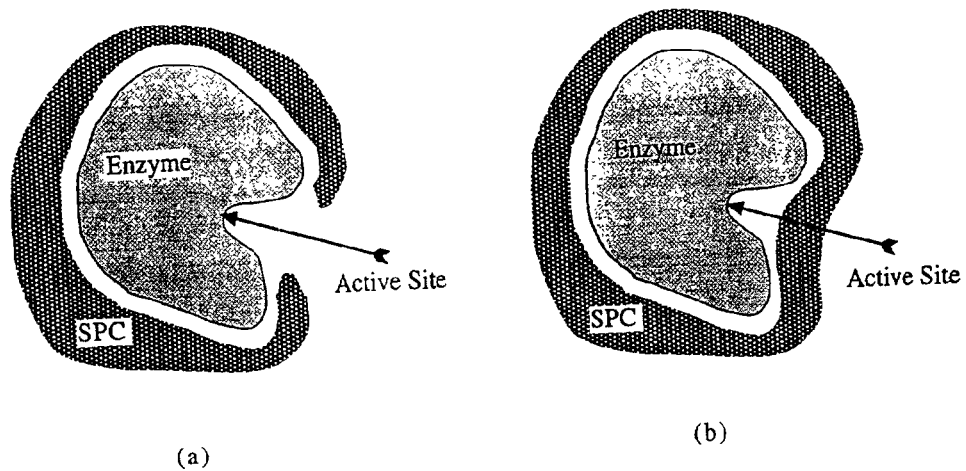
FIG. 23a is a schematic illustration of a protected enzyme complexed with an SPC, wherein the active site of the enzyme is accessible to substrate in solution.
FIG. 23b is a a schematic illustration of a protected enzyme complexed with an SPC, wherein the SPC covers the active site.

The protective scaffolding can have several architectures, and can be fabricated in several ways. An example method of fabrication is to use surfactant monomers that self-assemble around the enzyme. During assembly, surfactant head groups physically interact with complementary amino acid side chains of the enzyme. The surfactant monomers include polymerizable moieties which, after assembly, are polymerized to produce a stable SPC. FIG. 23a is a schematic illustration of the final product, a protected enzyme complexed with an SPC, wherein the active site of the enzyme is accessible to substrate in solution, FIG. 23b illustrates an alternate embodiment whereby the enzyme is completely surrounded by the SPC. This method of enantiomer purification is an improvement on a kinetic resolution method used by Sepracor (Malborough, Mass.; U.S. Pat. Nos. 4,800,162, 5,057,427, and 5,077,217). The Sepracor method immobilizes the enzyme in a membrane which separates an aqueous and an organic phase. In the present method, the enzyme is solubilized in the aqueous/organic emulsion, so the mass transfer limitations of the Sepracor method are substantially reduced.

Encapsulation of Therapeutic Agents

In another embodiment, targets consisting of therapeutic agents, such as proteins, are provided for use in therapeutic applications, wherein the therapeutic agent is provided within an SPC. Such therapeutic agents are referred to herein as protected therapeutic agents. For example, protected proteins may be provided within an SPC that are suitable for oral ingestion and inhalation delivery, and optionally injection, and their bioavailability can be adjusted by adjusting synthesis parameters such as choice of monomer and degree of crosslinking.

Advantageously, the use of an SPC permits stability of the therapeutic agent, such as a protein, to conditions such as within the human stomach where there exists a low-pH (acidic) environment, which can denature therapeutic proteins, such as insulin, rendering them inactive even after absorption by the intestine.

The use of SPCs is advantageous over the use of polymer gels or capsules, that may dissolve in the stomach, may be difficult to be absorbed by the gastrointestinal (GI) tract after transiting the stomach, or may have release rates that are difficult to control. Therapeutic agents may be provided within SPCs to provide a controlled release rate and protection of the therapeutic agent.

SPCs, for example, can maintain proteins in their "molecular dimensions". Since, in one embodiment, the protective sheath (SPC) is only a macromolecular "shell", the protected SPC/protein complexes can preferrably remain small and can be directly absorbed into circulation. The complexes may be for example, less than about 50 kDa. The SPC can be made to give networks of any desired tightness (or looseness). Bioavailability can thus be tailored for individual applications. In addition, the SPC material can be designed to have varying rates of hydrolytic degradation.

The SPC can also be designed to facilitate trans-membrane transport. In this regard, cyto-availability (concentration inside targeted tissue cells) can be elevated. SPC materials thus can be compatibile with the lipid bilayers constituting cell membranes. Polymerizable lipids (or micelle-forming surfactants) can be used for this purpose.

Alternatively, the SPC material can comprise other inert, non-toxic polymers. Modified dextrans are particularly useful as enzyme protectors. Other polymer networks can be fabricated around the therapeutic agents. Examples include other polysaccharides (modified to have tails and crosslinkable functional groups) and other water-compatible or water-soluble polymers, such as polyethylene glycol, polylactic acid, poly-galactic acid, and polyvinyl ether.

Thus, in one embodiment, individual protected, active, protein conjugates are provided that include a protective coating in the form of an SPC, which can have different degrees of hydrolytic stability, as well as controlled bioavailability in the plasma and in intra-cellular applications.

Synthetic Red Blood Cells

In one embodiment, a target may be used to form an SPC which is a synthetic red blood cell. For example, when the target is a porphyrin molecule, synthetic red blood cells with oxygen carrying capacity can be produced. The head groups in the SPC anchor the heme groups within the synthetic SPC, which are in turn biocompatible and dispersible in the blood stream.

Applications: SPC Recognition and Binding

SPCs can be designed which map, i.e., complement and bind specifically to, a particular binding moiety present in the body, such as all or a portion of a receptor, adhesion molecule, antibody, enzyme, hormone, neurotransmitter, phospholipid, liposaccharide, protein or other moiety. The bound or unbound SPC can be used as a pharmaceutical compound in drug discovery applications. These SPC's can be used to inhibit the action of the desired target. Alternatively, an SPC complement can be made of the target site and a second SPC can be made of the first SPC to produce an SPC drug containing a copy of the original target. Drugs for a variety of diseases can be developed, such as respiratory, dermatological, infectious, cancer, cardiovascular, ophthomological, metabolic, central nervous system, reproductive, inflammatory, digestive, and neurological diseases.

When the target is a polypeptide, the resulting synthetic polymer complements exhibit any of a number of biological functions, ranging from regulatory, promotional, adhesive, inhibitory, catalytic, to immunological behavior. For example, naturally occurring polypeptides can be used as simple neurotransmitters and hormones. SPCs made to recognize these functional polypeptides can be used to regulate bodily functions through the inactivation of certain biochemical pathways that are dependent on these polypeptides.

Synthetic Antibodies

When the target is a molecule such as a pathogen, an antigen, or a pharmaceutical agent, the synthetic polymer complement can bind the target in an analagous fashion to an antibody. Thus the SPC can be thought of an effective artificial antibody. This artificially created antibody is substantially pure and devoid of impurities present in host animal plasmas commonly associated with biologically produced antibodies. Furthermore, the antibody is made either chemically stable or unstable, susceptible or resistant to hydrolysis, enzymatic digestion, etc., by adjusting and selecting the components of the network formed by the crosslinked synthetic polymer complement.

Therapeutic uses of antibodies and additional bioactive agents disclosed below are well known in the medical field. The compounds may be used in research and administered to many species of animals and for in vitro studies. The compounds may be used in lab animals, farm animals, humans. The method of administration is standard for the pharmaceutical industry, for example, direct injection, absorption through the intestines after oral ingestion, adsorption through the lungs after inhalation, and a skin patch or subcutaneous implant. Suitable dosages and forms of administration are standard for the industry, for example, tablets, ointments, capsules or suppositories. Suitable carriers, adjuvants, diluents, buffers, flavoring agents, and binders are standard practices.

In Vivo or In Vitro Removal of Pathogens

Pathogens may be sequestered by the SPCs. SPCs may be used to help dispose of or signal the body's natural defenses to clear or destroy a pathogen. SPCs are administered to the body by routes of administration known in the art such as intravenous, by inhalation, topical, or oral administration.

The pathogen may also be sufficiently neutralized or deactivated simply through the disruption of pathogen function (e.g., binding to host cells) by bound SPCs. SPC binding can rely on the recognition of elements on the pathogen surface. For example, the entry of mammalian viruses into cells depends on specific recognition between the virus coat and proteins or carbohydrates that occur on the surface of mammalian cells. SPCs that interfere with this interaction, either at the virus coat or the cell surface, will block infection.

SPCs can be designed that specifically bind to all or a portion of a virus. For example, the SPC can bind to all or a portion of a viral nucleic acid molecule (DNA or RNA); a viral protein, or a viral lipid bilayer membrane (envelope). Exemplary viruses include a picoma viruses, such as the common cold virus, the Mengo virus, the poliovirus, and the foot-and-mouth disease virus. The SPC may bind a specific polypeptide of a virus, such as VP1 to VP4 of the picorna viruses.

In some cases the use of specific carbohydrates in the recognition pocket of the SPC can promote binding. For instance, the Influenza virus is roughly spherical with a 100 nm diameter. Its surface contains hemagglutinin protein that recognizes sialic acid residues (Wharton, S. A. et al. in *The Influenza Viruses*, Krug, R. M., Ed., Plenum Press: New York, 1989; p. 153). The hemagglutinin proteins are aggregated on the virus surface into triangular clusters. The clusters are distributed irregularly on the virus surface with a center-to-center distance between clusters of 10–15 nm. Incorporation of sialic acid residues in the SPC pocket at the appropriate concentration thus can promote SPC-virus binding.

SPCs can be designed that bind to bacteria, or to a portion thereof, such as the bacterial wall or portion thereof. The surface of a given bacterial cell changes in response to physiologic condition and to the stage in the life cycle of the bacteria. For instance, *E. Coli* sometimes displays pili, or long fibril hairs which possess carbohydrate binding proteins called lectins. The protruding pili substantially change the shape of the bacteria. SPCs can be designed to interact with the varying forms of bacteria and the surface molecules displayed by the bacteria.

Saccharide binding is one possible mode of interaction. The outer surface of the outer membrane of gram-negative bacteria is covered by a lipopolysaccharide. The outermost layer of the lipopolysaccharide consists of long projecting polysaccharide chains, with specific repeating units, that have antigenic properties and are called O antigens. Specific antibodies can be prepared against these polysaccharides. These polysaccharides are classified into 17 principle groups consisting of defined repeat units. At the inner end of the O antigen is a shorter polysaccharide chain whose structure is less varied than that of the outer ends. It contains two sugars found only in bacterial cell walls: a seven carbon heptose and an eight carbon α-keto sugar acid, ketodeoxyoctonate.

Gram-positive bacteria cell walls are composed of large amounts of teichoic acids (rebitolteichoic and glycerolteichoic acids) which, in some species, account for 50% of the dry weight of the cell walls. An SPC can be constructed which favors interaction with these saccharides.

An SPC with an interior lined with lectins (carbohydrate binding proteins) specific for bacteria polysaccharides can efficiently interact and complex with the bacteria surface. Conversely, an SPC recognition pocket coated with the appropriate carbohydrate can bind with lectins displayed on the pili of bacteria.

The SPC-bound pathogens can in one embodiment be designed to remain in the body as an inert entity that will eventually be degraded in the body. The SPC-pathogen complex can be also be cleared and/or inactivated by the body's natural defense system by a variety of mechanisms. The pathogen may be made large enough (particulate) by the binding of SPCs to its surface so as to be recognized by host macrophages and be cleared by phagocytosis. This may be achieved by binding one or many SPCs to a pathogen, by employing multivalent SPCs which cause agglutination of the pathogen particles, or by the use of large scale (1–2 mm) SPC's. In addition, phagocytosis of an SPC-coated pathogen can be facilitated by pre-coating the SPC with proteins or polysaccharides (artificial opsonization) that attract or activate phagocytes through the complement or properdin defense systems, resulting in lysis of the pathogen.

Through the attachment of various components to the SPCs, it is possible to activate either the humoral or cell mediated immune responses of the body to target the bound pathogen for destruction. The humoral system may be activated by attaching the Fc region of antibodies to pathogen-specific SPCs. Killer cells can then recognize the SPC-coated pathogens as foreign and destroy them. A cell mediated response may be induced by attaching harmless pathogen antigens to the SPCs. After binding to the pathogen, cytotoxic T cells recognize the viral antigens presented on the SPC and cause the destruction of the pathogen.

SPC-coated pathogens may be removed at a later time from the body through an adsorbate with a specifically designed chemistry which binds moieties incorporated on the SPC (e.g., biotin-modified SPCs may bind to avidin-coated solid supports).

SPC's may also be designed to be removed from the body after a certain lifetime. As with polymeric entities used for drug delivery applications, SPC's may be removed or eliminated by degradation, renal filtraton, immunogenic reactions, and inactivation reactions by blood enzymes as disclosed in C. Monfardini and F. M. Veronese, *Bioconjugate Chemistry*, 9:418–450 (1998).

Pathogens enter and infect the body through the excretion of various toxins that aid in the invasion. SPCs specifically designed to bind these toxins can disrupt the pathogen's infection and render it harmless.

SPC Usage for Cancer Diagnosis and Therapy

Any target for antibody and immune system therapy is a potential target for SPC synthesis. In one embodiment, a secreted or surface bound molecule of a tumor is a target. Example epitopes may be found on the following antigens.

Useful targets include antigens presented in tumor cells, such as α-fetoprotein (AFP) in liver cancer and carcinoembryonic antigen (CEA) in colon cancer, that are normally present only during fetal development.

Useful targets include normal antigens over-expressed in tumors, or expressed antigens that are found on normal cells in other tissue. Thus, antigens such as CA 125 (ovarian cancer), CA15-3 (breast cancer), and PSA (metastatic carcinomas of prostatic origin) are targets.

Tumor antigens are often more highly glycosylated than normal cells, sometimes with unique saccharide sequences. Thus, normal and unique carbohydrate epitopes may serve as targets.

An additional route to tumor cell recognition is enabled through the use of cellular dimensioned SPCs. Tumor cells often present normal antigens at abnormally high or low surface concentrations. Also, tumor cells may have distinctive sizes and shapes. Thus, large (of cellular dimension) SPCs may be used to recognize the distinct antigen surface densities of tumor cells, or the abnormal size and shape of tumor cells, as illustrated in FIG. 24. This application is enabled through the use of large structures such as an SPC, and is not possible through the use of smaller therapeutic molecules such as monoclonal antibodies.

For in vivo imaging of tumors, radiolabels, ultrasound spheres, and MRI contrast agents can be attached to the SPCs. Exemplary ultrasound spheres 20 (hollow spheres, typically filled with air or a flouromolecule such as octafluoropropane, that alter the density of the tissue to which they are attached or into which they are incorporated) with attached SPC elements 10 are shown in FIG. 28.

SPCs can be formed that are active, with long shelf lives, and that inhibit growth, deliver toxins, and activate the immune system. Antigens that are known to provoke a strong immune response may be attached to the SPC. Similarly, toxins may be attached for delivery directly to a tumor. An SPC-mediated approach can proceed through such methods as one or more of the following. When distinct antigens are present, cancer cells may be made large enough (particulate) by the binding of SPCs to their surface so as to be recognized by host macrophages and be cleared by phagocytosis. This can be achieved even when no costimuli are presented, for instance by binding one or more SPCs to a tumor cell or by employing multivalent SPCs which cause agglutination of the particles. In addition, phagocytosis of an SPC-coated cancer cell may be facilitated by pre-attaching polysaccharides (artificial opsonization) to the SPC that activate phagocytes through the complement defense system, resulting in lysis of tumor cells. Tumor cell proliferation may also be sufficiently deactivated through the disruption of cancer cell function by binding SPCs to appropriate receptors.

SPCs can be specifically designed to bind secreted proteins such as cytokines and disable their function. For example angiogenesis may be largely inhibited with the proper SPC.

Through the attachment of various components to the SPCs, it may be possible to activate either the humoral or cell mediated immune responses of the body to target the bound cancer cell for destruction. Attachment of a strongly immunogenic antigen plus the necessary costimuli molecule (s) to the SPC may precipitate a cell-mediated immune response. Here, the SPC is a multifunctional molecule, with an antigen binding functionality and immune system stimulating functionalities. Similarly, the humoral system may be activated by attaching the Fc region of antibodies to cancer cell-specific SPCs. Killer cells can then recognize the SPC-coated cancer cells as foreign and destroy them.

SPCs may be used for solid phase separation of tumor cells from autologous stem cell preparations.

Large Biological Particle Recognition

A relatively large SPC may be complementary to a large portion of a "bio-entity", or "biological particle", which as used herein, includes multi-molecular biological structures such as a virus, a bacterium, or a cell. The concept is illustrated in FIG. 24. Large-scale (micron) envelopment of a bio-entity by an SPC is advantageous.

Figure 29:
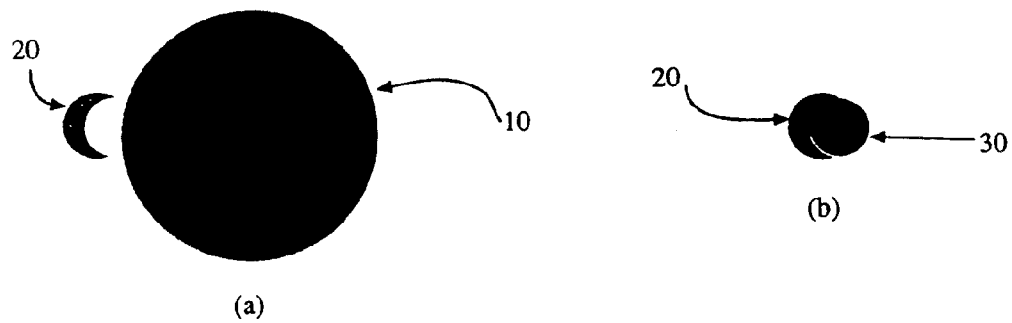
FIG. 29 is a schematic illustration of an SPC binding to a biological particle.

The shape of the bio-entity can serve as a basis for recognition. Binding sites may not be accessible to untargeted bio-entities with the same surface receptors as the target. For example, if a virus and a normal cell both present an antigen, an antibody to that protein can bind to the cell and the virus. As illustrated in FIG. 29, an SPC 20, with shape recognition, on the other hand, can only bind to the virus 30, and not to the cell 10. The shape of the SPC thus allows a greater targeting precision.

Concentrations and/or patterns of surface entities, rather than individual entities, serve as a basis for recognition and binding.

The specificity of the binding of SPC surface elements to target surface elements can be less than would be necessary for binding of the elements if they were individually solvated, rather than multiply attached to a surface. The lower specificity of the individual elements attached to the SPC is allowed by the same multidentate binding mechanism that on a smaller size scale enables antibody—antigen binding and small SPC binding to a small target. The additive effect of multiple low energy binding sites produces an exponential increase in the binding strength of the complex, as described earlier in Equation 1.

The SPC structure can serve as a drug delivery device. SPCs may be fabricated in sizes ranging from nanometers to micrometers are used to deliver drugs in a controlled fashion. If the particles are small enough to circulate and are intended to target specific tissues or cells, molecules such as adhesion molecules, lectins, and monoclonal antibodies may be used to target the SPCs.

Viruses and bacteria may be incapacitated, or neutralized, and tumor cell proliferation may be retarded through SPC binding. Additionally, SPC binding may be used to rapidly destroy the bio-entity, or may enable destruction of the bioentity by the active or passive immune system. Large SPC complexation with viruses, bacteria, and cells may be used.

Tumor cells often display normal antigens at abnormally high or low surface concentrations. Also, tumor cells may have distinctive sizes and shapes. Thus, large (of cellular dimension) SPCs may be used to recognize the distinct antigen surface densities and surface patterns on tumor cells, and, when applicable, the abnormal size and shape of tumor cells.

Whole cell recognition, rather than the reliance on recognition of individual antigens, is enabled through the use of large structures such as an SPC, and is not possible through the use of smaller therapeutic molecules such as monoclonal antibodies.

The ability of large SPCs to penetrate the tumor mass is a primary concern in therapeutic and diagnostic applications. Because tumor vasculature is often "leaky", the transport of large SPCs is made possible.

Methods for the Formation of Large SPC Structures

In the formation of the SPC, monomers are assembled on the target. When the monomers are assembled on a target, such as a particle and crosslinked to form the SPC, the monomers and the resulting SPC may entirely or may partially cover the target, such as a target particle. The term "particle", as used herein, includes bio-entities (also referred to herein as biological particles) such as viruses, prokaryotic cells, including bacteria, and eukaryotic cells including mammalian cells, as well as silica and polymeric particles including microparticles, nanospheres and microspheres.

If desired, the degree of envelopment of the SPC around a particle target can be reduced through the attachment of the particle to another particle or a macroscopic surface prior to SPC formation. The covalent attachment of a particle to a flat surface can detrimentally permit more of the particle surface to be covered by the SPC, as illustrated in FIG. 27*a*, which impedes SPC release after formation. To reduce the amount of surface of the particle covered by the SPC, the target particle may be placed within a material such as a polymer, as shown in FIG. 27*b*. Exemplary methods are described herein below.

In one embodiment, particles are added to spin coated film. The spin-coated layer may be used to provide a layer in which a particle may be partially immersed.

In one embodiment, the spin coated polymeric film is formed on a substrate. The solvent is not allowed to be completely evaporated away. A particle solution is added onto the film, and the particles allowed to sink into the swollen film. The film is chemically crosslinked. The film, and optionally, the particles, may be chemically attached to the substrate. The solvent is removed. This method produces particles imbedded in a film, as illustrated in FIG. 27*b*.

Optionally, the particles may be added to the spin coating fluid along with the film precursors prior to spin coating.

In these embodiments, the spin coating solution may be, for example, water with a hydrophilic polymer, such as PEG, dextran, or cellulose. Carbohydrates such as dextran are preferable in one embodiment, because the surface can be subsequently made hydrophobic through reactions (e.g., using alkyl acid chlorides or activated esters) with the hydroxyl moieties. The particle preferably is not reactive with the hydrophobic agent. Water-based systems are preferable in one embodiment to promote the use of viral, bacterial, and cellular templates. Hydrophobic modification of the film without similarly modifying the biological particle may be implemented, for example, by functionalization of the dextran prior to film formation with a moiety that permits hydrophobic modification after film formation.

In another embodiment, small target particles may be immobilized on a surface such as a glass plate without the use of a spin coated polymeric film prior to assembly of the monomers on the target and formation of the SPC. The resulting SPCs may be viewed with an electron microscope, microscopic, fluorescent, or inspection. In another embodiment, to increase surface area and thus the number of SPCs that can be produced, the particles may be attached to a high surface area structure such as a capillary array.

Particle attachment to a glass plate is illustrated in FIG. 25. In FIG. 25, particle targets 10 are attached to surface 20, a monomer set is assembled around the targets and then are polymerized to form SPCs 30 that are subsequently released from the surface. In one embodiment, the surface of the target particles includes a moiety, X, and the glass surface includes another moiety, Y, wherein X reacts with or binds to Y, but X does not react or bind with X, or Y with Y. The target particles are contacted with the glass surface. The target particles may be applied in solution at a concentration such that after attachment to the glass surface, a desired surface concentration is achieved. The target particles including surface X moieties are reacted with or bound to to glass surface Y moieties. Optionally, the particle-surface structure is further processed to provide the desired chemical properties. For example, the macroscopic glass surface can be functionalized with hydrophobic moieties and the target particles can be functionalized with hydrophilic moieties. SPC fabrication can then proceed with monomers that have an affinity for the particles.

SPC Formation Around Particles SPCs may be formed around particles using a variety of methods. Exemplary methods are discussed herein below.

In one embodiment, a microemulsion assembly method may be used, using monomers in an aqueous phase, to form a large hydrophilic SPC's on immobilized particles. Exemplary procedures are described below.

In one embodiment, a solution of monomers, for example in an aqueous solution (plus surfactant, if desired) is applied to the surface-immobilized particles. The aqueous solution is preferably of a quantity to easily cover the particles and such that water evaporation will not cause the solution composition to change substantially prior to the next step. An organic solvent/surfactant solution is then added such that a water in oil microemulsion forms. The solution is gently agitated so that the microemulsion forms without dislodging the particles from the surface. The monomers then are polymerized to form the SPCs. The SPC-surface immobilized particles then are removed from the polymerized microemulsion solution. The hydrophilic SPCs are then removed and collected using an aqueous solution and, if necessary, heat, a change in pH, and/or destruction of the template particles.

In another embodiment, a microemulsion solution is formed containing the desired monomer building blocks. Surface immobilized particles then are immersed into the microemulsion solution. Hydrophilic components are permitted to coat the hydrophilic particles. The monomers then are polymerized to form the SPCs. The SPC-surface immobilized particles then are removed from the polymerized microemulsion solution. The hydrophilic SPCs are then removed and collected using an aqueous solution and, if necessary, heat, a change in pH, and/or destruction of the template particles.

In another embodiment that does not employ microemulsions, a surface such as a plate or slide with attached particles is immersed in an organic solution containing a reactive surfactant, such as the custom-synthesized benzoic acid based surfactants discussed herein. The hydrophilic heads of the reactive surfactant are attracted to the hydrophilic moieties, e.g. hydroxyl, amine and/or carboxylic groups, on the particle surface. A monolayer of the reactive surfactant thus forms on the particle surface, with hydrophobic tails projecting away from the particle surface. The plate is then immersed in a dilute aqueous solution with water-soluble building blocks, such as PEG diacrylate. The hydrophobic tails of the reactive surfactants keep the building blocks surfactants in place on the particle. Because there is a higher concentration of polymerizable moieties at the surface due the reactive surfactant monolayer, polymerization proceeds at the surface of the beads, with the bulk solution monomers adding to the growing surface polymer. The monomers then are polymerized to form the SPCs. The SPC-surface immobilized particles then are removed from the polymerized microemulsion solution. The hydrophilic SPCs are then removed and collected using an aqueous solution and, if necessary, heat, a change in pH, and/or destruction of the template particles.

Biological particles, such as viruses, bacteria and cells may be tethered to an immobilizing surface through such techniques as PEG linkages from the surface to lysine residues. Assembly can then proceed as discussed above. Methods such as those discussed above, where the particles are initially immersed in water, and during processing may remain immersed in a water shell, are preferred for SPC formation with biological particles that are biologically active.

Complex biological structures are susceptible to destruction when exposed to surfactants and organic solvents. In one embodiment, target structures which emulate the intended target in size, shape, and surface chemistry, but which are more stable to surfactants and organic solvents, are used for the formation of large SPCs. These structures are referred to herein as biological particle substitutes. The substitutes may be used as targets to form SPCs that that can bind specifically to a wide range of biological particle targets including viruses, bacteria, and molecules such as proteins, nucleic acids and polysaccharides.

In one embodiment, the particle may be a substitute for the influenza virus. The influenza virus is roughly spherical with a 100 nm diameter. Its surface contains hemagglutinin protein that recognizes sialic acid residues (Wharton, S. A., et. al. in *The Influenza Viruses*, Krug, R. M., Ed., Plenum Press: New York, 1989, p. 153). The hemagglutinin proteins are aggregated on the virus surface into triangular clusters. The clusters are distributed irregularly on the virus surface with a center-to-center distance between clusters of 10–15 nm.

Microspheres (such as those made of silica or polystyrene) of 100 nm diameter may be employed for the fabrication of SPCs which bind to targets such as the virus. Such particles are commercially available (sources include Polysciences, Inc., Warrington, Pa., and Bangs Laboratories, Inc., Fishers, Ind.) with functionalities that allow the facile attachment of proteins such as hemagglutinin. SPC fabrication can proceed around the hemagglutinin-coated particles using monomers which incorporate an approriate percentage of sialic acid moieties. Incorporation of sialic acid residues in the SPC pocket at the appropriate concentration will promote SPC-virus binding. Any of a variety of surface moieties, such as carbohydrates, poly(amino acids) and nucleic acids may be attached to the surface of particles such as inorganic particles or organic polymer particles to fabricate the biological particle substitutes.

Circulation and Half-Life of SPC Structures

SPC substances may be designed and synthesized that remain in circulation long enough to find and bind targets in vivo diagnostic and therapeutic applications. In one embodiment, the SPC binding to the target occurs on a time scale shorter or similar to clearance of SPC from circulation. SPC particle may be eliminated from the body through phagocytosis or cytotoxic agents. Circulating 1–2 $\mu$m sized particles are cleared efficiently in minutes via phagocytosis, while particles too large for phagocytosis are destroyed in a slower process through cytotoxic agents that are released into the intracellular space. SPCs larger than a few microns will thus be too large for phagocytosis, and will remain in circulation for longer periods of time. SPCs can be constructed with this in mind.

Enzyme Mimics

When the target is a a transition state analog of a substrate molecule (of a metabolic pathway, known to be catalyzed by an enzyme), the resulting nano-engineered SPC can itself possess enzymatic activity and act as an enzyme mimic. The enzyme mimic can include covalently bonded networks, and therefore the thermal stability and solvent resistance may be designed to be far superior to naturally occurring enzymes. These types of highly stable and resistant enzymes are useful in high temperature industrial applications in aggressive media (oil phase).

Uses of these enzyme mimics also include animal and plant applications, research use in laboratories and therapeutic drugs and other applications where enzyme mimics are useful.

Laboratory Subtraction/Affinity Chromatography

For a variety of targets, including DNA or RNA (viral, bacterial, mammalian or human in origin) the SPCs can be used to remove the target, such as a DNA or RNA, from the blood plasma or other body fluids by passage through a packed bed of beads coated with SPCs. For example, the SPC can be tethered to polystyrene or silica beads, and then the tethered complex can be used in column separation.

The SPCs may be used in one embodiment for stereoisomer purification.

An important concept in the field of chemistry is stereoisomerism, also known as chirality. An optical isomer pair is also referred to as enantiomers or stereoisomers. By definition, enantiomers must possess asymmetric centers. Pharmaceuticals, agro-chemicals, flavors and fragrances contain many naturally occurring or synthetic stereoisomers. However, the pharmacological activities of distinct enantiomer pairs may be drastically different. For example, enantiomers may be comparable in activity and potency. Enantiomers may have similar activities but different potencies. Enantiomers may have different activities, one beneficial the other detrimental. Additionally, all activities may reside in one isomer, while the other isomer acts as an impurity (diluent).

When the target is an optically active drug or drug candidate, the synthetic polymer complements are useful affinity chromatography packing materials with stereospecificity. Exemplary drugs and intermediates include carvone, asparagine, chloramphenicol, propranolol, thalidomide, ibuprofen, diltiazem, glycidyl butyrate, amino acids, chloropropionic acid, mannitol, glucose, chiral amines, 6-APA (a penicillin precursor), levodopa, and menthol.

Small Molecule Recognition

The identification, capture and release of a small molecule target is possible using a synthetic polymer complement (SPC). The SPCs for small molecule target recognition are fabricated from monomers that are synthetically prepared or are commercially available. The monomers may be selected and designed for the specific moieties on each target to be recognized, but can also have general recognition features to permit unanticipated or non-specific interactions. In this embodiment, the SPC is capable of specific binding to a target analyte. The building blocks comprising the monomer set in general are selected and assembled to allow interaction with the target molecule. The building blocks then are crosslinked together to create the SPC. The target is then extracted from the SPC-target complex and the SPC used for target binding applications. The small molecule recognition process may be implemented, by the non-limiting examples of dilute solution-continuous experiments and latex surface target recognition sites.

Method of SPC Formation: Dilute Solution-Continuous Model

Non-covalent interactions, such as ionic bonding, hydrogen bonding, aromatic stacking and hydrophobic association can thermodynamically drive the self assembly of monomers. An optimal concentration range may be selected for a solution-continuous phase polymerization to form molecular sized SPC structures. In known crosslinked solution polymerizations (gelations), at a certain dilute concentration and below, soluble microgels are formed rather than monolithically crosslinked macrogels. Antonietti et al., *Makromol. Chem., Macromol Symp.*, 30:81–93 (1989). The molecular weights of the microgel fragments range from a few tens of thousands to millions and remain in solution as soluble entities. In this embodiment, the SPC is formed preferably as a soluble entity, therefore operating in the concentration range of microgel synthesis.

A monomer set is constructed comprising building blocks with general recognition, building blocks with specific binding to elements of the target and multifunctional crosslinking monomers. The components are selected so that the formed SPC is soluble in the desired application solvent(s). Solution complexes of targets and the monomer set are self assembled and crosslinked at a concentration low enough to maintain the crosslinked SPC as a soluble microgel. A preferred concentration of the monomer set is just below the solution gel point. After the SPC's are prepared and purified, their concentration can be increased or decreased as desired for different applications.

Method of SPC Formation: Latex Surface Target Recognition Sites

In one embodiment, SPCs may be designed that include a plurality of binding sites (or recognition sites) for the target. The number of binding sites may be adjusted, for example, by choice of monomers and reaction conditions. SPCs may be formed, for example, that include: about 1 to 1000 sites; about 20 to 1000 sites; about 100 to 1000 sites; greater than 20 sites; greater than 50 sites; greater than 100 sites; or greater than 1000 sites, for different applications.

In this embodiment, the monomer set includes monomers that include a crosslinking group, but not a head group, in addition to monomers comprising the head groups. The monomers without a head group thus crosslink to form sites on the SPC which separate the target binding sites, and also serve to increase the bulk or size of the SPC. These are referred to as latex SPCs.

Target recognition sites in one embodiment can be envisioned as "dimples" or defects on the surface of a crosslinked polymer latex bead. Since latexes are thermodynamically stable dispersions of polymer particles in solution, they resemble soluble species. Latexes are prepared via oil-in-water microemulsions or inverse water-in-oil microemulsions. The size of the particle can be controlled over a wide range, for example, from approximately 5 nm to 100 mm depending on the conditions. Methods known in the art may be used, for example to prepare 50 nm or smaller oil-in-water microbeads (M. Antonietti, *Macromol. Chem. Phys.*, 196: 441–446 (1995)). In one embodiment, the latex particle is the SPC and has from one to 1000 recognition sites on the surface. The latex is prepared in the presence of the preferrably amphiphilic target molecule, thus creating the recognition sites in the surface of the latex. Sets of monomers to form the latex SPCs are provided that form a microemulsion, wherein the monomer set comprises monomers with at least one crosslinkable group that do not have head group. These monomers orient in the core of the micelle or reverse micelle structure. Monomers with head groups orient on the surface of the SPC and are thus available to bind with complementary target moieties. A surfactant is used to stabilize the microemulsion. The surfactant may or may not have a crosslinking moiety. This monomer set then is formed into a microemulsion where the two phases are substantially the monomer set and substantionally continuous solvent. The monomer set optionally includes reactive surfactants for the stabilization of this microemulsion of the monomer set and target in a solvent. The monomer set will optionally be used with a non-reactive cosurfactant for the stabilization of the precursor microemulsion of the monomer set and target in a solvent. The microemulsion phase behavior of the monomer set components (including the interactions with the optional non-reactive cosurfactant) in both the monomeric and polymeric forms are designed to controllably form dispersed latex particles of, for example, a size (average diameter) of about 5 nm to 400 nm, depending on the desired application.

In one embodiment, a set of monomers which forms an oil in water microemulsion for forming a latex SPC is provided, wherein the monomer set includes styrene and divinylbenzene, which make up the core of the micelle in an oil in water microemulsion system; vinyl benzoic acid in which the acid or the carboxylate ion is the head group which can interact with a target; and hexadecyltrimethylammonium bromide which stabilizes the microemulsion and the polymerized latex.

The target molecule may be added to the microemulsion, wherein the target molecule is amphiphilic and thus will inbed in the micellular surface, wherein the target is added at a concentration such that upon polymerization there will be from 1 to 1000 target binding sites on the surface of a latex SPC. The styrenic crosslinking groups then can be reacted through a free radical reaction, for example, wherein UV light and photoinitiator(s) such as Darocur 1173 and Irgacure 907 are used.

The target is in one embodiment preferably amphiphilic. Non-amphiphilic targets may be incorporated into the invention by the prior conjugation of the non-amphiphilic target to a moiety of the opposite solvophobicity, thus creating an amphiphilic target. For example a polar polyethyleneglycol chain may be conjugated to a hydrophobic steroidal target compound. After incorporation into the microemulsion the target will orient at the interface between the two phases of the microemulsion. The recognition elements of the monomer self assemble around the target and subsequently the monomer phase is crosslinked into the SPC. In this process, the recognition elements of the monomer set will be crosslinked into place creating specific binding sites for the target analyte. The target analyte is then extracted and the purifed SPC's are used for binding, detection and other applications.

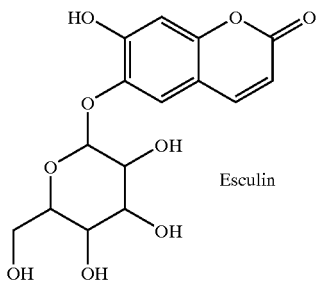

Esculin

In one non-limiting example the target is selected as the molecule Esculin. Esculin is desirable as a target in this embodiment since it is an amphiphilic molecule with a hydrophobic aromatic section and a hydrophilic carbohydrate section. The latex is formed from the known mixtures of styrene and divinylbenzene microemulsified in water with the aid of the cosurfactant hexadecyltrimethyl-ammonium bromide (M. Antonietti, *Macromol. Chem. Phys.*, 196: 441–446 (1995)). The monomer set comprises the recognition building block 4-vinylbenzoic acid, styrene and divinylbenzene as crosslinker. The monomer set including the cosurfactant and Esculin target are mixed in water. Polymerization is initiated and the SPC formed. Esculin is extracted via dialysis and the binding of fresh aliquots of Esculin to the SPC's is evaluated.

Waste Removal/Chelating Agent

When the target is a metabolic waste compound (or a mixture thereof), an absorption bed of the synthetic polymer complements is an effective tool for waste removal. The SPC may be used for the removal of infectious agents in a variety of medical treatments. The synthetic polymer complements may be used for rapid kidney dialysis or blood detoxification as well as for industrial reaction mixture purification. The SPCs further may be used to remove pollutants or other contaminants from chemical/biological preparations and from the environment (e.g., pesticides).

SPC Attachment to Spherical Particles

Figure 28:
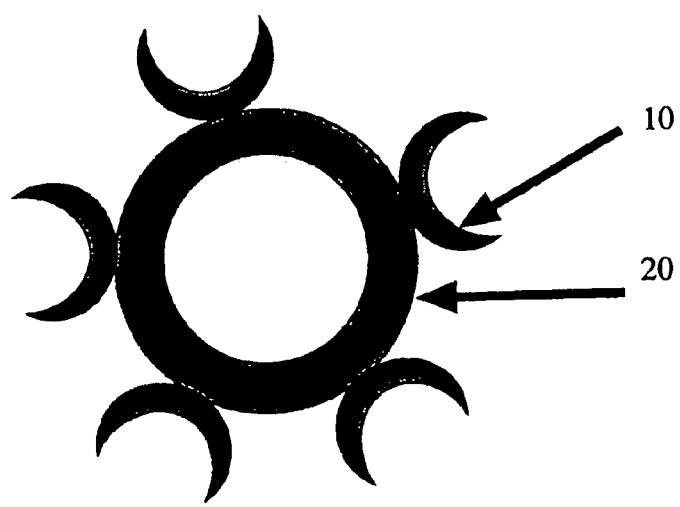
FIG. 28 is a schematic illustration of hollow ultrasound microspheres covalently attached to SPCs.

SPCs may be covalently attached to spheres. The spheres may be hollow or solid, and range in average diameter, for example, from 5 to 5000 nm. A preferred application of the invention is the attachment of SPCs to spheres that are generally employed for in vivo drug delivery or diagnostic applications. The spheres may be either purchased from commercial sources or custom fabricated. The attachment of SPC unit(s) to the spheres will allow the targeted delivery of the spheres to the desired tissues or cells. Example drug delivery applications include the delivery of solid nanospheres containing chemotherapy to tumors, such as the use of polyalkylcyanoacrylate nanospheres loaded with doxorubicin, used for M5076 hepatic metastesis (Chiannilkulchai et al., *Sel. Cancer Therapies*, 5:1 (1990)). An example diagnostic application is the use of gas-filled albumin microspheres for ultrasound imaging. Albumin microspheres for ultrasound imaging are commercially available from sources such as Mallinckrodt, Inc., St. Louis, Mo., under the trade name "Optison". A large SPC-hollow sphere complex is illustrated in FIG. 28.

Often, spheres of interest are at least partially composed of protein or carbohydrate residues. The SPCs can be attached to spheres via covalent bonding through generic synthetic routes (*Bioconjugate Techniques*, G. T. Hermanson, Academic Press, San Diego, 1996,). In the case of attachment to a protein, an SPC with N-hydroxysuccinimide ester moieties may react with the terminal amine or lysine side chain amine moieties. For SPC attachment to a carbohydrate, a carbohydrate hydroxyl moiety may first be functionalized with carbonyldiimidazole (CDI) to form an activated imidazole carbamate intermediate. An SPC with amine groups can subsequently react with the carbamate to form a stable urethane linkage to the carbohydrate. These examples are given for illustration purposes and do not limit the scope of the invention.

When spheres are composed of synthetic polymers or derivatives of biopolymers, standard chemical pathways can be used to link the SPC-spherical particle structures.

The SPC may also be attached to the spherical particle through strong physical bio-molecular interactions such as the avidin—biotin interaction, where an avidin unit is attached to the SPC and biotin is attached to the particle, or vise-versa. The attachment of biotin to a synthetic or natural polymer, called biotinylation, is well established (*Bioconjugate Techniques*, G. T. Hermanson, Academic Press, San Diego, 1996, Chapter 8, Section 3). The attachment of the protein avidin to substances is also well established (*Bioconjugate Techniques*, G. T. Hermanson, Academic Press, San Diego, 1996, Chapter 13, Section 3).

Detailed Synthesis and Use of Exemplary Monomers

Reactive Anionic Surfactants

Figure 10:
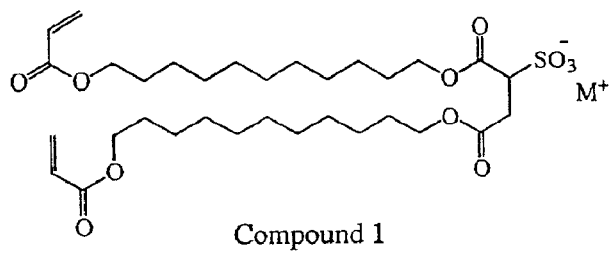
FIG. 10 illustrates the structure of compounds 1, 2 and 3, that each include a sulfonate head group, acrylate crosslinking group and hydrocarbon tail.
Figure 10:
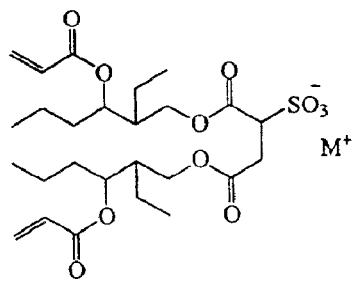
Figure 10:
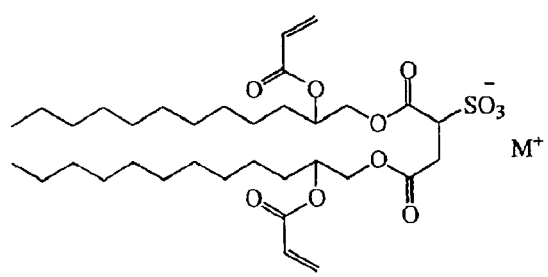

Surfactants with strongly anionic headgroups, such as sulfonates are commonly used in preparing micelles and reverse micelles. For example, Aerosol-OT (AOT) (bis(2-ethylhexylsulfosuccinate sodium salt, Aldrich Chemical Col. Milwaukee Wis.) forms reverse micelles (water-in-oil) without a cosurfactant for aliphatic solvent solubilization. Crosslinkable derivatives of surfactants such as AOT may be prepared with different tails, for example, comprising different branching and crosslinking groups. Different aspect ratios of the surfactants may be used, while maintaining a common head group. FIG. 10 shows the structures the exemplary reactive AOT derivatives (Compounds 1–3), where M is a metal ion, such as $Na^+$.

Comparing the structure of Compound 1 with AOT, the tails of the surfactant compound 1 have less branching and an acrylate at the terminal position. This decreases the wedge aspect ratio of the surfactant, which enables different morphologies with lower curvature in the oil phase. Compounds 2 and 3 have correspondingly more branching and increased wedge aspect ratio. Compound 3 advantageously has crosslinking groups closer to the polar head of the molecule, leaving a longer aliphatic apolar tail to "hang" into the solvent effectively.

Figure 11A:
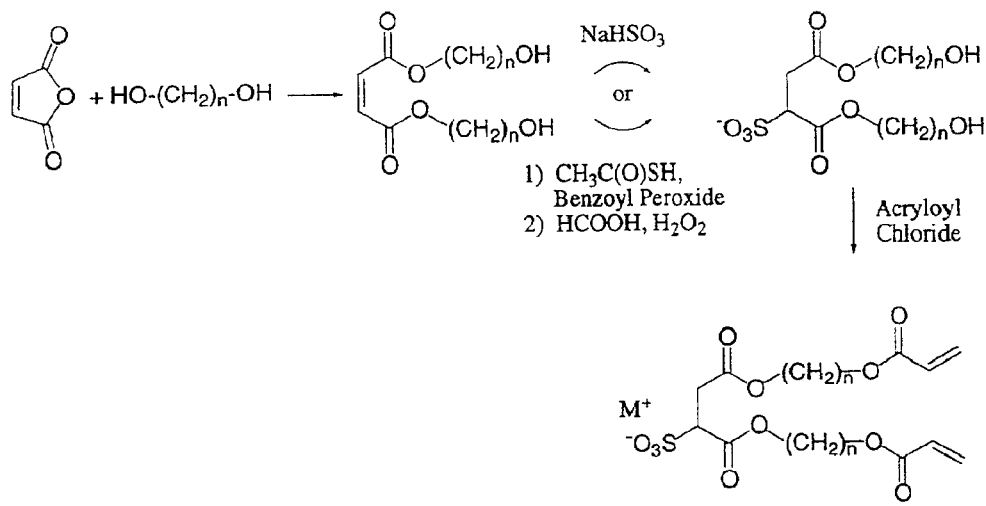
FIGS. 11a–11d depict other exemplary routes of synthesis of monomers with a sulfonate head group, acrylate crosslinking group and hydrocarbon tail.
Figure 11B:
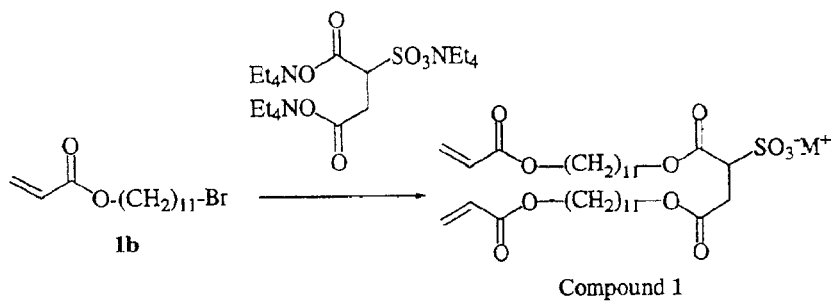
Figure 11C:
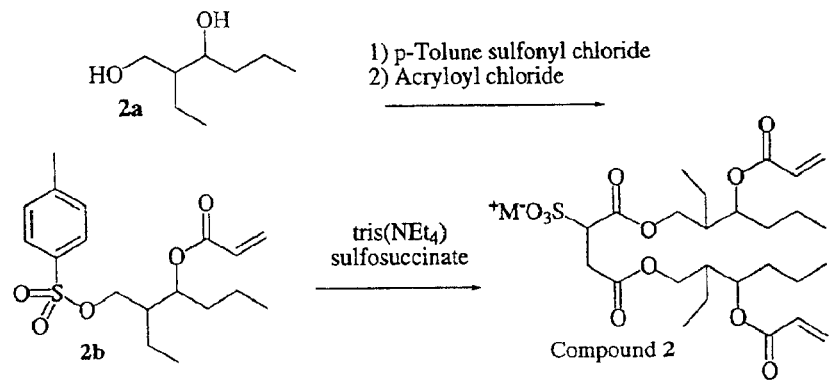
Figure 11D:
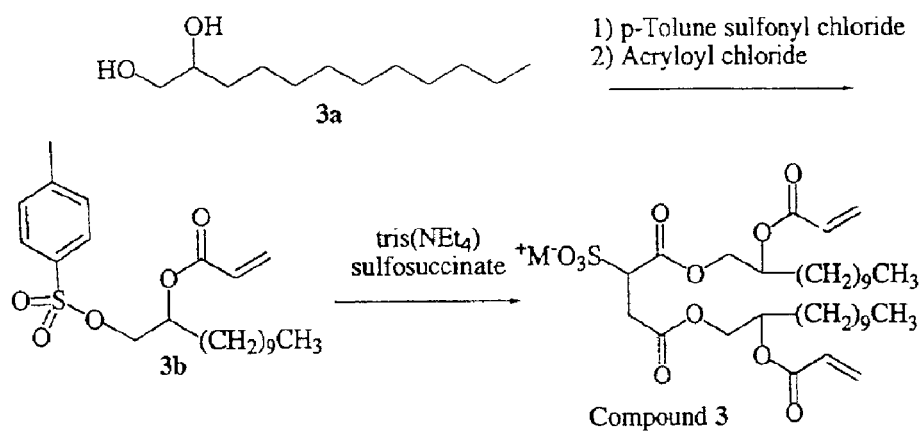
Figure 12:
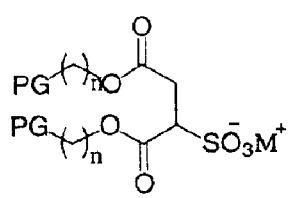
FIGS. 12 and 13 show exemplary monomers, wherein PG is a polymerizable group.
Figure 13:
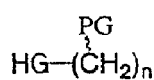
Figure 14:
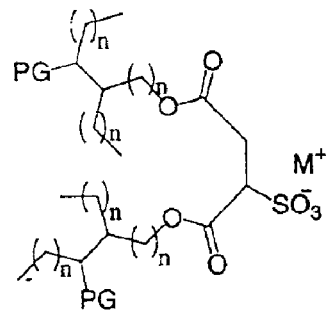
FIG. 14 is a schematic illustration of a branched monomer with a sulfonate head group and two polymerizable groups (PGs).
Figure 15:
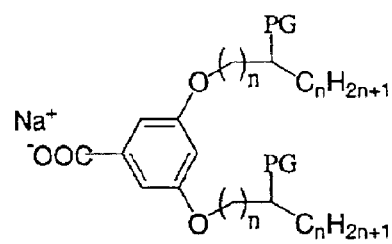
FIG. 15 is a schematic illustration of a two tailed monomer including two polymerizable groups (PGs) and a carboxylate head group.

Routes of synthesis of monomer compounds 1, 2 and 3 are shown in FIGS. 11b, 11c and 11d, respectively.

Compound 1 (bis(11-acryloylundecyl)sulfosuccinate) may be prepared via substitution at the alkyl bromide position of 11-bromoundecyl acrylate by the carboxylate salts of sulfosuccinic acid. Other acryloylated sulfosuccinic acid ester surfactants may be prepared using these methods.

Compound 2 (bis-(3-acryloyl-2-ethylhexyl) sulfosuccinate) and compound 3 (bis-2-acryloyldodecyl sulfosuccinate) may be prepared by similar methods, however in the preparation of the crosslinkable tail portion, the primary alcohol of a diol may be selectively protected as the p-tolunesulfononate ester followed by acryloylation of the secondary alchohol. The p-tolunesulfononate ester may then be displaced by the same carboxylate salts of sulfosuccinic acid.

Compounds 1–3 then may be converted to the sodium counterion by precipitation in aqueous sodium chloride, and subsequently purified via silica gel chromatography, for example, using as the eluant 10% methanol in methylene chloride.

Combinatorial-Based Syntheses

Structurally similar families of monomers may be made, wherein, for example, the only change is made to the head group. In one embodiment, the synthesis is conducted using substituted benzoic acids as the core group. Head and tail groups can be attached to these cores. Core regions with one, two or three tail attachment points as well as cores with multiple head groups may be fabricated. Head groups with, for example, side chains representing all 20 amino acids can be synthesized via the carbonyl group. Using various halogen substituted alcohol starting materials, the tail length, geometry and crosslinkable moiety substitution point can be altered or tailored as needed.

Figure 30:
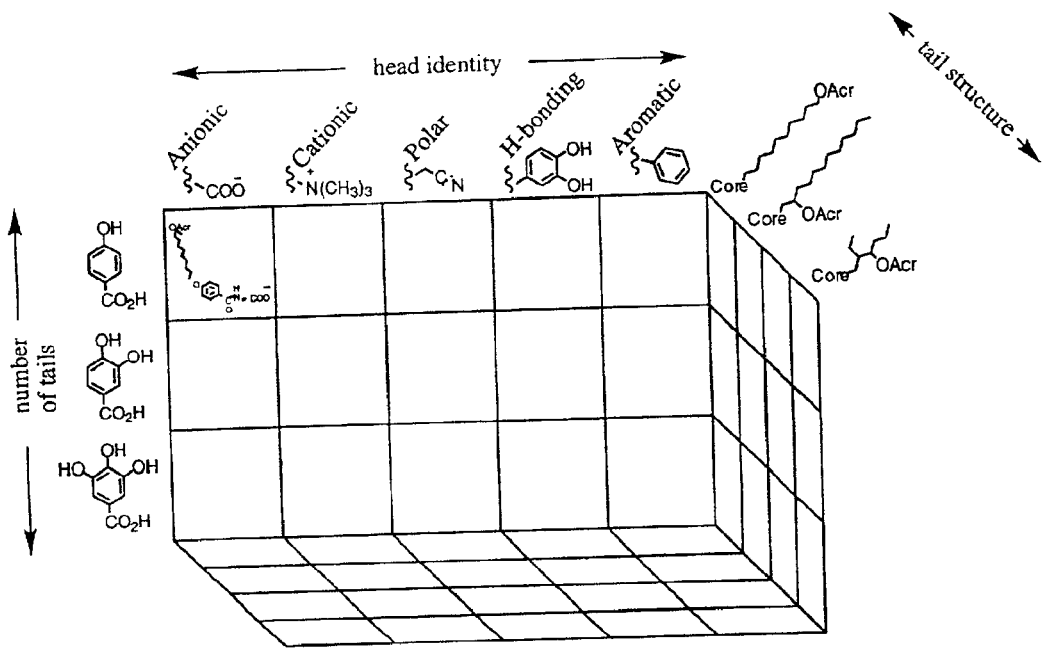
FIG. 30 is an illustration of a matrix showing possible monomers prepared by combinatorial based synthetic schemes.

In one embodiment, hydroxy substituted benzoic acids and the various tail moieties are attached via phenolic ether linkages. In another embodiment, methyl substituted benzoic acids and the tails are attached via cuprate coupling reactions. FIG. 30 is an illustration of a matrix showing in one embodiment the possibilities of these combinatorial based synthetic schemes, and the wide variety of molecules that can be synthesized in a combinatorial fashion.

Hydroxybenzoic Acid Base Monomers

Figure 31:
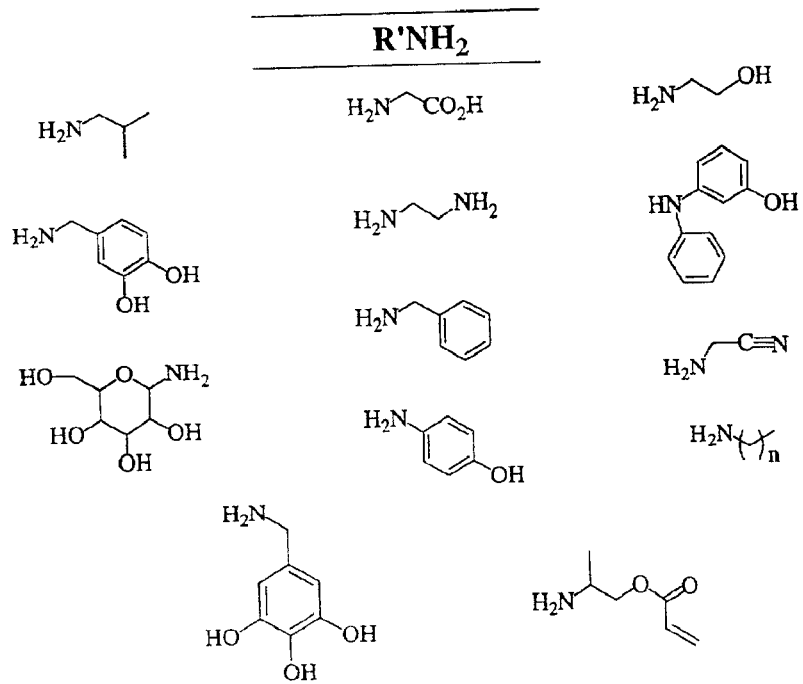
FIG. 31 shows exemplary amines that may be used to form a head group on monomers.

Hydroxybenzoic acids provide a convenient scaffold (also referred to as the core region) from which to prepare monomer building blocks. They are multiply functionalized molecules that are available in a wide variety of substitution patterns, allowing controlled structural diversity. A diverse variety of head group functionalities may be incorporated into the acid component via substituted amides. In one embodiment, the crosslinking group is incorporated at the terminal (ω-) position of the tail. ω-Functionalized 3-tailed monomers and compounds with the crosslinking group at the 2'-position, closer to the core, may be prepared. One-tailed 2'-substituted families of monomers also may be prepared. Listed in FIG. 31 are examples of the wide variety of commercially available amine reagents that may be used to add head group functionality to these monomers.

Figure 32:
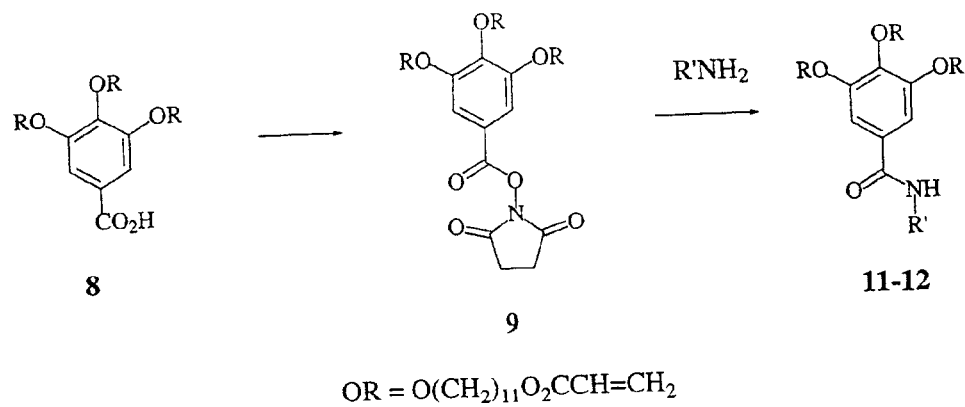
FIG. 32 is a scheme showing an exemplary synthesis of acryloylated monomers.
Figure 32:
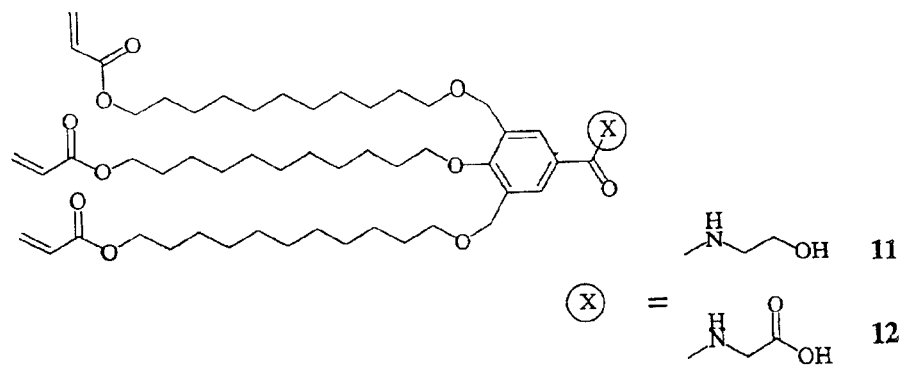

Using the synthetic route outlined in FIG. 32, exemplary monomers possessing a carboxylic acid (8, 12), sodium carboxylate salt (10) and hydroxyl (11) head moiety are synthesized. Preparation of these compounds follows a route based on hydroxy substituted benzoic acid cores, such as 4-hydroxybenzoic acid, 3,4-dihydroxybenzoic acid, or gallic acid (3,4,5-trihydroxybenzoic acid). Compound 8 is prepared as disclosed in Smith, R. C; Fischer, W. M.; Gin, D. L.; *J. Am. Chem. Soc*, 119:4092–4093 (1997). Via condensation of any of a wide variety of amines with the carboxylate of the benzoic acid, anionic, cationic, polar, hydrogen bonding and aromatic headgroups can be attached. FIG. 32 shows a convenient route whereby the carboxylic acid 8 is converted to the n-hydroxy succinimide ester 9, an activated ester that is easily crystallizable and purified in large scales. Any amine $R'NH_2$ will substitute at the activated ester on 8 to produce 11–12, the final monomers. This reaction (9→11–12) represents the key element of diversity in this combinatorial approach. Any head group (the R' functionality on 11) desired can be added to an easily synthesized and purified intermediate. The structures of these compounds are depicted in FIG. 32. Reaction of compounds of type 9 with any of the variety of amine reagents depicted in FIG. 31 will readily enable the preparation of a diverse library of tool set components.

Three-Tailed 2'-Acryloyl Monomer

In one embodiment, reactive surfactant monomers may be synthesized with the crosslinking group (the acrylate) located at a position other than the terminal (ω-) end of the tails. For this family of monomers, the polymerizable groups are located closer to the head group, while maintaining a long-chain solvophilic "tail".

Figure 33:
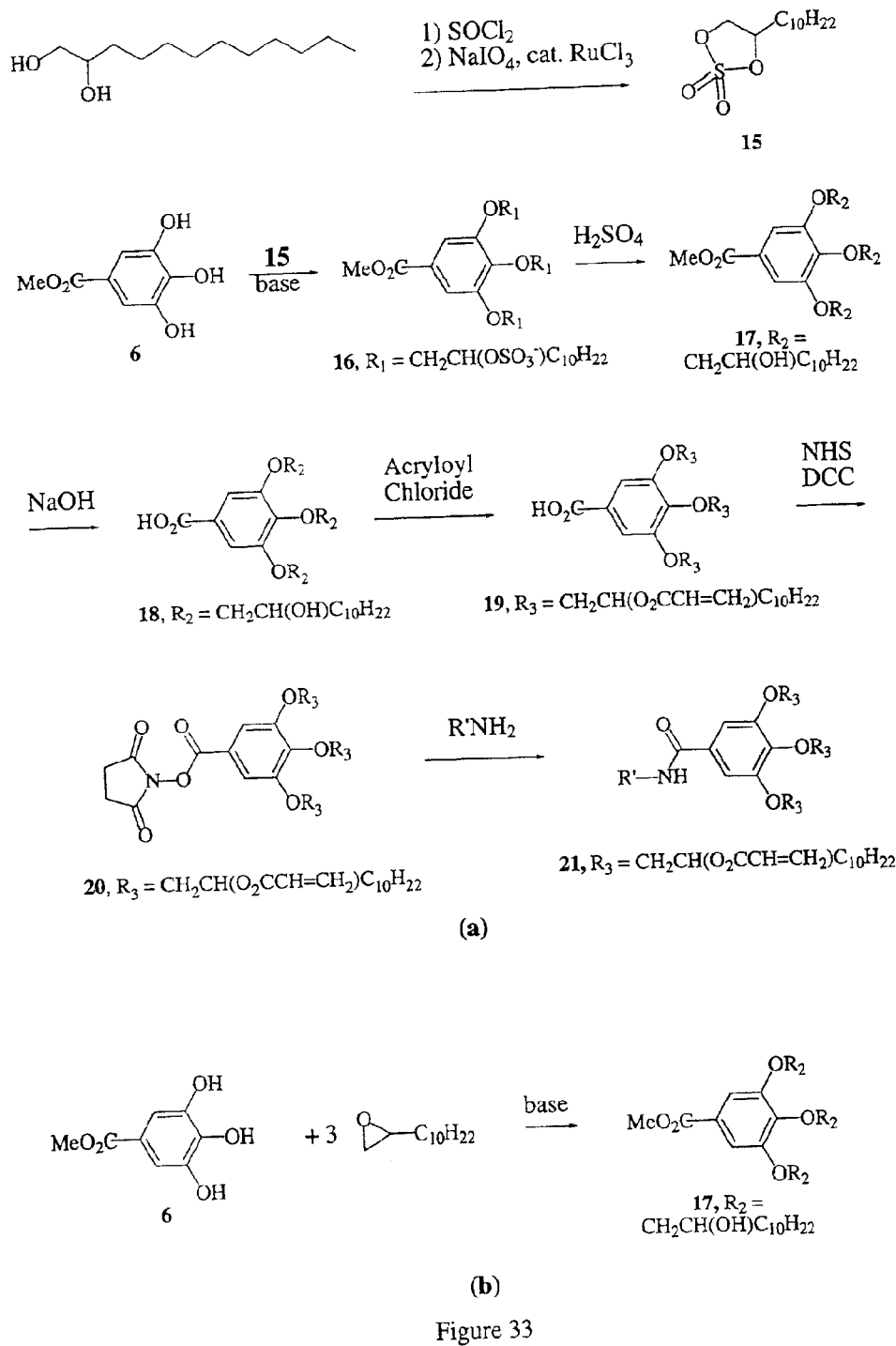
FIG. 33 is a scheme showing an exemplary synthesis of monomers.

The design of a structurally related tool set may be based on 1,2 diol starting materials. To provide a surfactant-performing tail, e.g. approximately $C_{6-20}$, 1,2-dodecanediol, for example, may be used for the core of the tail, providing a 12 carbon tail length similar to the 11 carbon tail used above for 8, 9, 11, and 12. A synthesis route is depicted in FIG. 33. Dodecanediol (13) is first converted into the labile cyclic sulfate derivative (15), as shown via the action of thionyl chloride (forming the cyclic sulfone (14)), followed by oxidation to 15 with sodium periodate. The cyclic sulfate 15 is a clear liquid that is isolated in high yield with only a simple silica filtration step. The cyclic sulfate 15 is ring-opened by the phenolic oxygens of methyl gallate (6), yielding the ether-linked trisulfate salt 16. Acidic hydrolysis of the sulfates yields 17, followed by basic hydrolysis of the methyl ester which will yield the hydroxy-aromatic acid 18. Treatment with acryloyl chloride adds the crosslinking functionality (19). The aromatic acid 19 may then be used as a building block of its own, analogous to 8 above, or it can be reacted via the NHS ester 20 to form 21. In 21, R' represents a head group, for example as listed in FIG. 31 for this monomer family.

One- And Two-Tailed 2'-Acryloyl Monomers

Figure 34:
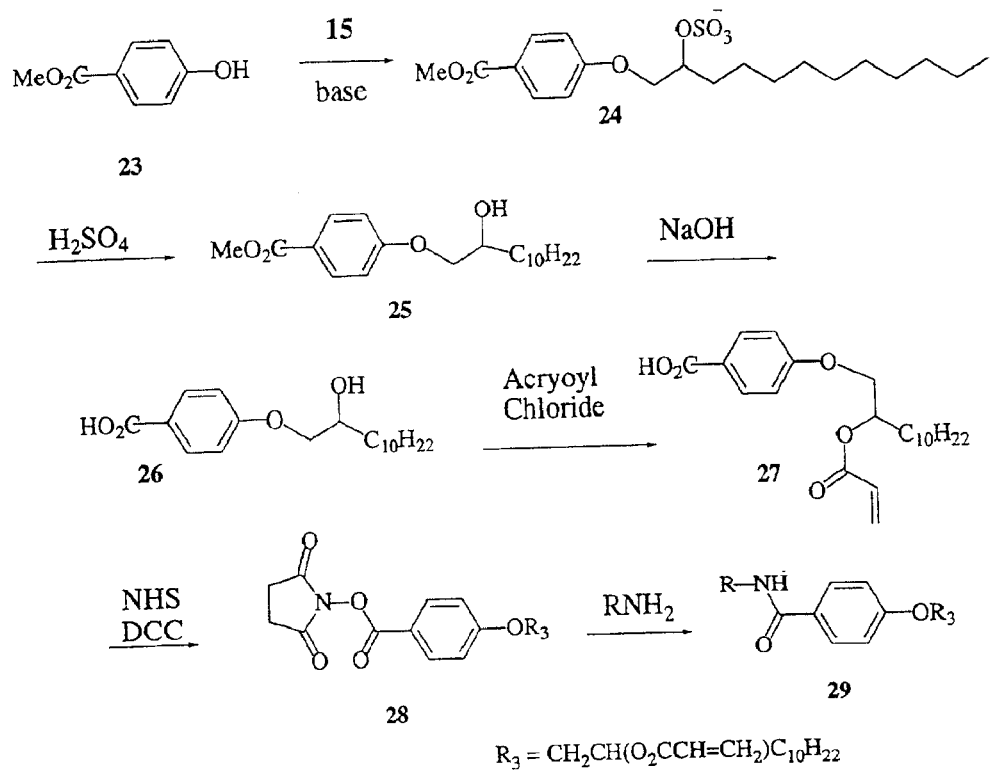
FIG. 34 is another scheme showing an exemplary synthesis of monomers.

Simpler one-tailed analogs of the three-tailed 2'-substituted monomers also may be prepared. A synthetic route is shown in FIG. 34. Substitution of the cyclic sulfate 15 by the phenol of methyl 4-hydroxy benzoate (23) yields the sulfate 24. Hydrolysis of 24's sulfate and methyl ester (sequentially) yields the hydroxy-acid 26. Treatment with acryloyl chloride attaches the crosslinking functionality (27). As above, the carboxylate headed structure (27) is one potential tool set component. It can also be elaborated with primary amines via the NHS ester 28 to yield 29, again R' representing a diverse set of headgroups. Optimal conditions for the addition of the cyclic sulfate 15 to 23 are potassium carbonate as the base, and DMF as solvent at room temperature. Slow addition of the cyclic sulfate can be used to minimize the excess amount needed. Acidic hydrolysis of the sulfate anion can be implemented following literature procedures (Y. Gao and K. B. Sharpless, *J. Am. Chem. Soc.*, 110:7538–7539 (1988)). Additional monomers, such as the two tailed material based on 3,5 dihydroxybenzoic acid also may be made analogously.

Methylbenzoic Acid Based Monomer Families

Figure 35:
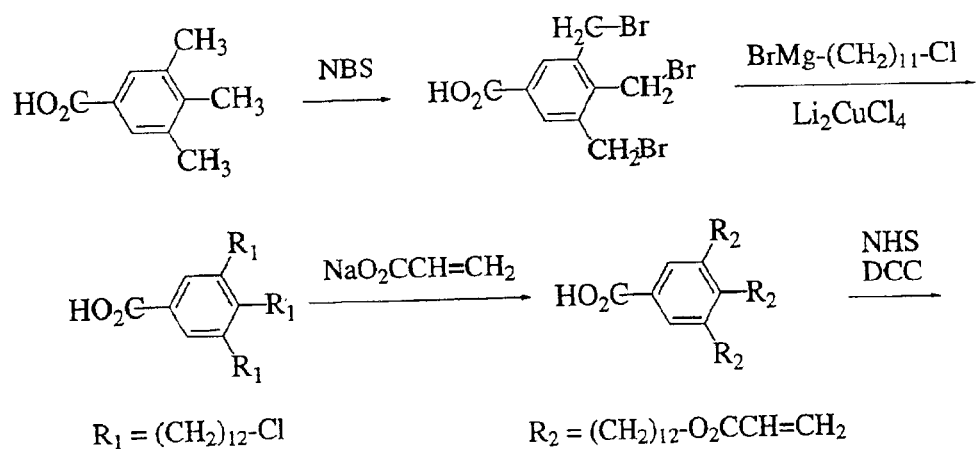
FIG. 35 is a scheme showing an exemplary synthesis of monomers of a surfactant family.
Figure 35:
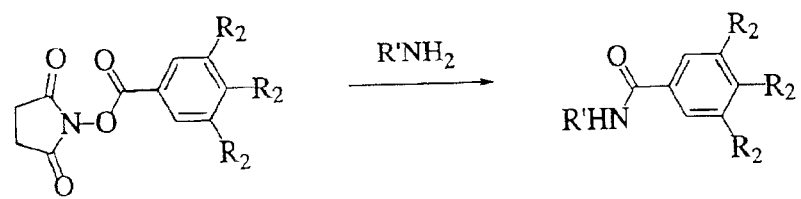

In another embodiment, a surfactant family is synthesized as outlined in FIG. 35, which avoids the ether linkages by starting from methyl substituted benzoic acids. Free-radical bromination selectively produces the bromomethyl substituted benzoic acids. The benzylic halogens are alkylated by a cuprate-mediated coupling. Subsequently, acryloyl chloride is added to the hydroxyl completing the tail. Via condensation of any of a wide variety of amines with the carboxylate of the benzoic acid, anionic, cationic, polar, hydrogen bonding and aromatic head groups are attached. Conveniently, the carboxylic acid is converted to the n-hydroxy succinimide ester, an activated ester that is easily crystallizable and purified in large scales. Any amine, R'NH$_2$, will substitute at the activated ester to produce the final monomer. The reaction represents the key element of diversity in this combinatorial approach. Any headgroup (the R' functionality) desired can be added to an easily synthesized and purified intermediate.

Sugar-Core Monomers

Carbohydrate-based surfactants are excellent tools in the assembly of active proteins in reverse micelles (Russell, A. J. et. al., *Biotechnology and Bioengineering*, 39, 1992, 806–814). Additionally, they facilitate high solids content inverse microemulsion polymerizations, as discussed by Candau and co-workers (Candau et. al., *Colloid & Polymer Science*, 271, 1993, 1055). A variety of compounds have proven effective. Commercial surfactants used include but are not limited to Span® 80, Span® 83, G-1086, Tween® 80 and Tween® 85 (ICI Specialties, Wilmington Del.). There are common elements to the published surfactants, namely that there is a sugar base or core and oleic acid esters as a hydrophobic tail. These materials have been shown to be effective and flexible, with both the hydrophobicity and hydrophilicity of the surfactant independently adjustable. Addition of polyethylene oxide repeat units to the sugar core adds hydrophilicity (lipophobicity) and increases the HLB (hydrophobic/lipophobic balance, *Journal of the Society of Cosmetic Chemistry*, 5, 1954, 249). Conversely, increasing the alkyl chain length, or adding more alkyl tails will decrease the HLB and increase the hydrophobicity. Blends of hydrophobic and hydrophilic surfactants have been effectively used to tune microemulsion properties to a specific monomer/polymer blend desired.

Figure 36:
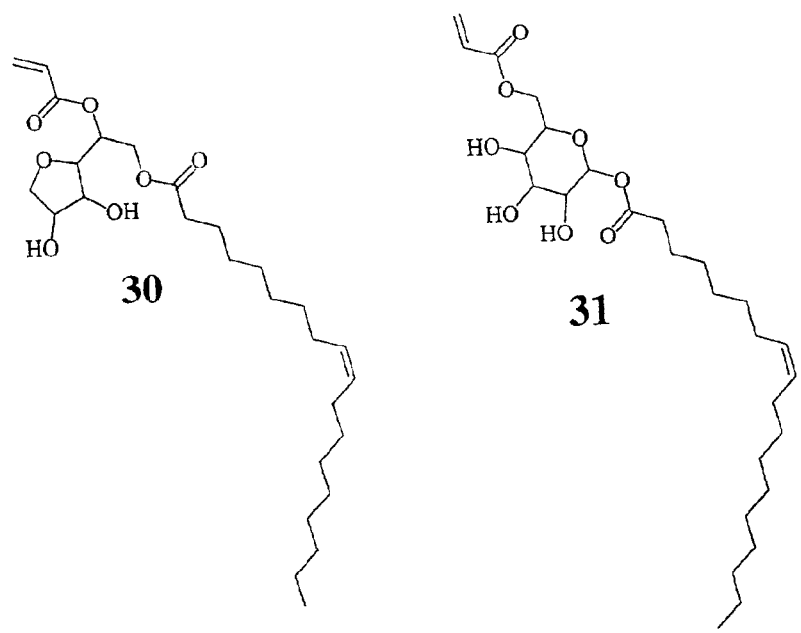
FIG. 36 is a schematic illustration of crosslinkable carbohydrate based surfactants.

Mixtures of carbohydrate-based nonionic surfactants such as Span 83 and Tween 80 (ICI Specialties, Wilmington Del.) are very flexible and useful for solubilization of a wide range of ionic and hydrophilic monomers in oil-continuous microemulsions. Thus, in one embodiment, crosslinkable carbohydrate based surfactants with structures and hydrophobicities similar to the above are formed, as shown in FIG. 36. The acrylate ester of Tween-80 is disclosed in U.S. Pat. No. 4,075,411.

Reactive acrylated derivatives of the hydrophobic surfactant Span-80 (sorbitan monooleate), which is commonly used in inverse microemulsions and suspensions, may be prepared, with control of the average number of acrylates per sugar.

Figure 37:
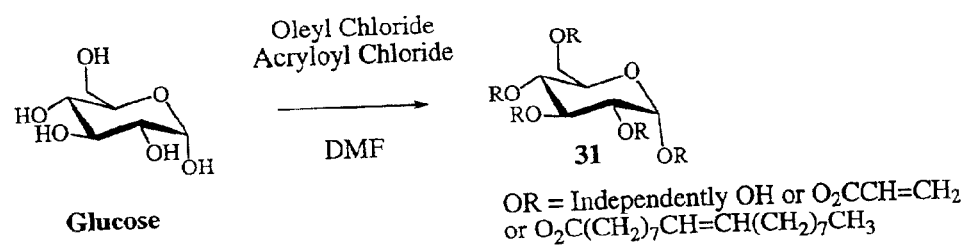
FIG. 37 is a scheme showing the synthesis of glucose monooleate monoacrylate.

In another embodiment, a pentahydroxylated sugar, glucose, as depicted in FIG. 37 is reacted to yield the glucose-based surfactant 31. This material has three free hydroxyls (on average) per molecule, and has a hydrophilic character.

The invention will be further understood by the following non-limiting examples.

All publications and patents referred to herein are incorporated herein by reference in their entirety.

EXAMPLES

Materials: Chemicals were obtained from the Aldrich Chemical Co. (Milwaukee Wis.) in reagent grade purity unless otherwise noted.

Example 1

Synthesis of Compound 1

A compound with a linear 11-carbon linker, as shown in FIG. 16 was prepared. 11-Bromoundecyl acrylate (1b) was prepared as disclosed in Joynes and Sherrington, *Polymer*, 37:1453–1462 (1996). Sulfosuccinic acid was neutralized by slow addition of tetraethylammonium hydroxide and the product was lyopholyzed. Tris(tetraethyl ammonium) sulfosuccinate (1 g) was added to 11-bromoundecylacrylate(1 mol equivalent) in anhydrous dimethylformamide (20 mL) solvent. Following 48 hours reaction at 40° C., the solvent was removed in vacuo. The crude product was dissolved in 1 ml methanol and precipitated in 10 ml 10% aqueous sodium chloride and purified by chromatography on silica (10% methanol in methylene chloride eluant).

Example 2

Synthesis of Compound 2

To a solution of 2-ethyl, 1-3hexane diol (5 g, mixture of isomers, Aldrich Chemical Co.) in methylene chloride (50 ml) with 2.5 mol. equiv. excess triethylamine was added p-toluenesulfonyl chloride (0.90 mol equiv.). The mixture was stirred at room temperature until consumption of the chloride was complete by tlc. Acryloyl chloride (1 mol equiv.) was added dropwise and the mixuture was stirred an additional 48 h. The solvent was removed in vacuo and the product extracted with hexane and filtered. The filtrate was chromatographed on silica (2% ethyl acetate in hexane). The isolated 3-acryloyloxy, 2-ethyl, 3-tosylhexane was reacted with tris(tetraethylammonium) sulfosuccinate and the product purified in the same manner as described above in Example 1.

Example 3

Synthesis of Anionic Compound 3

Using the above procedure described in Example 2 with 1,2-dodecanediol as the starting material, compound 3 was obtained.

Example 4

Ethanolamine-headed-tris(11-acryloyloxyundecyloxy)benzamide compound 12

Compound 8 (5 g) (prepared as disclosed in Smith, R. C; Fischer, W. M.; Gin, D. L.; *J. Am. Chem. Soc,*

119:4092–4093 (1997)) was treated with N-hydroxysuccinimide (1.05 mol equiv.) dicyclohexylcarbodiimide (1 mol. equiv.) in anhydrous THF (50 mL) and allowed to react for 24 h at 0° C. The NHS ester 9 was isolated via filtration and removal of solvent in vacuo and was carried on without further purification. Compound 9 (2.5 g) was then treated with ethanolamine (1 mol equiv.) in THF (50 ml) and allowed to react at 0° C. for 16 hours. Solvent was removed in vacuo and the residual redissolved in ethyl acetate. The organic layer was extracted with water and the product (12) purified by crystallization from ethyl acetate.

Example 5

Glycine-headed-tris(11-acryloyloxyundecyloxy) benzamide compound 11

Glycine (0.2 g) was dissolved in water (25 ml) with potassium carbonate (0.4 g). To this was added 25 mL THF and 2.4 g (9) (prepared as described above) and the mixture was allowed to react for 16 h at 0° C. The reaction mixture was acidified with 10% aq. HCl and extracted with ethyl acetate. The product (11) was crystallized from ethyl acetate.

Example 6

Cyclic Sulfate of 1,2-dodecanediol

Following the general procedure of Y. Gau and K. B. Sharpless, *J. Am. Chem. Soc.*, 110:7538–9 (1988), a solution of 1,2 dodecanediol (5.5 g) in $CCl_4$ (50 mL) was treated with $SOCl_2$ (2.4 mL) and heated to reflux for 90 min. The reaction mixture was cooled to 0° C. and diluted with acetonitrile (50 mL). Sodium periodate (1.5 mol. equiv) and ruthenium trichloride (0.1 mol %) were added followed by water (75 mL). The reaction was stirred vigorously at 0° C. one hour and subsequently at 25° C. one hour. The product (15) was isolated by extraction with diethyl ether and purification by silica gel chromatography

Example 7

Synthesis of 4-(2-acryloyloxydodecyloxy)benzoic acid (27)

Methyl 4-hydroxybenzoic acid was prepared according to the procedure disclosed in Gray, D. H., et al., *Advanced Materials*, 9:731–736 (1997). Methyl 4-hydroxybenzoic acid (4.1 g) was dissolved in 75 mL anhydrous DMF slurried with potassium carbonate (15 g). A solution of 1,2-dodecanediol cyclic sulfate (7.8 g) in anhydrous DMF (10 mL) was slowly added over 48 hours. The reaction mixture was filtered and the filtrate concentrated in vacuo and resuspended in diethyl ether (175 mL). An aquous solution of sulfuric acid (20%, 75 mL) was added and the mixture stirred until the reaction was complete by TLC. The phases were separated and the aqueous layer was extracted with 3×75 mL diethyl ether. The combined organic layers were dried over magnesium sulfate, evaporated and the residue was recrystallized from isopropyl alcohol to yield 4-(2-hydroxydodecyloxy) methyl benzoate (25). The methyl ester was hydrolyzed by aqeuous/methanolic base (3 M, 50% water, 50% methanol, 75 ml) The product (26) (0.5 g) was treated with acryloyl chloride (0.2 mL) in chloroform (50 ml) containing excess triethylamine base. and purified by silica gel chromatography to yield 27, 4-(2-acryloyloxydodecyloxy)benzoic acid.

Example 8

Synthesis of N-hydroxysuccinimidyl of 4-(2-acryloyloxydodecyloxy)benzoate (28)

The synthesis was conducted using the method described above in Example 4 for the synthesis of 9 using 27.

Example 9

Ethanolamine-headed-4-(2-acryloyloxydodecyloxy) benzamide compound (32)

The synthesis was conducted using the method described above in Example 4 for the synthesis of 12 using 28.

Example 10

Glycine-headed-4-(2-acryloyloxydodecyloxy) benzamide compound (33)

The synthesis was conducted using the method described above in Example 5 for the synthesis of 11 using 28.

Example 11

Oleyl Sorbitan Acrylate (Sorbitan Monooleylester Mono Acryloyl Ester)

Figure 44:
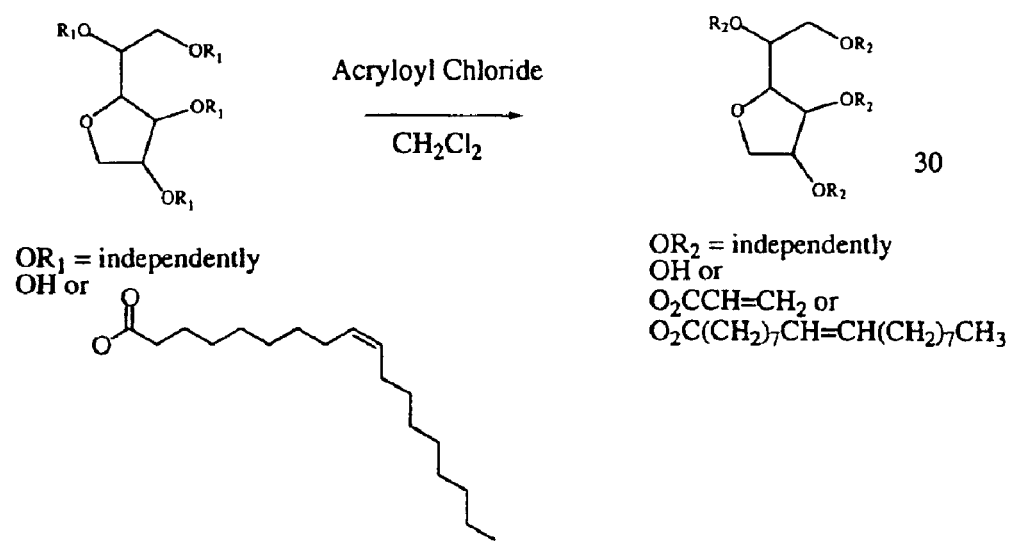
FIG. 44 is a scheme showing the synthesis of monomers such as Span-80 acrylate.

As shown in FIG. 44, treatment of Span®80 (12 g, Aldrich) with acryloyl chloride (0.90 mol. equiv) in methylene chloride (50 mL) containing 3 ml triethlamine yielded the crosslinkable derivative 30. The carbohydrate core (sorbitan) has four available hydroxyls for substitution and the product is a mixture of isomers. The monoacryloylmonooleate derivative (sorbitan monooleyl ester mono acryloyl ester) was isolated by chromatography on silica (1.5% methanol in methylene chloride).

Example 12

Oleyl Glucose Acrylate

To glucose (10 g) in anhydrous DMF (100 ml) containing excess triethylamine was added freshly distilled oleyl chloride (1 mol. equiv.), followed by acryloyl chloride after one hour reaction. The mixture was stirred overnight and the solvent removed in vacuo. The product was purified by hexane filtration followed by chromatography on silica (1.5% methanol in methylene chloride). We have applied the same transformation technology to a pentahydroxylated sugar, glucose, as depicted in FIG. 37 to yield the glucose-based compound 31, which is a mixture of regio and stereo isomers. This material has three free hydroxyls (on average) per molecule, and has a more hydrophilic character.

Example 13

Synthesis of Hydrophobically Modified Dextran

Figure 38:
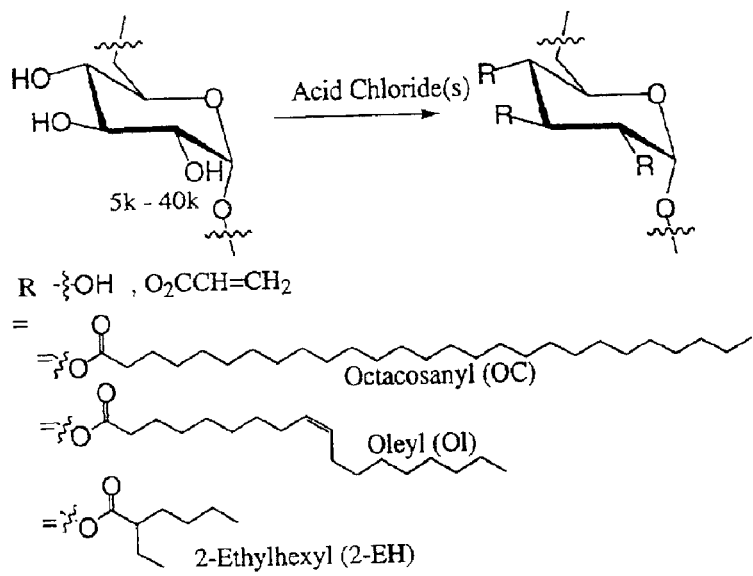
FIG. 38 is a scheme showing modification of dextran with acyl chlorides.
Figure 39:
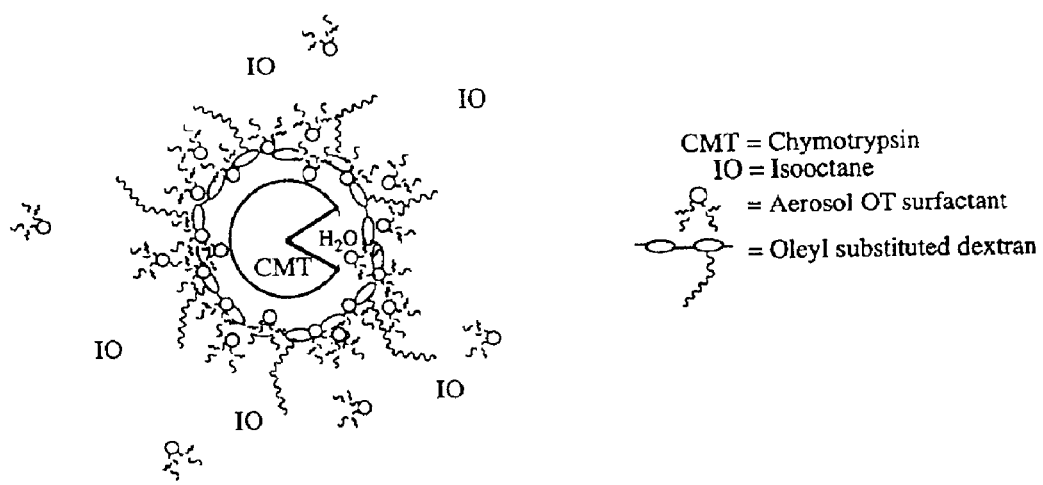
FIG. 39 is a schematic illustration of a superassembly formed upon extraction of chymotrypsin into isooctane in the presence of AOT and hydrophobically modified dextran.
Figure 40:
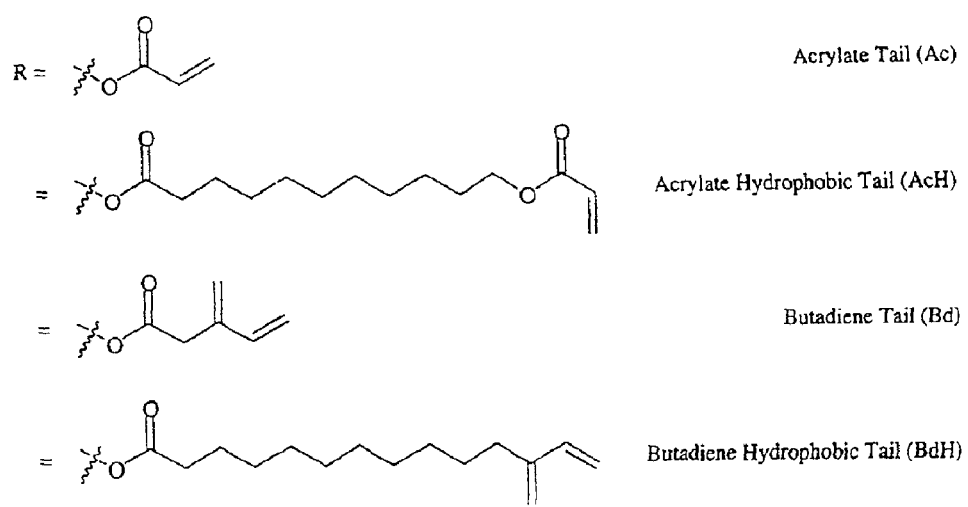
FIG. 40 is a schematic illustration of exemplary tails comprising radically crosslinkable groups.
Figure 41:
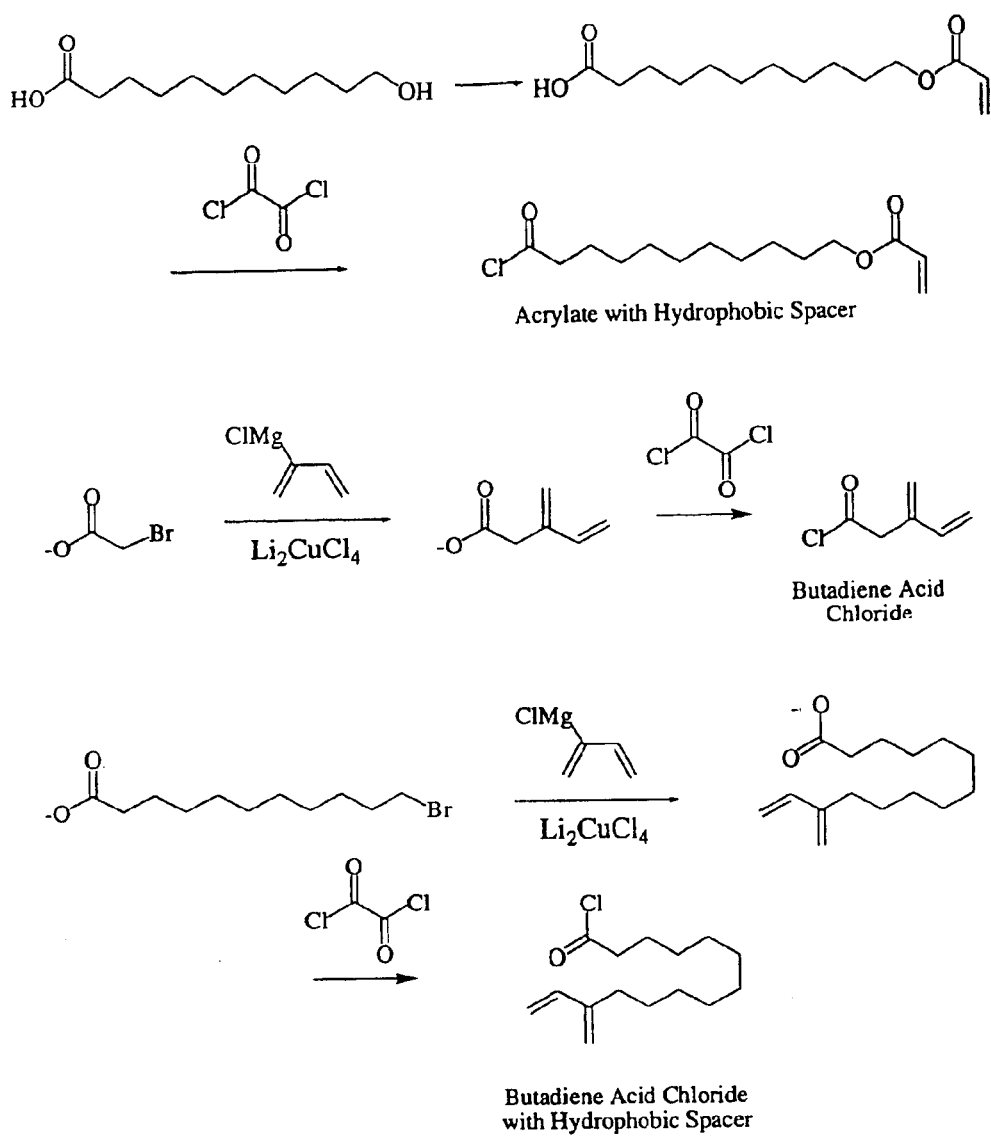
FIG. 41 is a scheme showing the synthesis of the acid chlorides of the radically crosslinkable tail groups of FIG. 40.
Figure 42:
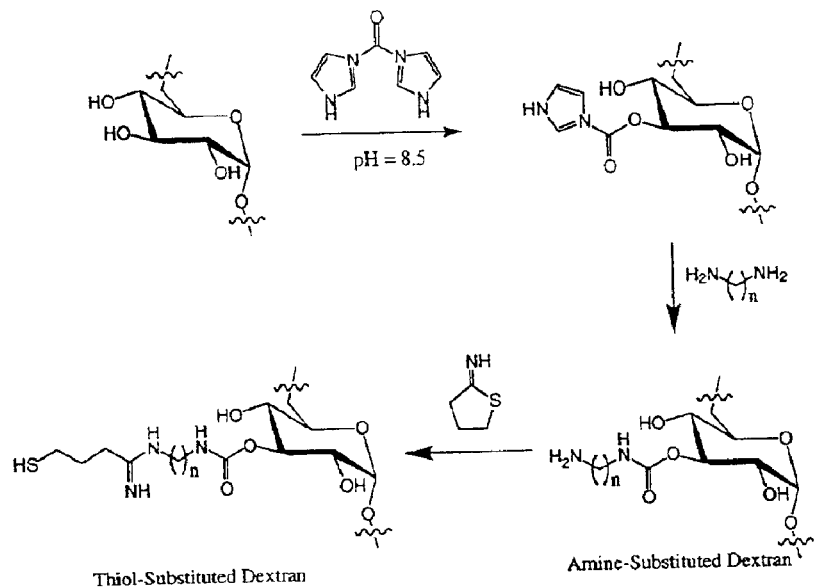
FIG. 42 is scheme showing the synthesis of an animated dextran.

In anhydrous DMSO (25 mL), dextran (40 kDa, 0.5 g, Carbomer Corp.) was dissolved in 0.55 mL pyridine. Oleyl chloride (2.67 mL, technical grade, Aldrich Chemical Co.) was added dropwise via syringe. The reaction was stirred 24 h and the product precipitated in methanol. The modified dextran was purified by repeated dissolution in 5 mL water followed by precipitation in methanol (40 mL) and finally lyopholized before use (see FIG. 38 for reaction scheme and tails used).

Example 14

α-Chymotrypsin Assembly Experiments with no Additives

A base direct injection of an aqueous solution consisting of 13 mg/ml CMT in 10 mM bis-trispropane buffer, pH 7.6 with 10 mM $CaCl_2$ (70 µL) was made into into isooctane containing 20 mM AOT (8 mL). After a short stirring period, a clear reverse micellular system was obtained. Assays were performed by dilution of the CMT-shell reverse micellular solutions to 0.1–10 µg/ml (overall) CMT in an isooctane solution that also contained 2 mM AOT, 1 mM APEE and 0.1–1 M n-propanol and analyzing for conversion of APEE to APPE by gas chromatography.

Example 15

α-Chymotrypsin Assembly Experiments with Hydrophobic Modified Dextrans

To the base aqueous CMT solution described above was added 40 mg/ml hydrophobically modified dextran substituted at the level of 1 oleyl chain/4 glucose units. A direct injection of (70 µL) was made into into isooctane (8 mL) containing 20 mM. After a short stirring period, a clear reverse micellular system was obtained. The enzymatic activity was assayed as above. Overall, solutions containing AOT/alkyl-dextrans show a four-fold increase over CMT/AOT activity in stability against the denaturing effects of 1 M n-propanol. At 40° C., CMT/modified dextrans had a 5-fold greater half life than CMT alone.

Example 16

Varying the Amount and Nature of Modified Dextrans

Various modified dextrans at 1M n-propanol concentration were compared. The activity rises with added modified dextran and appears to level off for all hydrophobic chains around 300 glucose units per CMT molecule (~3 g modified dextran per 1 g CMT). This suggests that the identity of the hydrophobic chain on the dextran is not important in n-propanol stability. Rather, it is the dextran itself that provides polar organic solvent stability. The chains only help the dextran to be extracted into the isooctane phase (dextran with no hydrophobic groups precipitates in isooctane). Overall, solutions containing AOT/alkyl-dextrans show a four-fold increase over CMT/AOT activity.

The heat stabilities of the various modified dextran/CMT solutions (3 g modified dextran per 1 g CMT, 1 M n-propanol) at 40° C. were compared. The stabilizing ability of the dextran towards CMT was not effected by the alkyl chain identity. The first-order decay constants and half-lives for the various solutions are presented in Table 5. All the solutions containing alkyl-dextrans have a considerably longer half-life than the CMT/AOT system. The best system, CMT/AOT/oleyl dextran, has a greater than 5-fold longer half-life than CMT/AOT at 40° C.

TABLE 5

Decay constants and half lives at 40° C. of AOT/modified dextran isooctane solutions with 1 M n-propanol.

| System | $t_{1/2}$ (min) |
|---|---|
| CMT/AOT | 3.4 |
| CMT/AOT/Oleyl Dextran | 17.7 |
| CMT/AOT/OC Dextran | 14.3 |
| CMT/AOT/2EH Dextran | 15.4 |

Example 17

α-Chymotrypsin Assembly Experiments with Co-Monomers

A direct injection of an aqueous solution consisting of the following components: 20 wt % acrylamide monomer, 3.9 wt. % methylene bisacrylamide crosslinker, 13 mg/ml CMT, 10 mM bis-trispropane buffer (pH 7.6) and 10 mM $CaCl_2$ (70 µL) was made into into isooctane (8 mL) containing 20 mM AOT and 20 mM Span-80-acrylate (prepared as described above) and photoinitators Irgacur and Darocur (Ciba Specialty Chemicals, Tarrytown, N.Y.) at a concentration of approximately 1 wt % total monomers. After a short stirring period, a clear reverse micellular system was obtained. The solution was degassed and irradiated for 60 min by a medium wavelength UV lamp (6 w) with constant stirring. The enzymatic activity was assayed as above. The activity of the polymerized system was found to remain at 83% of the original activity after 120 min incubation at 45° C. In comparison an analagous CMT-in-reverse-micelle system with no reactive building blocks and no crosslinking was found to only keep 50% of activity after 60 min. incubation at 45° C.

Example 18

α-Chymotrypsin SPC Formation Using Carbohydrate Compounds

A solution of 100 mM Span 83 and 100 mM Tween 80 was prepared in Isopar M (Exxon CO. USA, Houston, Tex.). An aqueous phase that is 28 wt % acrylamide, 12 wt % sodium acrylate and 3 wt % methylene bis acrylamide was prepared and added such that the water content of the final direct injection is 2 M. A buffered (10 mM bis tris propane, pH 7.6) 30 mg/ml solution of α-chymotrypsin was added such that the aqueous phase is 1 mg/ml α-chymotrypsin. A UV photoinitiator, 2-ethylanthraquinone was added at 1 mol % total acrylates. The solution was degassed and irradiated from a 6 w UV lamp for 20 min with constant stirring. To measure activity, the solution was diluted to to 20 mM both compounds, 0.1–1 M n-propanol and 0.5–5 mM APEE. Enzymatic activity was assayed as above. Activity was found to be equal to or greater than the AOT systems described above. Importantly, high activity at high enzyme concentrations is observed.

Example 19

Latex Surface Recognition of Esculin 1

An aqueous solution was prepared including 5–10 wt % hexadecyltrimethyl-ammonium bromide (CTAB), 5–10 wt % monomers (88% styrene, 2% vinylbenzoic acid, 10% divinylbenzene) and 3–9 mM Esculin. Polymerization was initiated by Irgacur and Darocur at 1 wt. % relative to the monomers upon irradiation via a 6 w UV lamp with constant stirring. The polymerized microspheres bound 70–90% of the Esculin in solution as determined by ultrafiltration and HPLC assay. Subsequent dialysis against water removed the bound Esculin quantitatively. Addition of fresh Esculin to the dialysed beads resulted in 25–50% of the Esculin sites rebinding. Control microspheres prepared with the same styrene, divinylbenzene, vinylbenzoic acid and CTAB mixture but no target molecule (Esculin) in the polymerization mixutre showed essentially no rebinding of esculin under identical conditions.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention.

What is claimed is:

1. A synthetic polymer complement ("SPC") comprising a crosslinked three-dimensional polymeric network having a diameter less than about 1000 nm and comprising target binding sites on its surface, the target binding sites being complementary to at least a portion of the surface topology and force field of a target, and wherein the polymeric network is comprised of monomers consisting of at least one crosslinking group and at least one head group selected from the group consisting of sugars, proteins, and carbohydrates, which head group is a functional group capable of undergoing a binding interaction with a site on the target.

2. A synthetic polymer complement according to claim 1, wherein the SPC is capable of specific recognition of the target.

3. A synthetic polymer complement according to claim 1, wherein the target binding sites comprise three-dimensional cavities complementary to at least a portion of the surface topology and force field of the target.

4. A synthetic polymer complement according to claim 3, wherein the three-dimensional cavities retain their topological and force field complementarity to the target when they are not bound to the target.

5. A synthetic polymer complement according to claim 1, wherein the target is selected from the group consisting of organic compounds, toxins, pollutants, pathogens, synthetic drugs, steroids, steroid derivatives, proteins, glycoproteins, polysaccharides, lipids, lipopolysaccharides, polyanions, nucleic acid, porphyrins, substituted porphyrins, and active agents.

6. A synthetic polymer complement according to claim 1, wherein the crosslinking group is selected from the group consisting of acrylate, methacrylate, acrylamide, vinyl ether, epoxide, methacrylamide, vinylbenzene, α-methylvinylbenzene, vinylbenzene, divinylbenzene, maleic acid derivative, diene, substituted diene, ihiol, alcohol, amine, carboxylic acid, carboxylic anhydride, carboxylic acid halide, aldehyde, ketone, isocyanate, succinimide, carboxylic acid hydrazide, glycidyl ether, sulane, siloxane, chlorosilane, alkoxysilane, alkyne, azide, 2'-pyridyldithiol, phenylglyoxal, iodo, maleimide, aryl halides, imidoester, dibromopropionate, and iodacetyl.

7. A synthetic polymer complement according to claim 1, wherein the crosslinking group is an aclylate, a methacrylate, an acrylamide, or a methacrylamide.

8. A synthetic polymer complement according to claim 1, wherein the polymeric network is further comprised of monomers consisting of a crosslinking group without a head group.

9. A synthetic polymer complement according to claim 8, wherein the crosslinking group is an acrylate, a methacrylate, an acrylamide, or a methacrylamide.

10. A synthetic polymer complement according to claim 1, wherein the polymeric network is further comprised of monomers consisting of a crosslinking group, a head group, and a tail region.

11. A synthetic polymer complement according to claim 10, wherein the tail region comprises a moiety selected from the group consisting of a poly(ethylene glycol), poly(ethylene oxide), poly(vinyl alcohol), poly(vinylpyrrolidone), poly(ethyloxazoline), poly(ethylene oxide)-co-poly(propyleneoxide) block copolymer, polysaccharide, a poly(amino acid), and a hydrocarbon moiety.

12. A synthetic polymer complement according to claim 1, wherein the target binding sites comprise a surface having at least one functional group capable of undergoing a binding interaction with a site on a target.

13. A synthetic polymer complement according to claim 1 which comprises from 1 to about 1000 target binding sites.

14. A synthetic polymer complement according to claim 1 which comprises from 1 to 1000 binding sites and wherein the head group is a carbohydrate, the crosslinking group is acrylamide, and the target is a protein.

15. A synthetic polymer complement according to claim 1 which comprises from 1 to 1000 binding sites and wherein the monomers comprise glucose-2-acrylamide.

16. A synthetic polymer complement ("SPC") comprising a crosslinked three-dimensional polymeric network having a diameter less than about 1000 nm, and wherein the SPC is capable of binding a target, and wherein the SPC is formed by:
providing a set of monomers, at least some of the monomers comprising i) at least one head group, which is a functional group capable of undergoing a binding interaction with a site on the target, the head group being selected from the group consisting of sugars, proteins, and carbohydrates; and ii) at least one crosslinking group, which is a reactive group capable of covalently reacting to crosslink monomers of the monomer set;
contacting the set of monomers with the target to permit the monomers to self assemble on the target;
reacting the crosslinking groups of the monomers of the monomer set; and
removing the target;
to form the SPC comprising one or more three-dimensional binding sites on its surface, the binding sites being complementary in shape to at least a portion of the surface of the target.

17. A synthetic polymer complement according to claim 16, wherein the crosslinking group is selected from the group consisting of acrylate, methacrylate, acrylamide, vinyl ether, epoxide, methacrylamide, vinylbenzene, α-methylvinylbenzene, vinylbenzene, divinylbenzene, maleic acid derivative, diene, substituted diene, thiol, alcohol, amine, carboxylic acid, carboxylic anhydride, carboxylic acid halide, aldehyde, ketone, isocyanate, succinimide, carboxylic acid hydrazide, glycidyl ether, silane, siloxane, chlorosilane, alkoxysilane, alkyne, azide, 2'-pyridyldithiol, phenylglyoxal, iodo, maleimide, aryl halides, imidoester, dibromopropionate, and iodacetyl.

18. A synthetic polymer complement according to claim 16, wherein the crosslinking group is an acrylate, a methacrylate, an acrylamide, or a methacrylamide.

19. A synthetic polymer complement according to claim 16, wherein the set of monomers further comprises monomers consisting of a crosslinking group without a head group.

20. A synthetic polymer complement according to claim 19, wherein the crosslinking group is an acrylate, a methacrylate, an acrylamide, or a methacrylamide.

21. A synthetic polymer complement according to claim 16, wherein the set of monomers further comprises monomers consisting of a crosslinking group, a head group, and a tail region.

22. A synthetic polymer complement according to claim 21, wherein the tail region comprises a moiety selected from the group consisting of a poly(ethylene glycol), poly(ethylene oxide) poly(vinyl alcohol), poly(vinylpyrrolidone), poly(ethyloxazoline), poly(ethylene oxide)-co-poly(propyleneoxide) block copolymer, polysaccharide, a poly(amino acid), and a hydrocarbon moiety.

23. A synthetic polymer complement according to claim 16, wherein the set of monomers further comprises a non-ionic surfactant.

24. A synthetic polymer complement according to claim 16, wherein at least some of the monomers are amphiphilic.

25. A synthetic polymer complement according to claim 16, wherein at least some of the monomers comprise a carbohydrate moiety.

26. A synthetic polymer complement according to claim 16, wherein at least some of the monomers comprise styrene, divinylbenzene or vinylbenzoic acid, and wherein the set of monomers further comprises a non-ionic surfactant.

27. A synthetic polymer complement according to claim 16 which comprises from 1 to about 1000 target binding sites.

28. A synthetic polymer complement according to claim 16 which comprises from 1 to 1000 binding sites and wherein the head group is a carbohydrate, the crosslinking group is acrylamide, and the target is a protein.

29. A synthetic polymer complement according to claim 16 which comprises from 1 to 1000 binding sites and wherein the set of monomers comprises glucose-2-acrylamide.

30. A composition comprising a synthetic polymer complement ("SPC") of claim 1 in a pharmaceutically acceptable carrier.

31. A composition according to claim 30, wherein the crosslinking group of the SPC is selected from the group consisting of acrylate, methacrylate, acrylamide, vinyl ether, epoxide, methacrylamide, vinylbenzene, α-methylvinylbenzene, vinylbenzene, divinylbenzene, maleic acid derivative, diene, substituted diene, thiol, alcohol, amine, carboxylic acid, carboxylic anhydride, carboxylic acid halide, aldehyde, ketone, isocyanate, succinimide, carboxylic acid hydrazide, glycidyl ether, silane, siloxane, chlorosilane, alkoxysilane, alkyne, azide, 2'-pyridyldithiol, phenylglyoxal, iodo, maleimide, aryl halides, imidoester, dibromopropionate, and iodacetyl.

32. A composition according to claim 30, wherein the polymeric network of the SPC further comprises monomers consisting of a crosslinking group without a head group.

33. A composition according to claim 30, wherein the polymeric network of the SPC further comprises monomers consisting of a crosslinking group, a head group, and a tail region.

34. A composition according to claim 33, wherein the tail region comprises a moiety selected from the group consisting of a poly(ethylene glycol), poly(ethylene oxide), poly(vinyl alcohol), poly(vinylpyrrolidone), poly(ethyloxazoline), poly(ethylene oxide)-co-poly(propyleneoxide) block copolymer, polysaccharide, a poly(amino acid), and a hydrocarbon moiety.

35. A composition according to claim 30, wherein the synthetic polymer complement comprises from 1 to 1000 binding sites and wherein the head group of the monomers of the SPC is a carbohydrate, the crosslinking group is acrylamide, and the target is a protein.

36. A composition according to claim 30, wherein the synthetic polymer complement comprises from 1 to 1000 binding sites and wherein the monomers of the SPC comprise glucose-2-acrylamide.

* * * * *